United States Patent
Basude

(10) Patent No.: US 11,185,413 B2
(45) Date of Patent: Nov. 30, 2021

(54) TISSUE GRASPING DEVICES AND RELATED METHODS

(71) Applicant: MedFree, Inc., Fremont, CA (US)

(72) Inventor: Raghuveer Basude, Fremont, CA (US)

(73) Assignee: MedFree, Inc., Fremont, CA (US)

( * ) Notice: Subject to any disclaimer, the term of this patent is extended or adjusted under 35 U.S.C. 154(b) by 0 days.

(21) Appl. No.: 16/246,866

(22) Filed: Jan. 14, 2019

(65) Prior Publication Data

US 2019/0142589 A1    May 16, 2019

Related U.S. Application Data

(63) Continuation of application No. PCT/US2017/042003, filed on Jul. 13, 2017.

(60) Provisional application No. 62/361,953, filed on Jul. 13, 2016, provisional application No. 62/617,946, filed on Jan. 16, 2018.

(51) Int. Cl.
   *A61F 2/24*      (2006.01)
   *A61B 17/122*    (2006.01)
   *A61B 17/00*     (2006.01)
   *A61B 90/00*     (2016.01)

(52) U.S. Cl.
   CPC ........ *A61F 2/2466* (2013.01); *A61B 17/1227* (2013.01); *A61F 2/2463* (2013.01); *A61B 90/361* (2016.02); *A61B 2017/00867* (2013.01); *A61F 2210/0014* (2013.01);
   (Continued)

(58) Field of Classification Search
   CPC ............ A61F 2230/0093; A61F 2/2418; A61F 2230/0045; A61F 2/2466; A61F 2220/0091; A61F 2220/0008; A61F 2/2454; A61F 2/246; A61F 2240/00; A61B 2017/0464; A61B 17/0401
   See application file for complete search history.

(56) References Cited

U.S. PATENT DOCUMENTS

3,671,979 A    6/1972  Moulopoulos et al.
3,874,338 A    4/1975  Happel et al.
(Continued)

FOREIGN PATENT DOCUMENTS

CN    106420113 A    2/2017
JP    2006528911 A   12/2006
(Continued)

OTHER PUBLICATIONS

Abe, et al. De Vega's annuloplasty for acquired tricuspid disease: Early and late results in 110 patients. The Annals of thoracic surgery 48.5 (1989): 670-676.
(Continued)

*Primary Examiner* — George J Ulsh
(74) *Attorney, Agent, or Firm* — Wilson Sonsini Goodrich & Rosati

(57) ABSTRACT

A clip for immobilizing leaflets of a cardiac or venous valve includes a hub having a pair of tangle resistant spring-biased outer arms coupled to an inferior end of the hub and a pair of tangle resistant spring-biased inner arms adjacent to the outer arms and coupled to a superior end of the hub. A delivery catheter may be used to position the valve clip adjacent a target valve while the outer and inner arms are biased in an opened position relative to each other. After the valve leaflets are located between the opened outer and inner arms, the biasing forces may be released to allow the clip to self-close the clip over the valve leaflets.

11 Claims, 65 Drawing Sheets

(52) U.S. Cl.
CPC ............... *A61F 2220/0016* (2013.01); *A61F 2220/0075* (2013.01); *A61F 2230/0054* (2013.01)

(56) References Cited

U.S. PATENT DOCUMENTS

| | | | |
|---|---|---|---|
| 4,056,854 A | 11/1977 | Boretos et al. | |
| 4,484,579 A | 11/1984 | Meno et al. | |
| 4,917,089 A | 4/1990 | Sideris | |
| 4,994,077 A | 2/1991 | Dobben | |
| 5,332,402 A | 7/1994 | Teitelbaum | |
| 5,411,552 A | 5/1995 | Andersen | |
| 5,478,344 A | 12/1995 | Stone et al. | |
| 5,554,185 A | 9/1996 | Block et al. | |
| 5,718,725 A | 2/1998 | Sterman et al. | |
| 5,769,812 A | 6/1998 | Stevens et al. | |
| 5,797,960 A | 8/1998 | Stevens et al. | |
| 5,823,956 A | 10/1998 | Roth et al. | |
| 5,829,447 A | 11/1998 | Stevens et al. | |
| 5,840,081 A | 11/1998 | Andersen et al. | |
| 5,855,614 A | 1/1999 | Stevens et al. | |
| 6,117,144 A | 9/2000 | Nobles et al. | |
| 6,269,819 B1 | 8/2001 | Oz et al. | |
| 6,461,366 B1 | 10/2002 | Seguin | |
| 6,629,534 B1 | 10/2003 | St. Goar et al. | |
| 6,752,813 B2 | 6/2004 | Goldfarb et al. | |
| 7,226,467 B2 | 6/2007 | Lucatero et al. | |
| 7,316,706 B2 | 1/2008 | Bloom et al. | |
| 7,449,024 B2 | 11/2008 | Stafford | |
| 7,464,712 B2 | 12/2008 | Oz et al. | |
| 7,509,959 B2 | 3/2009 | Oz et al. | |
| 7,563,267 B2 | 7/2009 | Goldfarb et al. | |
| 7,563,273 B2 | 7/2009 | Goldfarb et al. | |
| 7,604,646 B2 | 10/2009 | Goldfarb et al. | |
| 7,608,091 B2 | 10/2009 | St. Goar et al. | |
| 7,635,329 B2 | 12/2009 | Goldfarb et al. | |
| 7,655,015 B2 | 2/2010 | Goldfarb et al. | |
| 7,666,204 B2 | 2/2010 | Thornton et al. | |
| 7,682,319 B2 | 3/2010 | Martin et al. | |
| 7,704,269 B2 | 4/2010 | St. Goar et al. | |
| 7,736,388 B2 | 6/2010 | Goldfarb et al. | |
| 7,758,596 B2 | 7/2010 | Oz et al. | |
| 7,811,296 B2 | 10/2010 | Goldfarb et al. | |
| 7,938,827 B2 | 5/2011 | Hauck et al. | |
| 7,981,139 B2 | 7/2011 | Martin et al. | |
| 7,998,151 B2 | 8/2011 | St. Goar et al. | |
| 8,029,518 B2 | 10/2011 | Goldfarb et al. | |
| 8,052,592 B2 | 11/2011 | Goldfarb et al. | |
| 8,057,493 B2 | 11/2011 | Goldfarb et al. | |
| 8,123,703 B2 | 2/2012 | Martin et al. | |
| 8,133,239 B2 | 3/2012 | Oz et al. | |
| 8,187,299 B2 | 5/2012 | St. Goar et al. | |
| 8,216,230 B2 | 7/2012 | Hauck et al. | |
| 8,216,256 B2 | 7/2012 | Raschdorf, Jr. et al. | |
| 8,303,608 B2 | 11/2012 | Goldfarb et al. | |
| 8,323,334 B2 | 12/2012 | Deem et al. | |
| 8,343,174 B2 | 1/2013 | Goldfarb et al. | |
| 8,409,273 B2 | 4/2013 | Thornton et al. | |
| 8,470,028 B2 | 6/2013 | Thornton et al. | |
| 8,721,665 B2 | 5/2014 | Oz et al. | |
| 8,734,505 B2 | 5/2014 | St. Goar et al. | |
| 8,740,918 B2 | 6/2014 | Seguin | |
| 8,740,920 B2 | 6/2014 | Goldfarb et al. | |
| 10,159,570 B1 | 12/2018 | Metchik et al. | |
| 2004/0049207 A1 | 3/2004 | Goldfarb et al. | |
| 2008/0167750 A1 | 7/2008 | Stahler et al. | |
| 2009/0054902 A1 | 2/2009 | Mickiewicz et al. | |
| 2012/0065464 A1 | 3/2012 | Ellis et al. | |
| 2013/0066341 A1 | 3/2013 | Ketai et al. | |
| 2013/0066351 A1 | 3/2013 | Giardina et al. | |
| 2013/0150710 A1 | 6/2013 | Zentgraf et al. | |
| 2013/0282059 A1 | 10/2013 | Ketai et al. | |
| 2013/0338764 A1 | 12/2013 | Thornton et al. | |
| 2014/0236187 A1 | 8/2014 | Seguin et al. | |
| 2014/0236198 A1 | 8/2014 | Goldfarb et al. | |
| 2015/0223793 A1 | 8/2015 | Goldfarb et al. | |
| 2015/0257877 A1 | 9/2015 | Hernandez | |
| 2015/0257883 A1 | 9/2015 | Basude et al. | |
| 2017/0020521 A1 | 1/2017 | Krone et al. | |
| 2019/0030285 A1 | 1/2019 | Prabhu et al. | |
| 2020/0229806 A1 | 7/2020 | Goldfarb et al. | |

FOREIGN PATENT DOCUMENTS

| | | |
|---|---|---|
| WO | WO-9101689 A1 | 2/1991 |
| WO | WO-9835638 A1 | 8/1998 |
| WO | WO-9900059 A1 | 1/1999 |
| WO | WO-9901377 A1 | 1/1999 |
| WO | WO-0003759 A3 | 4/2000 |
| WO | WO-0060995 A2 | 10/2000 |
| WO | WO-0060995 A3 | 4/2001 |
| WO | WO-2004103162 A3 | 8/2005 |
| WO | WO-2014136056 A1 | 9/2014 |
| WO | WO-2016133950 A1 | 8/2016 |
| WO | WO-2017015288 A2 | 1/2017 |
| WO | WO-2018013856 A1 | 1/2018 |
| WO | WO-2019010370 A1 | 1/2019 |
| WO | WO-2019143726 A1 | 7/2019 |

OTHER PUBLICATIONS

Alvarez, et al. Repairing the degenerative mitral valve: ten-to fifteen-year follow-up. The Journal of Thoracic and Cardiovascular Surgery112.2 (1996): 238-247.

Bach, et al. Early improvement in congestive heart failure after correction of secondary mitral regurgitation in end-stage cardiomyopathy. American heart journal129.6 (1995): 1165-1170.

Bach, et al. Improvement following correction of secondary mitral regurgitation in end-stage cardiomyopathy with mitral annuloplasty. The American journal of cardiology 78.8 (1996): 966-969.

Bolling, et al. Early outcome of mitral valve reconstruction in patients with end-stage cardiomyopathy. The Journal of thoracic and cardiovascular surgery 109.4 (1995): 676-683.

Cosgrove, et al. Tricuspid valve repair with the Cosgrove-Edwards annuloplasty system. The Annals of thoracic surgery 64.1 (1997): 267-268.

Dec, et al. Idiopathic dilated cardiomyopathy. New England Journal of Medicine 331.23 (1994): 1564-1575.

Fucci, et al. Improved results with mitral valve repair using new surgical techniques. European journal of cardio-thoracic surgery 9.11 (1995): 621-627.

Kameda, et al. Annuloplasty for severe mitral regurgitation due to dilated cardiomyopathy. The Annals of thoracic surgery 61.6 (1996): 1829-1832.

Khan, et al. Blade atrial septostomy: experience with the first 50 procedures. Catheterization and cardiovascular diagnosis 23.4 (1991): 257-262.

Maisano, et al. The edge-to-edge technique: a simplified method to correct mitral insufficiency. European Journal of Cardio-thoracic Surgery 13.3 (1998): 240-246.

Meritmedical. HeartSpan® Steerable Sheath Introducer, https://www.merit.com/cardiac-intervention/ep-and-crm/electrophysiology/heartspan-steerable-sheath-introducer/. Downloaded Apr. 29, 2019. 5 pages.

Park, et al. Clinical use of blade atrial septostomy. Circulation 58.4 (1978): 600-606.

Ricchi, et al. Linear segmental annuloplasty for mitral valve repair. The Annals of thoracic surgery 63.6 (1997): 1805-1806.

Tager, et al. Long-term follow-up of rheumatic patients undergoing left-sided valve replacement with tricuspid annuloplasty—validity of preoperative echocardiographic criteria in the decision to perform tricuspid annuloplasty. The American journal of cardiology 81.8 (1998): 1013-1016.

Uchida, et al. Percutaneous cardiomyotomy and valvulotomy with angioscopic guidance. American heart journal 121.4 (1991): 1221-1224.

Umana, et al. "Bow-tie" mitral valve repair: an adjuvant technique for ischemic mitral regurgitation. The Annals of Thoracic Surgery 66.5 (1998): 1640-1645.

(56) References Cited

OTHER PUBLICATIONS

International Search Report and Written Opinion for PCT/US2019/013853 dated Apr. 11, 2019.
EP17828492.3 Extended European Search Report dated Jun. 24, 2020.
PCT/US2017/042003 International Search Report and Written Opinion dated Sep. 29, 2017.

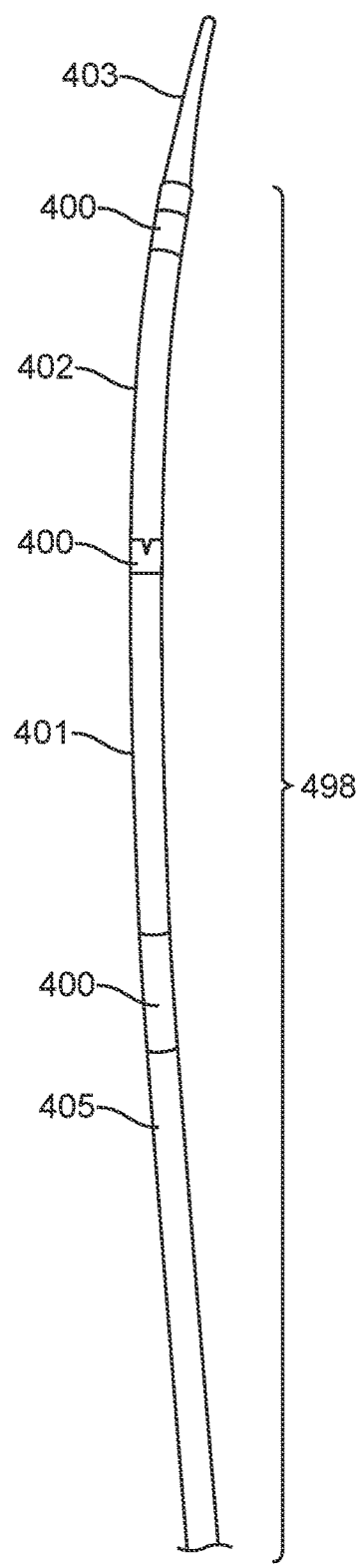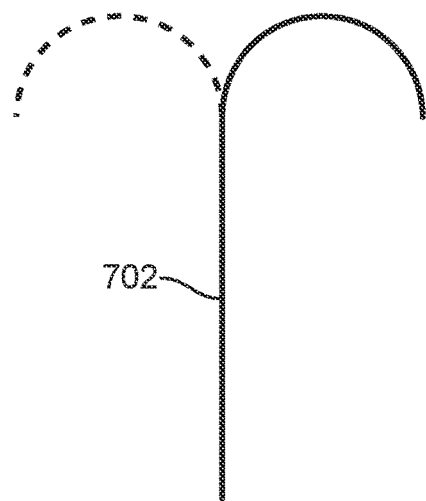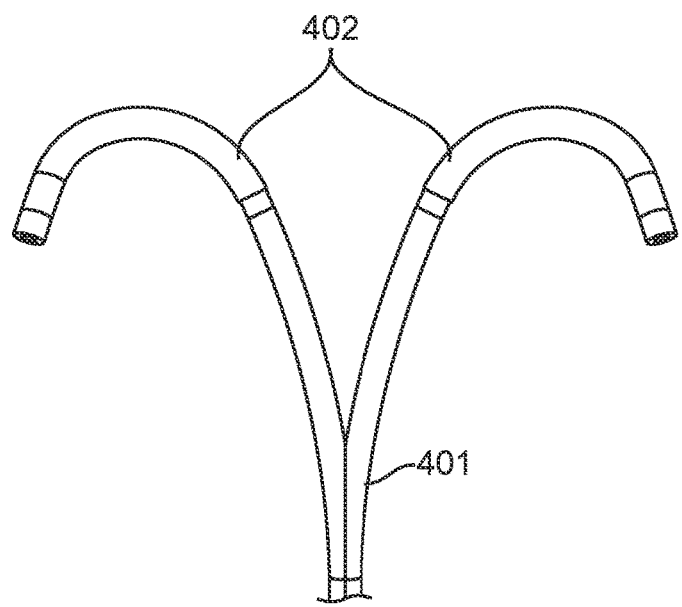
FIG. 2Q-1
FIG. 2Q-2
FIG. 2Q-3

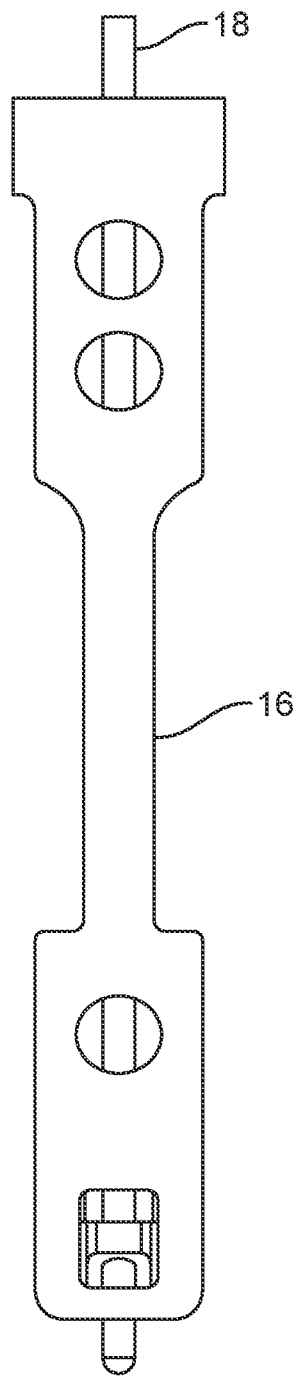 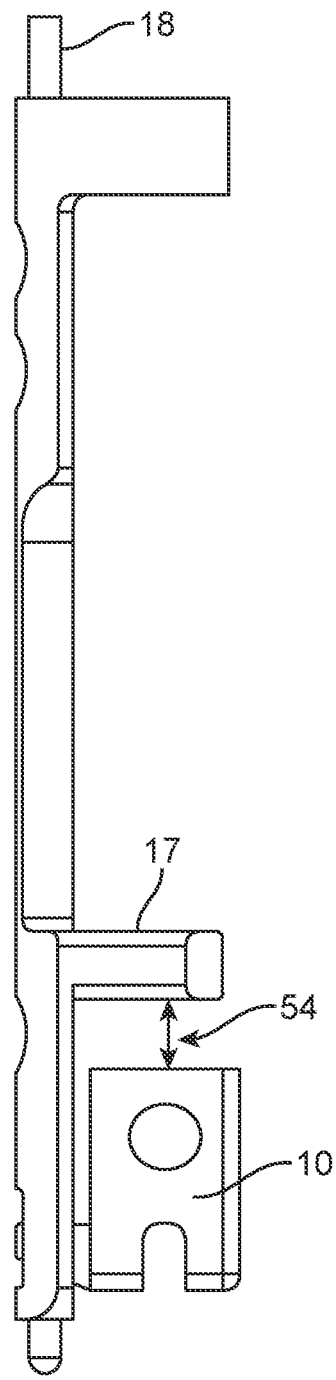
FIG. 13H-1     FIG. 13H-2

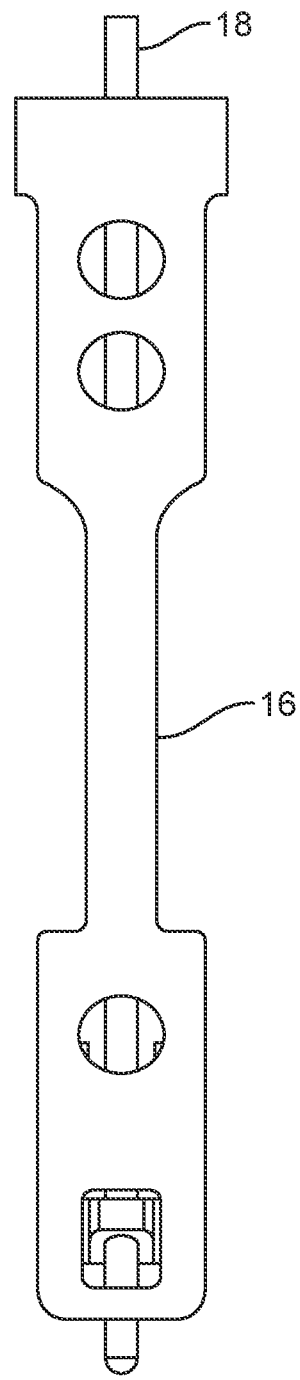 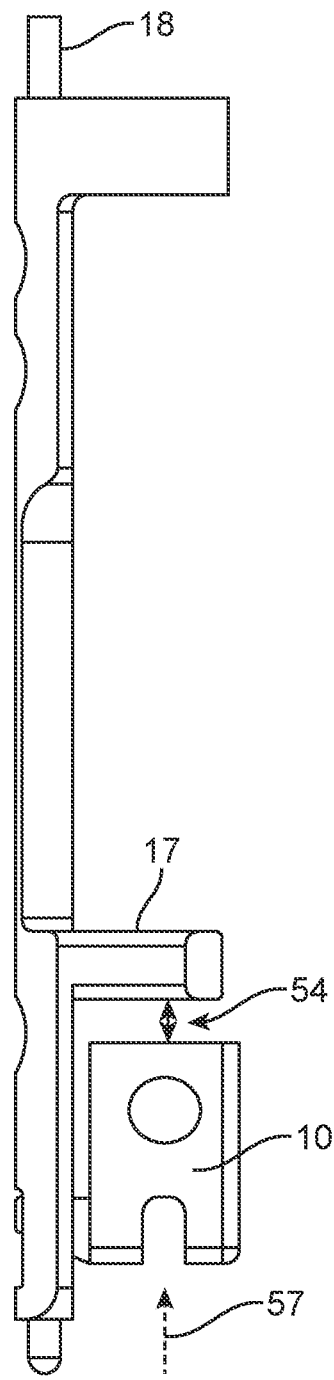
FIG. 13I-1        FIG. 13I-2

- Final Angle (Af, Bf, Cf, Df) = 0 to 180 degrees;
- Angle Af ≥ Angle Bf; or Angle Af ≤ Angle Bf; or Angle Af ≠ Angle Bf
- Angle Cf ≥ Angle Df; or Angle Cf ≤ Angle Df; or Angle Cf ≠ Angle Df

- Shape-Set Angle (As, Bs, Cs, Ds) = 0 to 180 degrees
- Angle As ≥ Angle Bs; or Angle As ≤ Angle Bs; or Angle As ≠ Angle Bs
- Angle Cs ≥ Angle Ds; or Angle Cs ≤ Angle Ds; or Angle Cs ≠ Angle Ds Final Vs Shape-Set Angle

- Angle Af ≤ Angle As; Angle Bf ≤ Angle Bs;
- Angle Cs ≤ Angle Cf; Angle Df ≤ Angle Ds;
- Angle As ≠ Angle Bf; Angle Cs ≠ Angle Ds

TISSUE GRASPING DEVICES AND RELATED METHODS

CROSS-REFERENCE TO RELATED APPLICATIONS

This application is a continuation of PCT Application No. PCT/US17/42003, filed Jul. 13, 2017, which claims the benefit of Provisional Application No. 62/361,953, filed Jul. 13, 2016, the entire content of which is incorporated herein by reference; this application also claims the benefit of Provisional Application No. 62/617,946, filed Jan. 16, 2018, the entire content of which is incorporated herein by reference.

BACKGROUND OF THE INVENTION

1. Field of the Invention

The present invention relates generally to medical methods, devices, and systems. In particular, the present invention relates to methods, devices, and systems for the endovascular, percutaneous, or minimally invasive surgical treatment of bodily tissues, such as tissue approximation or valve repair. More particularly, the present invention relates to methods and devices for the repair of mitral and tricuspid heart valves, venous valves, and other tissue structure through minimally invasive and other procedures.

Surgical repair of bodily tissues often involves tissue approximation and fastening of such tissues in the approximated arrangement. When repairing valves, tissue approximation often includes coapting the leaflets of the valves in a therapeutic arrangement which may then be maintained by fastening or fixing the leaflets. Such fixation of the leaflets can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle during systole.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and is associated with high mortality and morbidity.

In some patients, a fixation device can be installed into the heart using minimally invasive techniques. The fixation device can hold the adjacent segments of the opposed valve leaflets together to reduce mitral valve regurgitation. One such device used to clip the anterior and posterior leaflets of the mitral valve together is the MitraClip® fixation device, sold by Abbott Vascular, Santa Clara, Calif., USA.

Fixation devices such as the MitraClip® valve leaflet fixation device often include clips designed to grip and hold valve tissue as the clip arms are moved and positioned against the tissue at the treatment site and then closed against the tissue. Such clips are designed to be closed into a final position and then mechanically lock into that position in order to continue gripping the tissue.

In addition, the act of grasping and closing into final position causes the leaflet and potentially the annulus to cinch. Considering that the MitraClip® is a relatively stiff device with steel (Elgiloy®) arms that are mechanically locked, the natural expansion and contraction of the annulus is altered.

Furthermore, in order to achieve bailout to remove or reposition the device, it is required to flex the device at extreme angles (to the point of inversion) to release the grasp. This extreme moving and deforming components of the fixation device during pre-deployment, positioning, closure and bail out of the device can lead to the weakening and pre-mature degradation of the fixation device. In addition, it makes the device extremely complex with multiple components, and contributes to a relatively large overall size of the device, and therefore a correspondingly large (~24Fr for MitraClip® fixation device) delivery system. This large catheter size presents additional trauma to the patients. In comparison, typical trans-septal introducer sheaths are 8.5Fr to 12 Fr (inner diameter) and 9 Fr to 16 Fr (outer diameter).

Some tissue fixation treatments require that the fixation device maintain a degree of flexibility and mobility to allow for a range of physiological movement even after the device has been properly deployed and the target tissue has been properly fixed into the desired position. This can increase the risk of pre-mature failure of the device's complex locking mechanism as continued deformation of the flexing components (e.g., from the continuous opening and closing of valve leaflets) leads to unfavorable degradation of the device.

Depending on the anatomy and disease state of the valves, there can be variations in the coapting lengths and dissimilarities in leaflet shape in general (for example dissimilarities between anterior and posterior mitral valve leaflets). However, current devices and market leader MitraClip® fixation device comes in only one size. This can create issues for physicians when presented with various valve sizes, coapting lengths, frailty, and various functional and degenerative valve defects to be treated.

The ability to bailout and reposition is an important safety consideration for a majority of medical devices. The current market leader MitraClip® fixation device possesses these attributes to some extent, as it allows for bailout and repositioning. However, it occasionally presents a safety risk wherein tissue or delivery mechanisms may become caught in the barbs of the tissue grabbing features.

Finally, visualization during and after the procedure plays a critical role in the successful delivery of the device and outcome of the result. The current state-of-the-art device relies on fluoroscopy and transesophageal echocardiogram (TEE). It is TEE that primarily requires general anesthesia, adding significant risk to the old and frail patient population on whom this type of repair procedure is typically performed on.

For at least these aforementioned reasons, there is an ongoing need for:

a) Simpler device with fewer components: alternative and/or additional methods, devices, and systems for tissue fixation that may provide beneficial elasticity and durability of the flexing components without increasing the safety and manufacturing risks associated with numerous and complex components.

b) Lock-less device: a need for a simpler device to eliminate procedural risks related to locking of the device and the risks associated with failure of locking mechanisms post deployment.

c) Elastic and resilient device: a need for a device that gently cinches the annulus (or leaflets) while preserving some natural expansion and contraction of the annulus (or leaflets).

d) Smaller catheter size/profile: considering that most patients undergoing these treatments may be old and frail with multiple comorbidities, there is also a need to make the delivery device much smaller than 24Fr to lower risk associated with vascular access.

e) Multiple device sizes: to provide such methods, devices, and systems in a manner that does not limit the tissue gripping ability of the fixation device. For example, to address small coaptation length and/or frail leaflets there may be a need for the ability to grasp beyond the coapting region of the leaflet, while conforming to the shape and length of the leaflets.

f) Tangle free design: The current market leader MitraClip® fixation device has barbs exposed on both sides of the tissue grabbing feature. Tendons, tissue and device delivery mechanisms can become trapped by such exposed barbs. Hence, there is a need to improve on the safety of bailout and repositioning of the device that further mitigates the risk of tissue or delivery mechanisms getting stuck in the device during the procedure.

g) Visualization: there is need for improved visualization and feedback to perform the procedure safely and successfully with minimal trauma to the patient.

h) Local anesthesia: An ideal procedure would be under local anesthesia without the use of general anesthesia. This mitigates higher risks associated with general anesthesia. At least some of the embodiments disclosed below are directed toward these objectives.

2. Description of the Background Art

Minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorne. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorne. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorne. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorne. Surg. 63:1805-1806. Tri-cuspid valve annuloplasty is described in McCarthy and Cos-grove (1997) Ann. Thorne. Surg. 64:267-268; Tager et al. (1998) Am. J. Cardiol. 81:1013-1016; and Abe et al. (1989) Ann. Thorne. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484,579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

MitraClip® fixation devices, systems and methods of engaging tissue are described in U.S. Pat. Nos. 8,057,493; 7,226,467.

U.S. Patent Publication No. 2015/0257883 is of particular relevance to the present application where the lead inventor is the inventor herein.

SUMMARY OF THE INVENTION

This invention provides devices, systems and methods for tissue approximation and repair at treatment sites. The devices, systems and methods of the invention will find use in a variety of therapeutic procedures, including endovascular, minimally-invasive, and open surgical procedures, and can be used in various anatomical regions, including the abdomen, thorax, cardiovascular system, heart, intestinal tract, stomach, urinary tract, bladder, lung, and other organs, vessels, and tissues. The invention is particularly useful in those procedures requiring minimally-invasive or endovascular access to remote tissue locations, particularly those in which the instruments utilized must negotiate long, narrow, and tortuous pathways to the treatment site. In addition, many of the devices and systems of the invention are adapted to be reversible and removable from the patient at any point without interference with or trauma to internal tissues.

In preferred embodiments, the devices, systems and methods of the invention are adapted for fixation of tissue at a treatment site. Exemplary tissue fixation applications include cardiac valve repair, septal defect repair, vascular ligation and clamping, laceration repair and wound closure, but the invention may find use in a wide variety of tissue approximation and repair procedures. In a particularly preferred embodiment, the devices, systems and methods of the invention are adapted for repair of cardiac valves, and particularly the mitral valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. In addition, the position of the leaflets may vary in diseased mitral valves depending upon the type and degree of disease, such as calcification, prolapse or flail. These types of diseases can result in one leaflet being more mobile than the other (e.g. more difficult to capture), and therefore more difficult to grasp symmetrically in the same grasp with the other leaflet. The features of the present invention allow the fixation devices to be adapted to meet the challenges of unpredictable target tissue geometry, as well as providing a more robust grasp on the tissue once it is captured. Additionally, the invention optionally incorporates visualization techniques to enable the device placement procedure to be performed without the use of general anesthesia.

The devices, systems and methods of the invention are centered on variety of devices which may be used individually or in a variety of combinations to form interventional systems. In preferred embodiments, the interventional system includes a multi-catheter guiding system, a delivery catheter and an interventional device. Each of these components will be discussed herein.

In an exemplary embodiment, the invention provides a fixation device having a pair of outer arms (or fixation elements), each outer arm having a free end and an engagement surface for engaging the tissue, wherein the outer arms are moveable between a first position for capturing the tissue and a second position for fixing the tissue. Preferably, the engagement surfaces are spaced apart in the first position and are closer together and generally face toward each other in the second position. The fixation device is preferably delivered to a target location in a patient's body by a delivery catheter having an elongated shaft, a proximal end and a distal end, the delivery catheter being configured to be positioned at the target location from a remote access point such as a vascular puncture or cut-down or a surgical penetration. In a preferred embodiment, the target location is a valve in the heart.

A particular advantage of the present invention is its ability to coapt the leaflets of the mitral valve (or any other tissue with which it is used) in a parallel or vertical relationship. In other words, the leaflets may be captured, drawn together and fixed such that their proximal upstream surfaces are disposed parallel to each other and generally aligned with the direction of flow through the valve at the point of coaptation. In some embodiments of the fixation device, the use of sufficiently rigid outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a parallel or vertical relationship while grasping alongside the anatomical contours of the leaflets. In other words, the leaflets may be captured, drawn together, and fixed such that their proximal upstream surfaces are disposed parallel to each other and generally aligned with the direction of flow through the valve at the point of coaptation, while additionally grasping alongside the anatomical contours away from the coaptation. In some embodiments of the fixation device, the use of sufficiently flexible outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

A particular advantage of the present invention is its ability to coapt the leaflets of the mitral valve (or any other tissue with which it is used) in a close anatomical relationship of the leaflet shape, while grasping alongside the anatomical contours of the leaflets. In other words, the leaflets may be captured, drawn together and fixed such that their natural anatomical shape is retained. In some embodiments of the fixation device, the use of sufficiently flexible outer arms, highly frictional and compressive inner arms and a passive closure mechanism enables the leaflets to be grasped in a spaced-apart relationship and then drawn together in a coapted relationship while keeping the leaflets vertical (aligned with blood flow) to achieve the optimal coapted configuration.

The fixation device is preferably delivered with the outer arms in a delivery position configured to minimize the profile of the device. When approaching the mitral valve from the atrial side, some embodiments of the fixation device allow the device to be delivered with the free ends of the outer arms pointing in a generally proximal direction forming an angle of less than about 90°, preferably less than about 20°, relative to the longitudinal axis of the delivery device shaft. In this position the engagement surfaces are facing generally toward each other, being disposed at an angle of less than about 180°, and preferably less than about 40°, relative to each other. For ventricular approaches, in the delivery position the free ends of the outer arms are pointing in a generally distal direction and form an angle of less than about 90°, preferably less than about 20° relative to the longitudinal axis of the delivery device shaft. In this position, the engagement surfaces are facing generally toward each other, usually being disposed at an angle of less than about 180°, and preferably less than about 90°, relative to each other. Alternatively, in some ventricular approaches, it may be preferred to have the free ends of the fixation elements pointing in a generally proximal direction and the engagement surfaces facing away from each other in the delivery position.

In order to provide for the reversibility and removability of the devices and systems of the invention, the leaflets are lifted off the sufficiently flexible outer arms using sutures or wires to effectively mimic inversion of the outer arms, which minimizes entanglement and interferences with surrounding tissues should the device be desired to be withdrawn. In mitral repair applications, this is particularly important due to the presence of chordae tendineae, valve leaflets and other tissues with which devices may become entangled. For approaches from the atrial side of the mitral valve (in the mimicked inverted position), the sutures or wires are disposed at an angle of more than about 180°, and preferably more than 270° relative to each other. For ventricular approaches to the valve in the mimicked inverted position, the suture or wires will be pointing in a distal direction relative to the catheter shaft and the engagement surfaces will be facing generally toward each other, usually being disposed at an angle of less than about 180°, and preferably less than 90° relative to each other.

In the open position the engagement surfaces of the outer arms preferably form an angle of up to 1800 relative to each other so as to maximize the area in which to capture the valve leaflets or other target tissue. The outer arms are preferably flexible to a closed position in which the engagement surfaces engage each other or form an angle as small as 0° relative to each other. The outer arms are configured to be flexible and left permanently in any of various positions while exerting a compressive force opposing the inner arms to allow for the fixation of tissues of various thickness, geometry, and spacing.

A particular advantage of this invention is that both outer and inner arms are sufficiently superelastic and flexible to exert persistent and gentle (atraumatic) opposing forces on the tissue, while allowing for small movements to conform with a) anatomical shape of the leaflet and b) physiological forces on the leaflets.

A particular advantage of this invention is that both outer and inner arms are sufficiently superelastic, resilient and flexible, which on capturing the leaflets in an open state to closed final configuration, exert a gentle therapeutic cinch on the annulus (directly or via the leaflets), while preserving some natural expansion during diastole and aiding natural contraction of the annulus during systole. This gentle cinch on the annulus potentially promotes positive remodeling of the annulus, especially in dilated annulus of enlarged hearts. Additionally, it better preserves the natural annulus expansion during diastole, which in turn increases the orifice area of the valve for enhanced blood flow from atria to ventricles during diastole. While the valve clips of the present invention will be less traumatic and more flexible than the MitraClip® device, the clips will still be sufficiently robust to firmly clamp and immobilize the valve leaflets so that they can function as desired to improve flow control through the treated valve.

Another particular advantage of this invention is that the frictional elements (barbs) are placed medially along the long axis of the arm body and confined by continuous and solid side surface. Unlike in the MitraClip® device, the barbs are not exposed along the sides. This is advantageous as it significantly reduces the risk of entanglement of chordae tendineae, valve leaflets and other tissues with which devices may become entangled. Further, this feature reduces the risk of entanglement or sutures or wires or other such delivery catheter elements that may potentially come in contact with the fixation device.

In a preferred embodiment, the fixation device of the invention will further include at least one inner arm (or gripping element) and one outer arm (or coapting element). Each inner arm and outer arm will be movable relative to each other and configured to capture tissue between the inner arm and the engagement surface of the outer arm. Preferably, the outer arms and inner arms are independently movable but in some embodiments may be movable with the same mechanism. The inner arm may be preferably biased toward the engagement surface of the fixation element and vice-versa to provide a compressive force against tissue captured there between.

In another aspect, the invention provides a fixation device comprising of a coupling member configured for coupling to a catheter and a pair of outer arms connected to the coupling member, in which each outer arm holds an engagement surface in order to grasp the tissue.

In some applications such as the repair of the mitral valve, the fixation device is adapted to be detached from the delivery catheter and left permanently in the patient. In such applications, it is often desirable to promote tissue growth around the fixation device. For this purpose, some or all of the components of the fixation device are preferably covered with a covering or coating to promote tissue growth. In one embodiment, a biocompatible fabric cover is positioned over the outer arms and/or the inner arms. The cover may optionally be impregnated or coated with various therapeutic agents, including tissue growth promoters, anti-biotics, anti-clotting, blood thinning, and other agents. Alternatively or in addition, some or all of the fixation element and/or covering may be comprised of a bioerodable, biodegradable, or bioabsorbable material so that it may degrade or be absorbed by the body after the repaired tissues have grown together.

In some applications such as the repair of the mitral valve, the fixation device is adapted to be detached from the delivery catheter and left temporarily in the patient. In such applications, it is often desirable to not promote tissue growth around the fixation device, while providing a hemocompatible and biocompatible surface. For this purpose, some or all of the components of the fixation device are preferably covered with a covering or coating to promote hemocompatibility without tissue growth. In one embodiment, a biocompatible fabric cover is positioned over the outer arms and/or the inner arms. The cover may optionally be impregnated or coated with various therapeutic agents, including tissue growth inhibitors, anti-biotics, anti-clotting, blood thinning, and other agents. Alternatively or in addition, some or all of the fixation element and/or covering may be comprised of a bioerodable, biodegradable, or bioabsorbable material so that it may degrade or be absorbed by the body after the repaired tissues have grown together.

The outer arms and inner arms will be configured to provide sufficiently high retention force so that the fixation device remains securely fastened to the target tissue throughout the cardiac cycle. At the same time, the distal and inner arms will be configured to minimize any acute trauma to the tissue engaged by them. This allows the fixation device to be removed from the tissue after initial application without creating clinically significant injury to the tissue. In order to enhance retention without creating significant trauma, the inner arms and/or the outer arms may have friction-enhancing features on their surfaces that engage the target tissue. Such friction-enhancing features may include barbs, bumps, grooves, openings, channels, surface roughening, coverings, and coatings, among others. Preferably, the friction-enhancing features will be configured to increase the retention force of the distal and inner arms on the tissue, while not leaving significant injury or scarring if the device is removed.

The outer and inner arms may further have a shape and flexibility to maximize retention force and minimize trauma to the target tissue. In a preferred embodiment, the engagement surfaces of the outer arms have a concave shape configured to allow the inner arms, along with the target tissue, to be nested or recessed within the outer arms. This increases the surface area of the tissue engaged by the outer arms and creates a geometry of tissue engagement that has a higher retention force than a planar engagement surface. To minimize trauma, the longitudinal edges as well as the free ends of the outer arms are preferably curved outwardly away from the engagement surface so that these edges present a rounded surface against the target tissue. The outer arms and/or the inner arms may also be flexible so that they deflect to some degree in response to forces against the tissue engaged thereby, reducing the chances that the tissue will tear or be damaged in response to such forces.

The fixation device will include an actuation mechanism for moving the outer arms between the open, closed, and inverted positions. A variety of actuation mechanisms may be used. In an exemplary embodiment, sutures or strings or wires or levers that are controllable by the delivery system handles by the user, may be used to raise and lower the outer or inner arms to capture the leaflets.

The fixation device of the invention preferably includes a coupling member that is detachably connectable to the delivery catheter. The coupling member may have various constructions, but in an exemplary embodiment comprises a flexible rod, wire or stylet of sufficient tensile strength, that coaxially and slidably extends from the handle to the fixation device. When the user(s) desires, they manipulate the handle safety release mechanisms that allows for retraction of the coupling member. This in turns cause the coupling member to slide out of the engaging elements between the delivery system and the fixation device. The delivery catheter will be configured to detachably connect to both the coupling member and fixation device. In one embodiment, the delivery catheter has a round hole through an elongated member and a rod/wire/stylet slidably disposed in the hole of the elongated member. The junction of the coupling member, elongated member and the fixation device comprises a mating surface which may have a variety of shapes including sigmoid curves or angular or planar surfaces. The rod/wire/stylet extends from the delivery catheter through the axial channel in the outer member to maintain its connection with the fixation device. The rod/wire/stylet may be connected by various connection structures, including threaded connections. Detachment and retraction of the rod/wire/stylet back into the delivery catheter decouples the delivery catheter to allow deployment of the fixation device.

The delivery device of the present invention delivers interventional devices to a target location with a body. Such interventional devices particularly include fixation devices or any devices which approximate tissue, such as valve leaflets. The delivery devices and systems direct the interventional device to the target location through a minimally invasive approach, such as through the patient's vasculature, and provide for manipulation of the interventional device at the target location, such as to approximate tissue. Optionally, the delivery devices and systems may provide for decoupling of the interventional device, allowing the interventional device to be left behind as an implant.

In an aspect of the present invention, a delivery device is provided comprising an elongated flexible shaft preferably suitable for introduction through tortuous passageways in the body. The elongated shaft has a proximal end, a distal end, and a main lumen there between. Included in the delivery device is at least one elongated body, particularly at least one flexible tubular guide, extending through the main lumen. In some embodiments, the tubular guide is fixed to the shaft near the proximal end and near the distal end and is unconstrained relative to the shaft there between so as to be laterally moveable within the main lumen. Alternatively, the tubular guide may be unconstrained in only a distal portion of the shaft so as to provide greater flexibility of that portion.

In some embodiments, two flexible tubular guides are present. However, three, four, five, six or more flexible guides may alternatively be present. The tubular guides may be comprised of any suitable material which provides lateral flexibility while providing strength under compression, such as a metallic or polymeric coil. In addition, other elongated bodies may be present, such as cylindrical rods, wires, sutures, stylets to provide additional tensile strength. In some embodiments, the main lumen is occupied by fluid so that the elongated bodies are surrounded by such fluid.

In an aspect of the present invention, the delivery device includes an actuation element movably disposed in at least one of the flexible tubular guides and extending between the proximal and distal ends. The actuation element is adapted for coupling with a movable component of an interventional element so that movement of the actuation element moves the movable element. Such an interventional element is typically removably coupled to the distal end of the shaft.

The moveable component may have any of a variety of functions, including grasping, approximating, cutting, ablating, stapling or otherwise engaging tissue. In one embodiment, the moveable component provides for approximation of tissue, such as coaptation of valve leaflets. In preferred embodiments, the interventional element has first and second tissue engaging elements adapted for engaging tissue there between. Thus, in these embodiments, the actuation element is used to move the tissue engaging elements to engage the tissue. Further, in some embodiments, the shaft and interventional element are adapted for positioning through a blood vessel.

In an aspect of the present invention, a system is provided for approximating tissue at a treatment site. In some embodiments, the system comprises an elongated flexible shaft having a proximal end, a distal end, a main lumen there between, and at least one flexible tubular guide extending through the main lumen. Again, in preferred embodiments the tubular guide is fixed to the shaft near the proximal end and near the distal end and is unconstrained in at least a portion of the main lumen there between so as to be laterally movable within the main lumen. In some embodiments, the system also includes an actuation element movably disposed in the tubular guide, and an approximation device coupled to the distal end of the shaft, the approximation device having first and second engaging elements for engaging tissue there between, at least one of the engaging elements being movable and coupled to the actuation element.

The delivery device of the invention is adapted to allow the user to deliver the fixation device to the target site from a remote access point (whether through endovascular or surgical approaches), align the device with the target tissue, and to selectively close, open, invert, lock, or unlock the outer arm. The delivery device will preferably have a highly flexible, kink resistant, torsionally stiff shaft with minimal elongation and high tensile and compressive strength. The delivery device will also have the movable components and associated actuators used to move the arms between the lowered and raised positions, to move the arms into engagement with the target tissue, and to detach the outer arm from the delivery catheter. A plurality of tubular guides, preferably in the form of metallic coils or plastic tubes or multi-lumen tubes preferably with low coefficient of friction, extend through the inner lumen of the shaft and are fixed to the shaft near its proximal and distal ends but are unrestrained there between, providing a highly flexible and kink-resistant construction. Lines for actuating the inner arms and the unlocking mechanism of the fixation device extend through these tubular guides and are detachably coupled to the inner arm and unlocking mechanisms.

The delivery catheter may additionally include a tether comprised of a suture or wire or flexible rod that is detachably coupled to a portion of the fixation device for purposes of retrieval of the device following detachment from the delivery catheter. The tether may be a separate flexible filament extending from the delivery catheter to the fixation device, but alternatively may be a line coupled to either the unlocking mechanism or the inner arm and used also for actuating those components. In either case, the tether will be detachable from the fixation device so that it may be detached once the device has been deployed successfully.

In some embodiments, the delivery device further includes an actuation element movably disposed in one of the at least one flexible tubular guide, and a fixation device coupled to the distal end of the shaft and adapted for positioning in the chamber of the heart. Typically, the fixation device is releasably coupled to the shaft. In some embodiments, the fixation device has at least one inner arm and at least one outer arm adapted to engage a valve leaflet between them, wherein at least one of the inner and outer arms is movable and coupled to the actuation element. Alternatively or in addition, the actuation element comprises a flexible line, such as a lock line or an inner arm line or an outer arm line.

The system may further comprise first and second flexible tubular guides extending from the proximal end to the distal end through the main lumen. The first and second tubular guides are preferably fixed to the shaft near the proximal end and near the distal end and are unconstrained in at least a portion of the main lumen there between so as to be laterally movable within the main lumen. Further, the first movable element extends through the first tubular guide and the second movable element is movably disposed in the second tubular guide.

The system may also further comprise an actuator handle connected to the proximal end of the shaft, the actuator handle having a body and first, second and third actuation elements movably coupled thereto, the first, second and third actuation elements being coupled to the first, second and third movable elements.

Systems of the invention may additionally include a guide that facilitates introduction and navigation of the delivery catheter and fixation device to the target location. The guide is preferably tubular with a channel extending between its proximal and distal ends in which the delivery catheter and fixation device may be slidably positioned. The distal end of the guide is steerable, usually being deflectable about at least one axis, and preferably about two axes. The guide will have a size, material, flexibility and other characteristics suitable for the application in which it is being used. For mitral valve repair, the guide is preferably configured to be introduced in a femoral vein and advanced through the inferior vena cava into the heart, across a penetration in the interatrial septum, and into alignment with the mitral valve in the left atrium.

Alternatively, the guide may be configured to be introduced in a brachiocepalic or axillary or carotid vein (neck/shoulder access) and advanced through the superior vena cava into the heart, across a penetration in the interatrial septum, and into alignment with the mitral valve in the left atrium.

Alternatively, the guide may be configured for introduction in a femoral, axillary, or brachiocephalic artery and advancement through the aorta and aortic valve into the ventricle where it is steered into alignment with the mitral valve. In a further alternative, the guide may be configured for introduction through a puncture or incision in the chest wall and through an incision in the wall of the heart to approach the mitral valve.

In an exemplary embodiment, the guide comprises a multi-catheter guiding system which has two components, including an inner tubular member or inner guide catheter and an outer tubular member or outer guide catheter. The outer tubular member has a distal end deflectable about an axis. The inner tubular member has a distal end deflectable about an additional axis. Further, the distal end of inner tubular member may be angularly deflectable. Mobility in additional directions and about additional axes may optionally be provided.

The invention further provides methods of performing therapeutic interventions at a tissue site. In one embodiment, the method includes the steps of advancing an interventional tool having a proximal end, a distal end and a fixation device near the distal end to a location within a patient's body, wherein the fixation device includes a pair of outer arms each having a free end and an engagement surface; moving the outer arms to an open position wherein the free ends are spaced apart; positioning the outer arms such that the engagement surfaces engage tissue at the tissue site; and detaching the fixation device from the interventional tool. Preferably, the method further includes the step of decoupling the leaflets off the outer arms, to allow for bailout or re-attempt the procedure.

At least one embodiment of the present disclosure relates to a tissue gripping device including: a base section; and a first outer arm having a free end and a fixed end that is coupled to the base, and a first inner arm having a free end and a fixed end that is coupled to the base, followed by second outer arm and a second inner arm that are similarly coupled to the base in a modular fashion; wherein, the tissue is grasped between the distal and proximal arms; and wherein the distal and proximal arms are formed of an elastic-plastic material or rheological material or shape-memory material configured to exhibit superelasticity in a physiological environment, and the base is formed of elastic/plastic material or shape-memory material configured to exhibit superelasticity in a physiological environment.

At least one embodiment of the present disclosure relates to a tissue fixation system configured for intravascular delivery and for use in joining mitral valve (or tricuspid valve) tissue during treatment of the mitral valve (or tricuspid valve), the system including: the tissue gripping device including: a base section; and a first outer arm having a free end and a fixed end that is coupled to the base, and a first proximal arm having a free end and a fixed end that is coupled to the base, followed by second outer arm and a second proximal arm that are similarly coupled to the base in a modular fashion; wherein, the tissue is grasped between the distal and proximal arms; and wherein the distal and proximal arms are formed of a shape-memory material configured to exhibit superelasticity in a physiological environment, and the base is formed of elastic/plastic material or shape-memory material configured to exhibit superelasticity in a physiological environment.

At least one embodiment of the inner or outer arms have barbs that are encompassed within smooth outside edges on either side of the barbs, to limit the risk of tissue or delivery mechanisms getting stuck in the barbs; and wherein, the barbs are formed of an elastic-plastic material or rheological material or shape-memory material configured to exhibit superelasticity in a physiological environment.

In at least one embodiment of the fixation device delivery system, there is a provision for a standalone or a dedicated probe built into the delivery system that incorporates an active ultrasonic probe; wherein the probe is retractable, translatable, rotatable, steerable, and has at least one or more features such as and not limited to: 2-D imaging, Doppler, 3-D imaging, 4-D imaging, multimodality imaging features, with or without the use of ultrasonic markers or contrast agents; in-synchronization or out of synchronization to limit physiological artifacts (caused by for example and not limited to heart-beat and breathing); to help assist, identify, and navigate pre-procedure, during procedure, and post-procedure.

At least one embodiment of the fixation device delivery system, there is a provision for a standalone or a dedicated probe built into the delivery system that incorporates an passive ultrasonic probe; wherein the probe is retractable, translatable, rotatable, steerable, and has at least one or more multimodality imaging enabling features such as and not limited to: 2-D imaging, Doppler, 3-D imaging, 4-D imaging, with or without the use of ultrasonic markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active Optical Coherence Tomography (OCT) probe; wherein the probe is retractable, translatable, rotatable, steerable, and has at least one or more enabling features such as and not limited to: 2-D imaging, Doppler, 3-D imaging, 4-D imaging, multimodality imaging features, with or without the use of OCT markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive Optical Coherence Tomography (OCT) probe; wherein the probe is retractable, translatable, rotatable, steerable, and has at least one or more features such as and not limited to: 2-D imaging, Doppler, 3-D imaging, 4-D imaging, multimodality imaging features, with or without the use of OCT markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active optical camera based imaging system housed inside a balloon; wherein, the balloon may be filled with fluid (gas or liquid) that allows for visualization when the balloon is either in contact or vicinity of the target tissue; wherein the probe is retractable, translatable, rotatable, steerable, and has at least one or more enabling features such as and not limited to: 2-D imaging, Doppler, 3-D imaging, 4-D imaging, multimodality imaging features, with or without the use of optical markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive optical camera based imaging system (for example and not limited to optical fiber imaging system) housed inside a balloon; wherein, the balloon may be filled with fluid (gas or liquid) that allows for visualization when the balloon is either in contact or vicinity of the target tissue; wherein the probe is retractable, translatable, rotatable, steerable, and has at least one or more features such as and not limited to: 2-D imaging, Doppler, 3-D imaging, 4-D imaging, multimodality imaging features, with or without the use of optical markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an active sensor/transducer/actuator system; wherein the probe is retractable, translatable, rotatable, steerable, and has at least one or more enabling features such as and not limited to: pressure, strain, stress, ECG, EMG, 2-D imaging, Doppler, 3-D imaging, 4-D imaging, multimodality imaging features, with or without the use of markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for a standalone or a dedicated probe built into the delivery system that incorporates an passive sensor/transducer/actuator system (for example and not limited to RFID based systems); wherein the probe is retractable, translatable, rotatable, steerable, and has at least one or more enabling features such as and not limited to: pressure, strain, stress, ECG, EMG, 2-D imaging, Doppler, 3-D imaging, 4-D imaging, multimodality sensing/transducing features, with or without the use of markers or contrast agents; in-synchronization or out of synchronization to limit physiological artifacts (caused by for example and not limited to heart-beat and breathing); to help assist, identify, and navigate pre-procedure, and/or during procedure, and/or post-procedure.

At least one embodiment of the fixation device delivery system, there is a provision for the device to coated to enhance biocompatibility and tissue interface, wherein, the coating maybe with metals (for example and not limited to: titanium, tantalum, gold, platinum, iridium, tungsten or their combination), and/or ceramics, and/or polymers for example and not limited to: fluoropolymers (PTFE, PFA, FEP, ECTFE, ETFE), parylene, polyester, PER, polypropylene, PEEK, PVDF, HDPE, LDPE, UHMWPE, Phosphorylcholine, hydroxyapatite, CaP, THV, biodegradable materials (polylactic acid, polyglycolic acid), Bioerodible materials such as polydioxanone, poly(ε-caprolactone), polyanhydride, poly(ortho ester), copoly(ether-ester), polyamide, polylactone, poly(propylene fumarate) and/or their combinations; wherein, these coatings may be hydrophilic or hydrophobic.

At least one embodiment of the fixation device delivery system, there is a provision for the device to coated to enhance biocompatibility and tissue interface, wherein, the coating may be with metals (for example and not limited to: titanium, tantalum, gold, platinum, iridium, tungsten or their combination), and/or ceramics, and/or polymers for example and not limited to: fluoropolymers (PTFE, PFA, FEP, ECTFE, ETFE), parylene, polyester, PER, polypropylene, PEEK, PVDF, HDPE, LDPE, UHMWPE, Phosphorylcholine, hydroxyapatite, CaP, THV, and biodegradable materials (polylactic acid, polyglycolic acid), Bioerodible materials such as polydioxanone, poly(ε-caprolactone), polyanhydride, poly(ortho ester), copoly(ether-ester), polyamide, polylactone, poly(propylene fumarate) and/or their combinations; wherein, these coatings may be hydrophilic or hydrophobic.

At least one embodiment of the present disclosure relates to a method of gripping tissue, the method including: positioning a tissue gripping device near a target tissue, the tissue gripping device being formed from a shape-memory material and including a base section and a first arm and a second arm, each arm having a first end coupled to the base section and a free end extending from the base section, the first and second arms being disposed opposite one another; and moving the tissue gripping device from a pre-deployed configuration toward a deployed configuration, the first and second arms being configured to resiliently flex toward a relaxed configuration in a distal direction as the tissue gripping device is moved from a pre-deployed configuration toward a deployed configuration.

At least one embodiment of the present disclosure relates to a method of manufacturing a tissue gripping device, the method including: cutting one or more structural features into a strip or sheet stock material of a shape-memory alloy, the one or more structural features including a plurality of slotted recesses disposed at one or more sites away from side edges of the stock material; and heat shape setting one or more bend features into the stock material.

In a first specific aspect, a valve clip according to the present invention comprises a hub, a first pair of leaf capture arms comprising a first inner arm and a first outer arm coupled to the hub, and a second pair of leaf capture inner arms comprising a second inner arm and a second outer arm coupled to the hub. The outer and inner arms are configured to be biased apart to create a leaf capture space therebetween and to self-close over a valve leaflet when unbiased after the leaflet has been captured The hub is typically configured to be removably attached to a deployment shaft, and at least some of the leaf capture arms are typically formed as a leaf spring. An outer surface of each inner arm is positioned adjacent to an inner surface of each outer arm, and an inferior end of each arm is coupled to the hub, with the inferior ends of each inner arms typically being superior to the inferior ends of each outer arm. The terms "inferior" and "superior" are defined relevant to the patient anatomy in which the valve clip will be implanted. For example, when implanted in a mitral valve, superior refers to the side of the clip facing the atrium while inferior refers to the side of the clip facing the ventricle. When planted in a vein, superior will refer to the upstream direction while inferior refers to the downstream direction.

The spring-biased outer and inner arms are configured to be "opened" to initially capture a pair of valve leaflets and to self-close over the valve leaflets after the leaflets have been captured. By "opened" it is meant that the individual arms can be bent or biased so that they are moved out of their normal, unbiased configurations, i.e. when they are free from deformation due to the application of an external force.

In particular embodiments, at least some of the outer and inner arms of the valve clip are formed as "leaf springs" with a resilient base and a less-resilient (more rigid) valve-grasping element. The resilient base will usually provide most or all of the resilience or bending capability for the leaf spring structure and is configured so that it may be attached directly or indirectly to the hub and. The valve-grasping element (for example and not limited to barbs), in contrast, will usually experience little or no bending when deployed over the leaflets of a target valve. Usually all of the outer and inner arms will have the configurations as described.

In other specific embodiments, the adjacent outer and inner arms of the valve clip will have generally congruent shapes. By generally congruent, it is meant that the outer and inner arms will have the same or complementary shapes and will be able to "nest" when attached to the hub and in their unbiased configurations. There will usually be a small distance or gap between the inferior surfaces of the inner arms and the superior surfaces of the outer arms, typically from 0 mm to 6 mm, preferably from 0.5 mm to 2.5 mm, when the outer and inner arms are in their unbiased configurations to accommodate the valve leaflets therebetween when the valve leaflets are captured by the valve clip. These gap values accommodate a typical thickness of a single leaflet between inner and outer arms. In other specific embodiments wherein two or more leaflets are captured between the pair of arms, these gap values may be increased two or three fold. While there can be a minimum gap, the spring-bias of the arms may be sufficient by itself to accommodate a full range of leaflet wall thicknesses.

In a first illustrated embodiment, the valve-grasping elements of the valve clip will diverge from a common axis through the hub to form a V-shape when the outer and inner arms are unbiased. Typically, the resilient base is curved and the valve-grasping elements are straight in both the outer and inner arms. Still more typically, the resilient bases on the outer arms have an S-shaped curve selected to offset or separate the superior surfaces of the outer arms from inferior surfaces of the inner arms in order to provide the gap or separation to accommodate the valve leaflets as described previously. Alternatively, a spacer may be used in between the arms to create space to accommodate the leaflets.

In other illustrated embodiments, the valve-grasping elements are parallel to a common axis through the when the outer and inner arms are unbiased. In such instances the inner arms are generally straight but the bases of the outer arms have a curve selected to separate superior surfaces of the outer arms from inferior surfaces of the inner arms in order to accommodate the valve leaflets there between.

In a second aspect of the present invention, a system for delivering valve clip to a heart or venous valve will comprise any of the valve clip designs described above or elsewhere or herein. The systems will further comprise a deployment shaft configured to be removably attached to the hub of the valve clip.

In particular embodiments of the systems of the present invention, the deployment shaft may extend from the hub in a superior direction along an axis of symmetry through the hub and between right-side outer and inner arms and left-side outer and inner arms.

In exemplary embodiments, the system further comprises a steerable deployment catheter removably or fixedly coupled to the deployment shaft. In some instances, an inferior end of the deployment shaft is configured to be coupled to the steerable deployment catheter. In other instances, a superior end of the deployment shaft is configured to be coupled to the steerable deployment catheter.

In still further embodiments, the steerable catheter may include an imaging component to allow real-time visualization of an implantation procedure. The imaging component may include one or more of optical imaging components, ultrasound imaging components, OCT imaging components, or the like. The imaging components will be positioned on the deployment catheter so that they may visualize both the target anatomical valve and the valve clip as the valve clip is being manipulated for implantation over the valve leaflets. In still further embodiments, the delivery system and/or the fixation device may contain radiopaque and/or echogenic mechanical indicators that change position when the leaflets are fully inserted thereby allowing the user to confirm the insertion of the leaflets by visualizing via conventional fluoroscopic or ultrasound imaging.

In still other embodiments of the systems of the present inventions, the steerable catheters will include mechanisms for selectively applying biasing forces to the outer and/or inner arms of the valve clip in order to open the arms in order to create the gap or space for receiving and capturing the valve leaflets. In the illustrated embodiments, a first set of tethers may be positioned on or through the delivery catheter and coupled to the outer arms so that the tethers may be tensioned to selectively bias the outer arms into a valve leaflet capture position. A second set of tethers will usually be positioned through the delivery catheter and coupled to the inner arms and configured to selectively bias the inner arms into a valve leaflet capture position. Both sets of tethers will typically be further configured to selectively unbias the outer arms and the inner arms so that the outer and inner arms are allowed to self-close toward and over the valve leaflets in order to immobilize the leaflets for treatment of any of the conditions described herein and above.

In in a third specific aspect, the present invention provides methods for clipping an anatomical valve to immobilize the leaflets of that valve for treating a variety of conditions. For example, the leaflets of a mitral valve may be clipped in order to treat mitral valve regurgitation. In another example, the leaflets of a venous valve may be clipped in order to treat venous insufficiency.

The methods of the present invention comprise advancing a valve clip having a pair of outer arms and a pair of inner arms to a location adjacent to the target anatomical valve. At least one of (1) the pair of outer arms and (2) the pair of inner arms is biased to open a valve leaflets capture space or gap between adjacent outer and inner arms. The valve clip is then positioned so that one valve leaflet is located or captured in the gap or space between the left outer and inner arms another valve leaflet is positioned in the gap or space between the right outer and inner arms. The valve leaflets may then be immobilized by releasing a biasing force or tension on the at least one pair of outer or inner arms to that the left outer and inner arms and the right outer and inner arms self-close over the valve leaflets, thus securing the leaflets together.

In particular embodiments of the methods of the present invention, both the pair of outer arms and the pair of inner arms will be initially biased in order to effect opening of the valve leaflet capture gaps or spaces therebetween. Biasing is typically accomplished by drawing on tethers attached to at least one of the pair of outer and inner arms, typically with separate tether structures attached to each pair of outer and inner arms. The tethers may be tensioned in order to bias the outer and inner arms so that they move away from each other to create the valve leaflet capture gap or space therebetween. After the outer and inner arms have been biased open and the valve leaflets captured, tension on the tethers may be released so that the out and inner arms self-close over the valve leaflets.

As an alternative to the use of tethers, biasing may comprise advancing a pair of posts or other engagement members against at least one pair of the outer and inner arms. The posts may engage at least the two lower arms or at least the two upper arms to selectively open the lower and upper arms into a valve leaflet capture position. In some instances, the posts may engage an upper surface of each outer arm such that advancing the posts in an inferior direction opens the outer arms relative to the inner arms. The inner arms may optionally be configured to remain stationary as the posts are advanced. In other instances, the posts may engage a lower surface of each inner arm such that advancing the posts in a superior direction opens the inner arms relative to the outer arms. The outer arms may optionally be configured to remain stationary as the posts are advanced.

In other embodiments of the methods herein, positioning the valve clip comprises manipulating a delivery catheter where the valve clip is releasably attached to a distal end of the delivery catheter. Positioning may further comprise observing the anatomical valve and the valve clip by observing the mechanical valve position indicators (as described above) and/or using an imaging component on the delivery catheter as the valve clip is being positioned.

A particular advantage of this invention is multiple sizes and shapes of the fixation device. The fixation device can be configured attach to a small section of the leaflet (the where the leaflets coapt together form a parallel seal) or in a preferred embodiment, a larger section that includes the parallel coapted section as well as curved contoured section of the leaflets. Longer and contoured arms allow for easier capture of the leaflets.

Another particular advantage of this invention is that the fixation device is lock-less, by using super-elastic and sufficiently flexible inner and outer arms.

Another particular advantage of this invention is that the fixation device is made of sufficiently flexible inner and outer arms that grasp the tissue securely yet atraumatically while allowing for sufficient dynamic movement of the leaflets under physiological forces.

Another particular advantage of this invention is that inner and outer arms' frictional elements are recessed and barricaded on the sides, which mitigates risk of entanglement with chordae, tissue or delivery system.

Another particular advantage of this invention includes modular manufacturing and/or assembly of both outer and inner arms. Various shapes and sizes of inner and outer arm combinations can be interchangeably manufactured and/or assembled in a modular manner, to suit patient/user clinical treatment needs. For example, one side of the inner and outer arms may be longer to grasp larger anterior mitral valve leaflet, while a shorter inner and outer arm combination maybe used to grasp shorter posterior mitral valve leaflet.

Another particular advantage of this invention is elimination of large and increased movements of the fixation device during bailout, such as the inversion of the leaflet grasping arms. This is achieved by use of sutures, strings, or wires to lift the leaflets away from the grasping arms.

Another particular advantage of this invention is the relatively simple and compact size of the fixation device. This allows the use of smaller diameter catheters, thus making deployment less traumatic to the patient. For example, MitraClip® device uses a 24Fr outer diameter guide catheter. In a preferred embodiment, the current invention uses a 12 Fr outer diameter guide catheter.

Another particular advantage of this invention is compatibility with commercially available trans-septal introducer sheath. This is achieved by making the delivery device compatible with standard commercially available fixed or steerable trans-septal introducer sheaths. Some examples of commercial introducer sheaths sizes include and not limited to: 7 Fr, 7.5 Fr, 8 Fr, 8.5 Fr, 9 Fr, 9.5 Fr, 10 Fr, 10.5 Fr, 11 Fr, 11.5 Fr and 12 Fr internal diameters. Some examples (and not limited to these examples) of commercially available introducers are: HeartSpan Fixed Curve Braided Trans-septal Sheath and HeartSpan Steerable Sheath Introducer by Merit Medical Systems, Inc. Utah; DIREX™ and Zurpaz™ Steerable Sheath by Boston Scientific Corporation, MA and; Agilis NxT™ by St. Jude Medical, Minn.

Another advantage of this invention is the potential of performing the procedure under local anesthesia, thus eliminating the risks of general anesthesia. This is achieved by incorporating visualization techniques within or in conjunction with the delivery catheter system that replace the need for transesophageal echocardiography (TEE).

Other objects and advantages of the present invention will become apparent from the detailed description to follow, together with the accompanying drawings.

BRIEF DESCRIPTION OF THE DRAWINGS

FIG. 1A-2 illustrates the free edges of mitral valve leaflets in normal coaptation.

FIG. 1A-3 illustrates the free edges of mitral valve leaflets in regurgitative coaptation.

FIG. 1B-1 illustrates the fixation device mounted in a retrograde orientation relative to the leaflets.

FIG. 1B-2 illustrates the fixation device mounted in a preferred antegrade orientation relative to the leaflets.

FIGS. 2I-1 and 2I-2 illustrate distal segment of the introducer sheath when manipulated in a two-way steerable configuration.

FIGS. 2J through 2P and 2Q-1 through 2Q-3 depict a preferred embodiment of the exemplary 12Fr catheter based delivery system used to deploy the fixation device within the heart.

FIGS. 3A, 3B-1, 3B-2, and 3C show various exemplary embodiments of the fixation device.

FIGS. 13F-1 and 13F-2 illustrate a further embodiment of the base bracket 10 with a contoured feature that allows for easier detachment of the fixation device from the delivery catheter.

FIG. 13G-1 through 13K-2 illustrate a further embodiment of the Release Bar 16 with a post feature that allows for spreading of the outer arms of the fixation device during deployment.

DETAILED DESCRIPTION OF THE INVENTION

I. Cardiac Physiology

Figures 1, 1A:
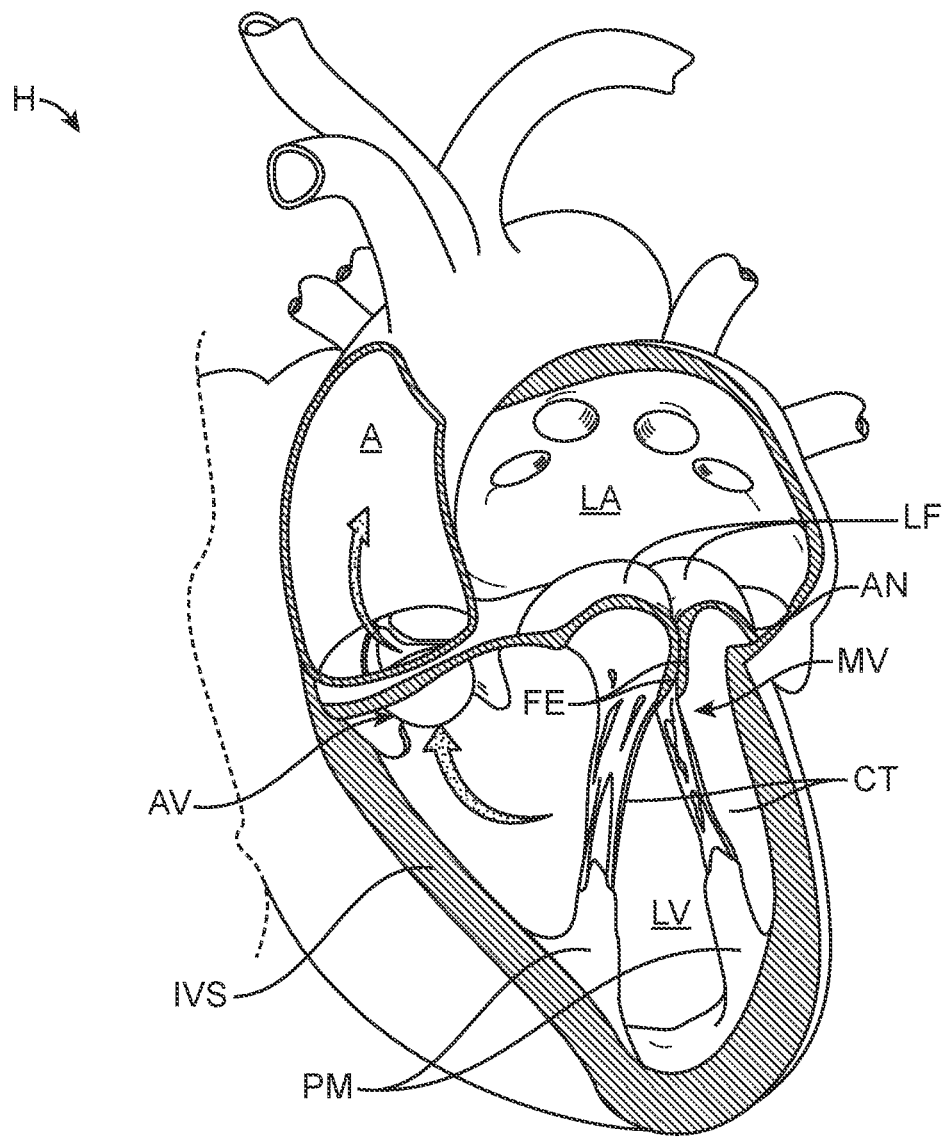
FIG. 1A-1 illustrates the left ventricle and left atrium of the human heart during systole.

The left ventricle LV of a normal heart H in systole is illustrated in FIG. 1A-1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1A-1. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and intraventricular septum IVS.

Figures 1, 1A, 2:
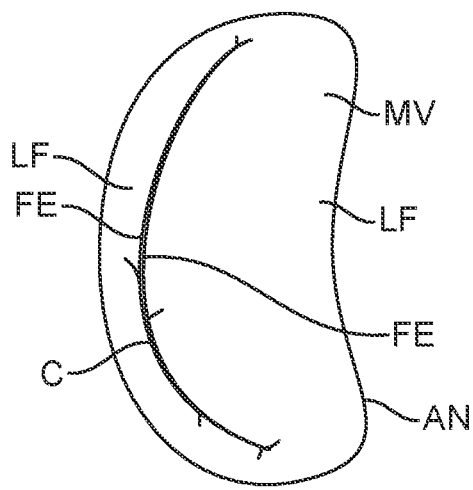
Figures 1, 1A, 2, 3:
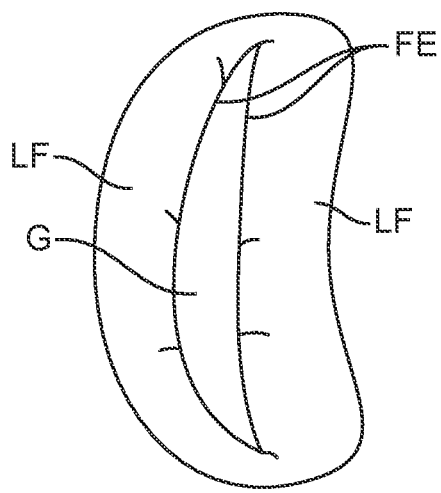

A number of structural defects in the heart can cause mitral valve regurgitation. Regurgitation occurs when the valve leaflets do not close properly allowing leakage from the ventricle into the atrium. As shown in FIG. 1A-2, the free edges of the anterior and posterior leaflets normally meet along a line of coaptation C. An example of a defect causing regurgitation is shown in FIG. 1A-3. Here an enlargement of the heart causes the mitral annulus to become enlarged, making it impossible for the free edges FE to meet during systole. This results in a gap G which allows blood to leak through the valve during ventricular systole. Ruptured or elongated chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where the left ventricle does not contract sufficiently to effect proper closure.

II. General Overview

The present invention provides methods and devices for grasping, approximating and fixating tissues such as valve leaflets to treat cardiac valve regurgitation, particularly mitral valve regurgitation. The present invention also provides features that allow repositioning and removal of the device if so desired, particularly in areas where removal may be hindered by anatomical features such as chordae CT. Such removal would allow the surgeon to re-approach the valve in a new manner if so desired.

Grasping will preferably be atraumatic providing a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic". This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. In some of these cases, grasping and fixation may be accomplished by a single device. Although a number of embodiments are provided to achieve these results, a general overview of the basic features will be presented herein. Such features are not intended to limit the scope of the invention and are presented with the aim of providing a basis for descriptions of individual embodiments presented later in the application.

The devices and methods of the invention rely upon the use of an interventional tool that is positioned near a desired treatment site and used to grasp the target tissue. In endovascular applications, the interventional tool is typically an interventional catheter. In surgical applications, the interventional tool is typically an interventional instrument. In preferred embodiments, fixation of the grasped tissue is accomplished by maintaining grasping with a portion of the interventional tool which is left behind as an implant. While the invention may have a variety of applications for tissue approximation and fixation throughout the body, it is particularly well adapted for the repair of valves, especially cardiac valves such as the mitral valve and tricuspid valve.

Figures 1, 1B:
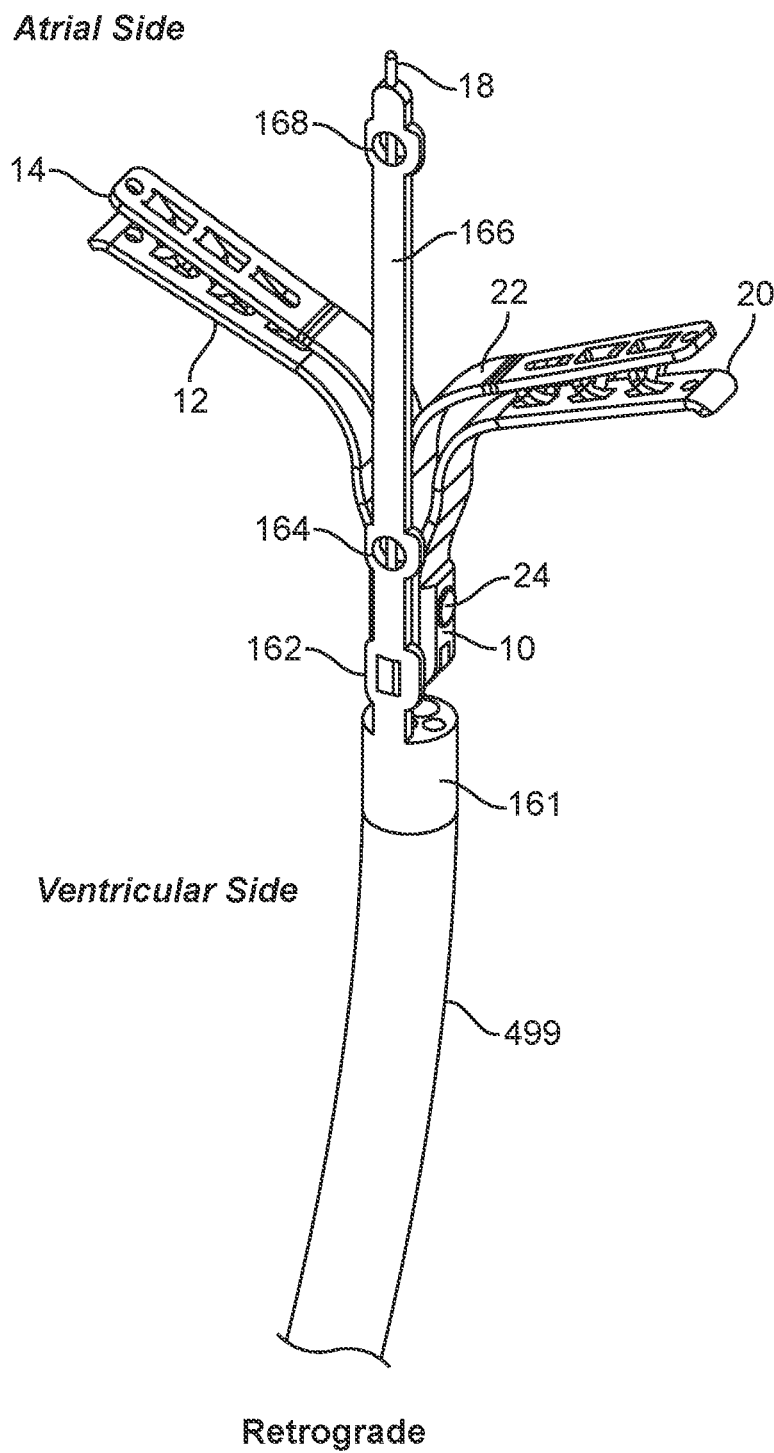
Figures 1, 1B, 2:
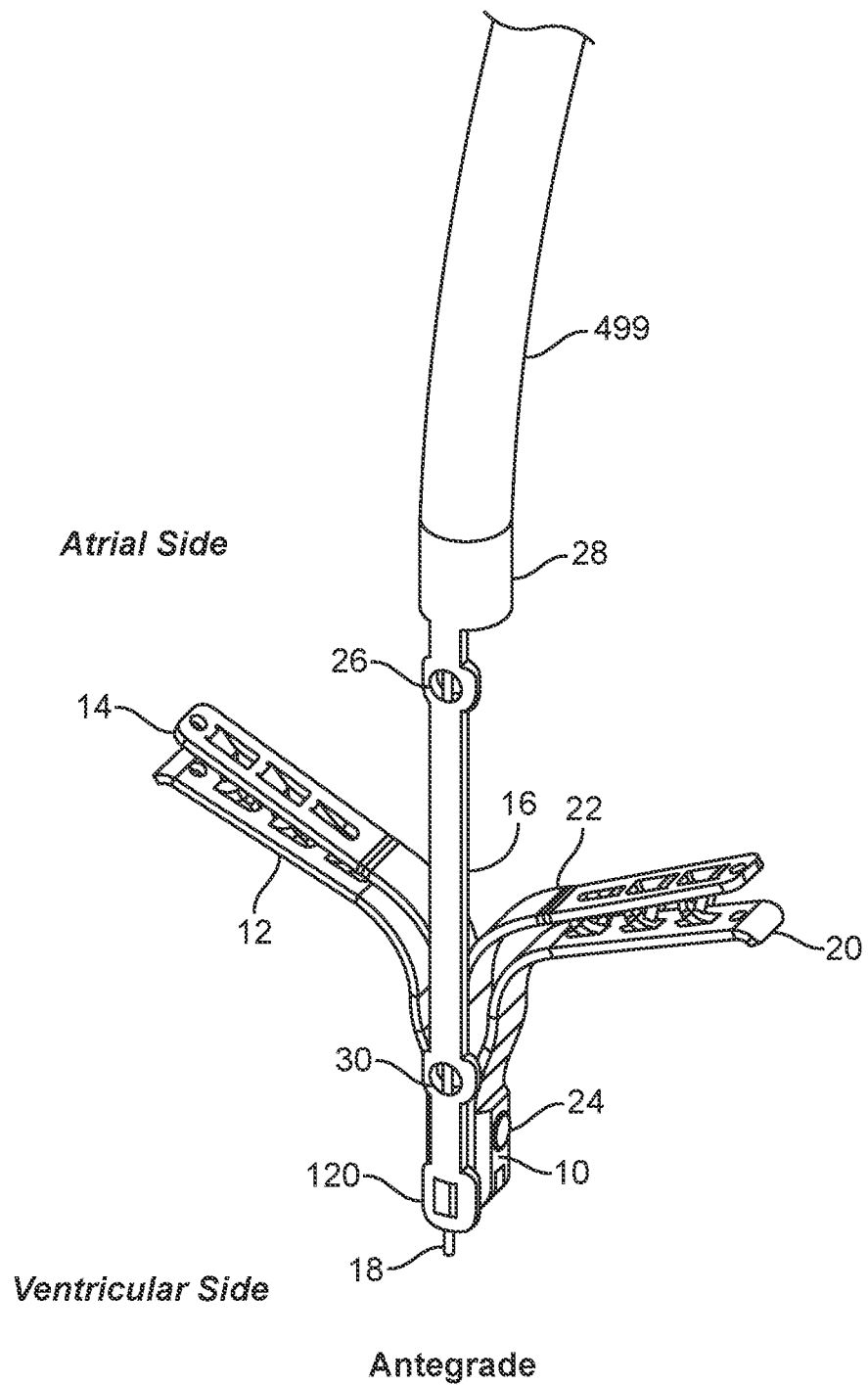

FIGS. 1B-1 and 1B-2 illustrate the fixation device in both retrograde and antegrade configurations respectfully for deployment. The fixation device is attached to the Release bar 16 or 166 which are part of the distal delivery catheter 499. In both surgical methods, the placement and position of the device remains unchanged. This may allow the fixation device to be deployed using various entry points that best suit the user need. For illustration purposes, an antegrade approach will be primarily described going forward.

FIGS. 2A through 2H depict various embodiments of the catheter-based fixation device delivery system that may be used to deploy the fixation device. Knobs 502 and 503 are used to reposition the inner (14, 22) and outer (12, 20) arms of the fixation device to (14', 22') and (12', 20') respectively and vice-versa, in order to secure the two leaflets LF (arm manipulation). Each knob may be configured to manipulate either the outer or inner arms of the device. Although only two handles systems have been exemplified, this concept may be extended to include three or more handle systems having a combination of fixed and/or steerable shaft systems.

Figure 2A:
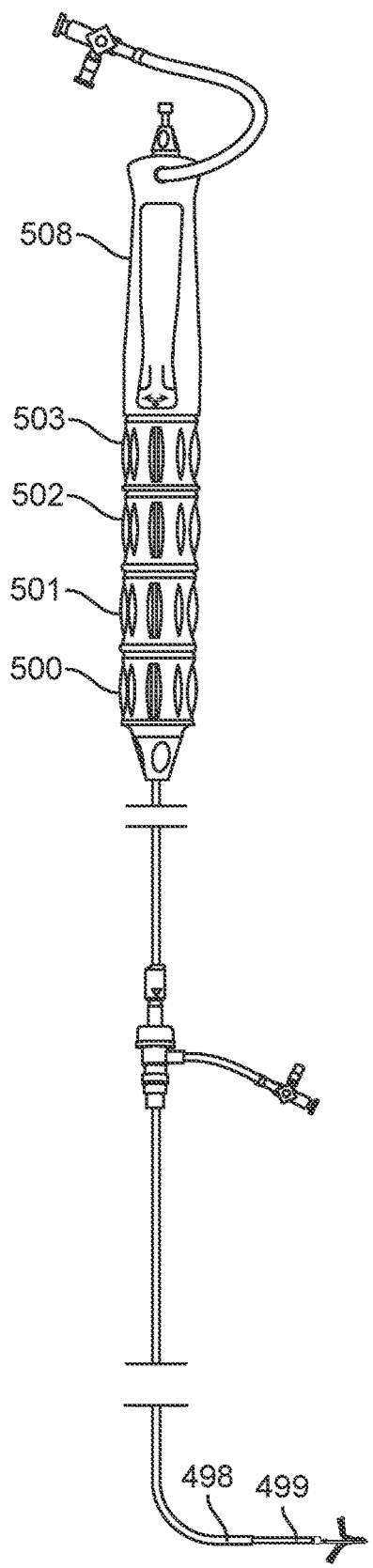
FIGS. 2A through 2H depict various embodiments of the catheter-based delivery system used to deploy the fixation device within the heart.

FIG. 2A illustrates one embodiment of the delivery system utilizing a fixed curve introducer sheath in combination with four-way steerable delivery catheter. The arm manipulation knobs 502 and 503 are configured on the same catheter handle 508. Knobs 500 and 501 are used to steer the distal delivery shaft 499 of the catheter in four directions; each knob (500 and 501) provides two-way steering. The distal introducer sheath 498 holds a fixed curve.

Figure 2B:
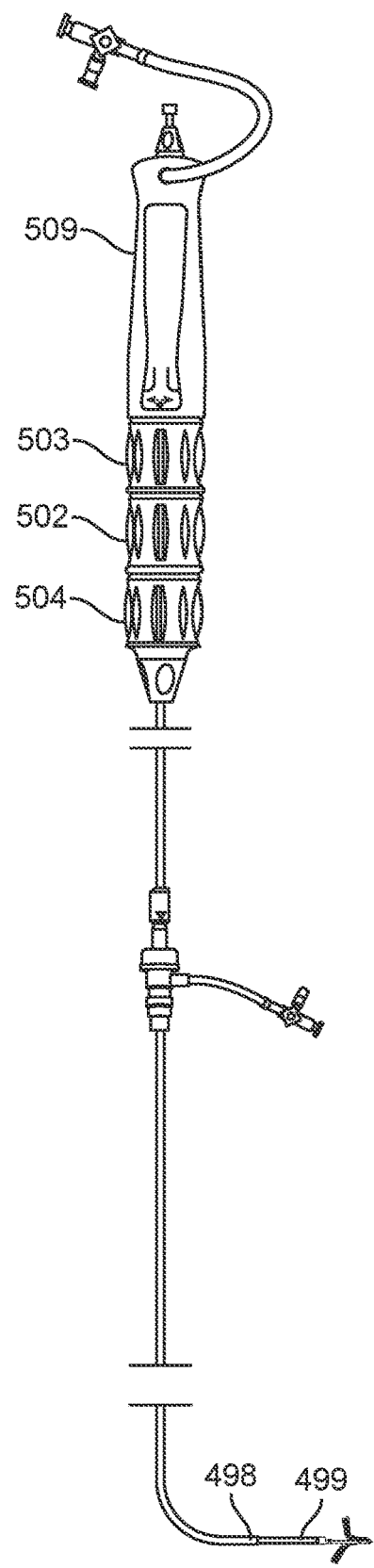

FIG. 2B illustrates a further embodiment of the delivery system utilizing a fixed curve introducer sheath in combination with two-way steerable delivery catheter. The arm manipulation knobs 502 and 503 are configured similar to catheter handle 508. Knob 504 is used to direct the distal delivery shaft 499 of the catheter in two directions to provide two-way steering. The distal introducer sheath 498 holds a fixed curve.

Figure 2C:
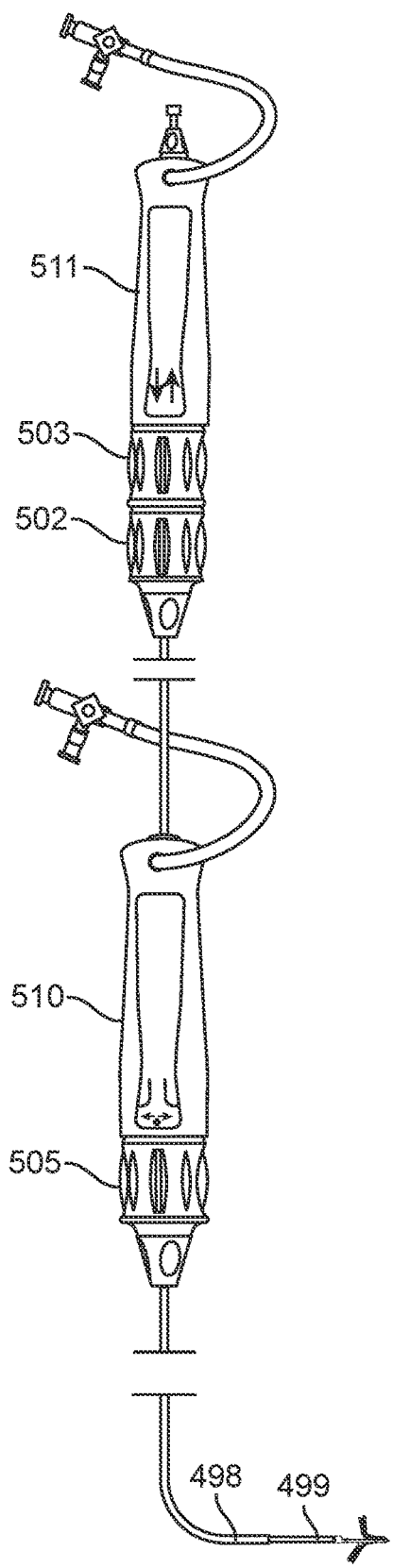

FIG. 2C illustrates a further embodiment of the delivery system utilizing a two-way steerable introducer sheath in combination with delivery catheter. The introducer sheath handle 510 houses a two-way steering knob 505 in order to manipulate and steer the distal sheath 498. This is placed in tandem with another handle 511, which in turn holds the arm manipulation knobs 502 and 503. Note, off-the shelf two-way steerable introducer sheath from Merit Medical (HeartSpan® Steerable Sheath Introducer, https://www.merit.com/cardiac-intervention/ep-and-crm/electrophysiology/heartspan-steerable-sheath-introducer/) is shown for the purpose of illustration and as an example.

Figure 2D:
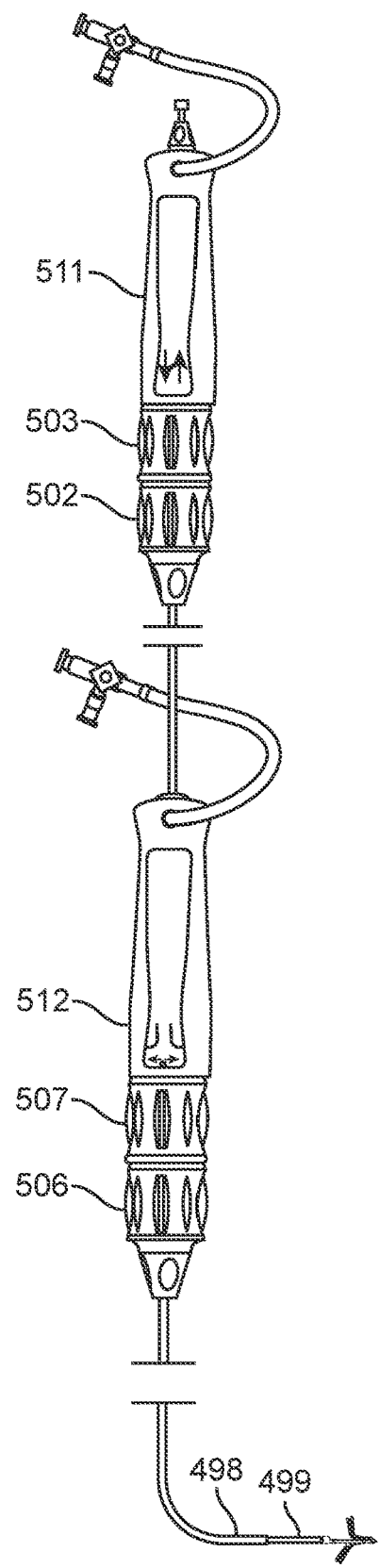

FIG. 2D illustrates a similar embodiment of the delivery system utilizing a four-way steerable introducer sheath in combination with delivery catheter. The introducer sheath handle 510 houses two 2-way steering knobs 506 and 507 in order to manipulate and steer the distal sheath 498 to provide four-way steerablility. This is placed in tandem with another handle 511, which in turn holds the arm manipulation knobs 502 and 503.

Figure 2E:
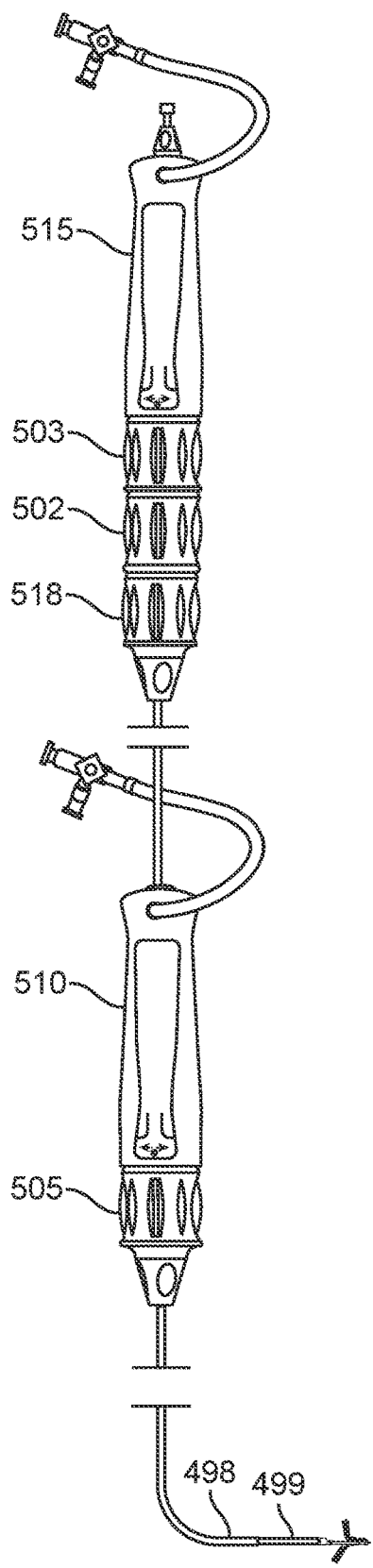

FIG. 2E illustrates a further embodiment of the delivery system utilizing a two-way steerable guide catheter in combination with a two-way steerable delivery catheter. The introducer sheath handle 510 houses a two-way steering knob 505 in order to manipulate and steer the distal sheath 498. This is placed in tandem with another handle 515, which in turn holds the arm manipulation knobs 502, 503 and additionally, knob 518 that provides two-way steering of distal delivery shaft 499. Note, an off-the-shelf two-way steerable introducer sheath from Merit Medical (HeartSpan® Steerable Sheath Introducer, (https://www.merit.com/cardiac-intervention/ep-and-crm/electrophysiology/heartspan-steerable-sheath-introducer/) is shown for the purpose of illustration and as an example.

Figure 2F:
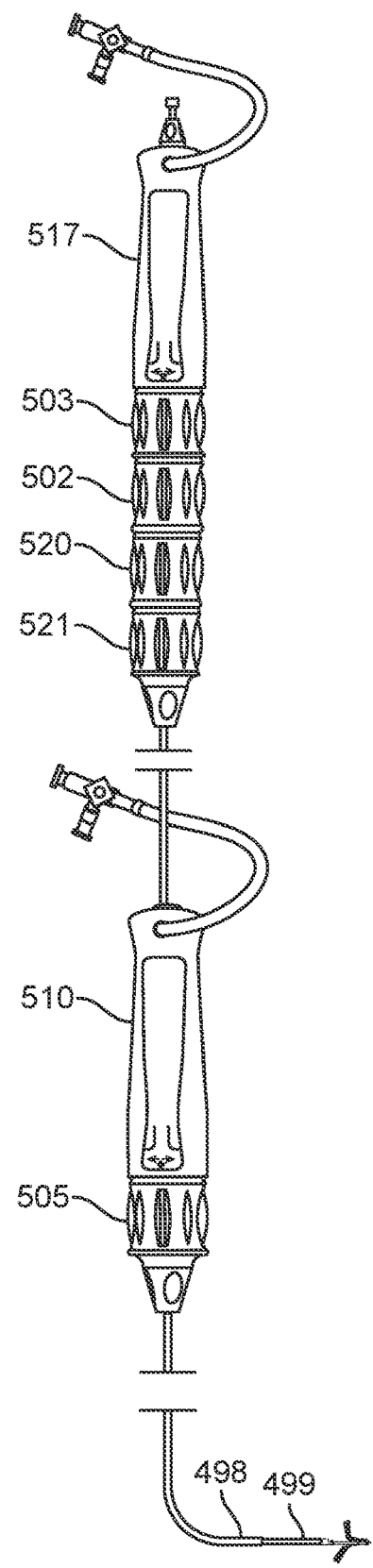

FIG. 2F illustrates a further embodiment of the delivery system utilizing a two-way steerable guide catheter in combination with a four-way steerable delivery catheter. The introducer sheath handle 510 houses a two-way steering knob 505 in order to manipulate and steer the distal sheath 498. This is placed in tandem with another handle 517, which in turn holds the arm manipulation knobs 502, 503; and additionally knobs 520 and 521 that each provide two-way steering of distal delivery shaft 499 that results in four-way steerablility. Note, an off-the shelf two-way steerable introducer sheath from Merit Medical (HeartSpan® Steerable Sheath Introducer, (https://www.merit.com/cardiac-intervention/ep-and-crm/electrophysiology/heartspan-steerable-sheath-introducer/) is shown for the purpose of illustration and as an example.

Figure 2G:
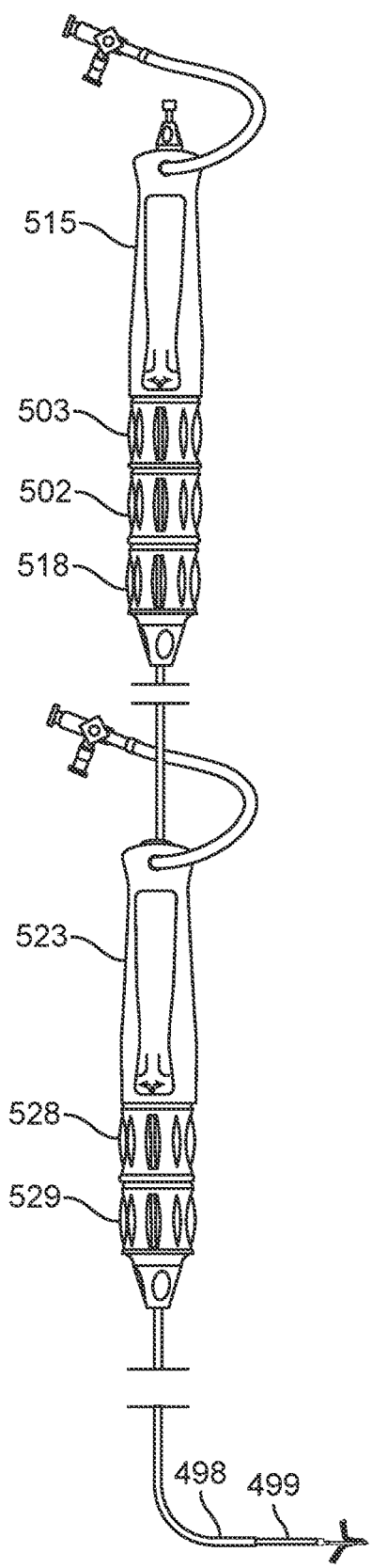

FIG. 2G illustrates a further embodiment of the delivery system utilizing a four-way steerable guide catheter in combination with a two-way steerable delivery catheter. The steerable guide catheter handle 523 houses two 2-way steering knobs 529 and 528 in order to manipulate and four-way steer the distal sheath 498. This is placed in tandem with another handle 515, which in turn holds the arm manipulation knobs 502, 503 and additionally, knob 518 that provides two-way steering of distal delivery shaft 499. In some embodiments, the knob 518 may be configured for arm manipulation in lieu of delivery catheter steerablility.

Figure 2H:
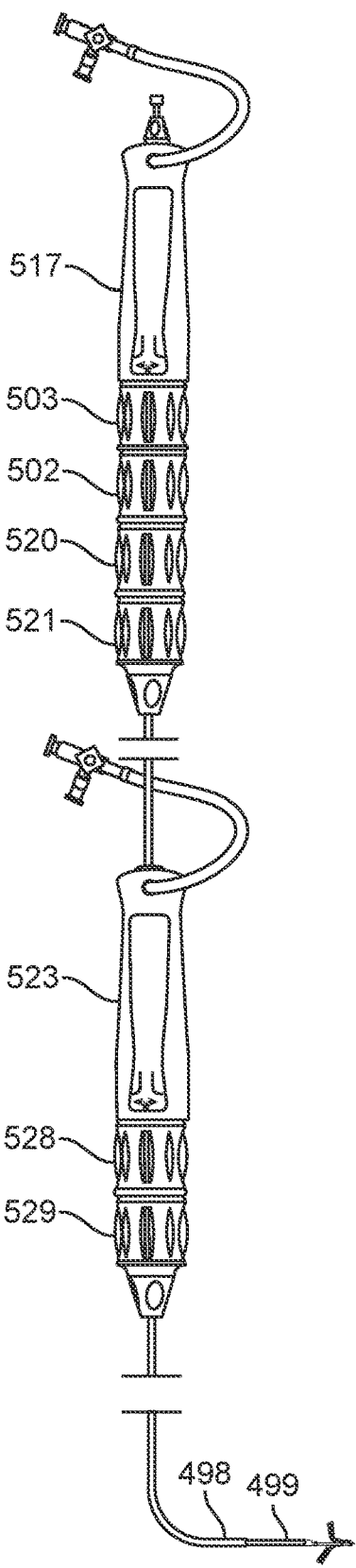

FIG. 2H illustrates a further embodiment of the delivery system utilizing a four-way steerable introducer sheath in combination with a two-way steerable delivery catheter. The introducer sheath handle 523 houses 2 two-way steering knobs 529 and 528 in order to manipulate and four-way steer the distal sheath 498. This is placed in tandem with another handle 517, which in turn holds the arm manipulation knobs 502, 503; and additionally knobs 520 and 521 that each provide two-way steering of distal delivery shaft 499 resulting in four-way steerablility.

Figures 1, 2I:
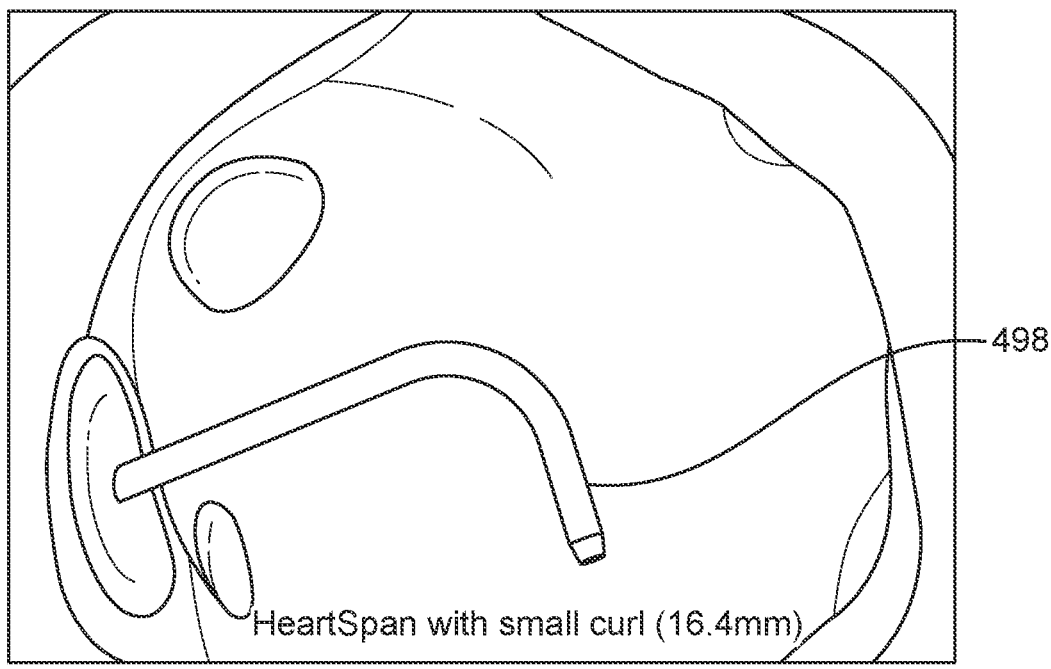
Figures 2, 2I:
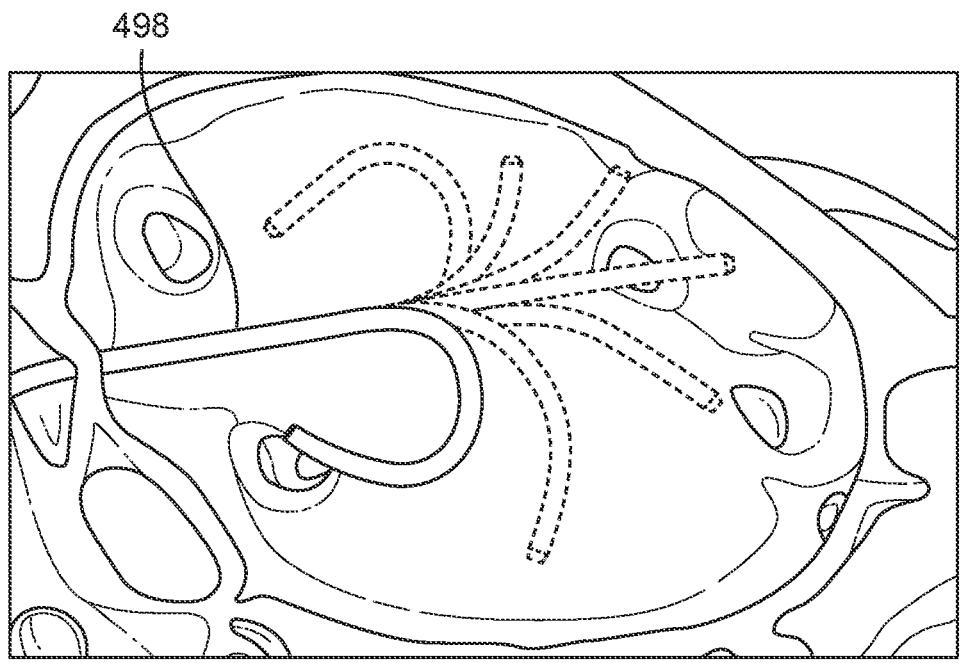

FIGS. 2I-1 and 2I-2 illustrate the movement of the distal introducer sheath 498 with two-way steering configuration.

FIGS. 2J through 2Q depict a preferred embodiment of an exemplary 12Fr custom catheter based delivery system used to deploy the fixation device within the heart.

Figure 2J:
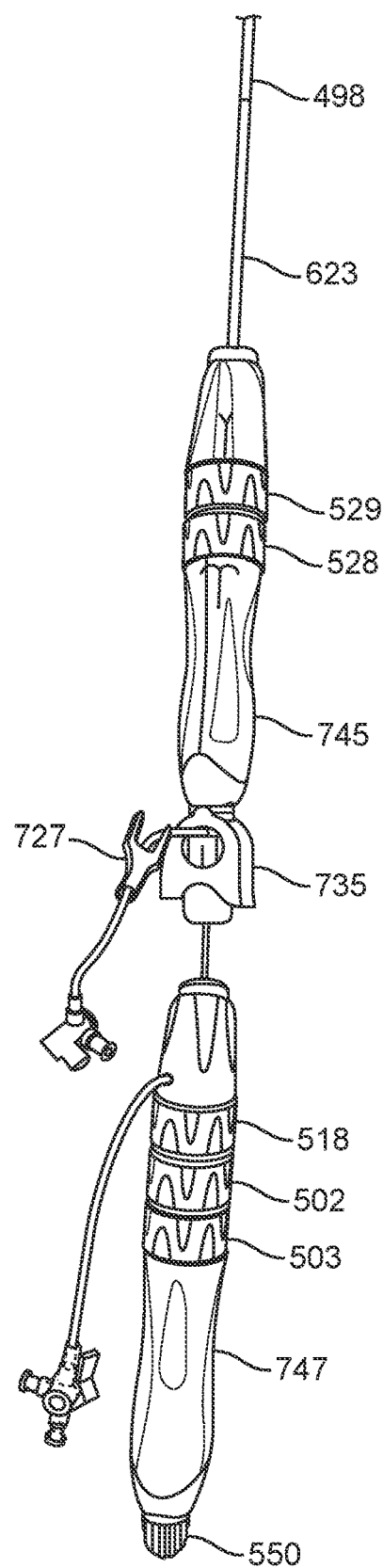

FIG. 2J illustrates a further embodiment of the exemplary 12Fr delivery system utilizing a four-way steerable guide catheter in combination with a delivery catheter, similar to FIG. 2G, however, using custom handles 745, 747. The steerable guide catheter handle 745 houses two 2-way steering knobs 529 and 528 in order to four-way steer the sheath 498. The steerable guide is placed in tandem with delivery catheter handle 747, which in turn holds the arm manipulation knobs 502, 503 and additionally, knob 518 that is configured for arm manipulation in lieu of delivery catheter steerablility. In a preferred embodiment, Knobs 502 is used to independently manipulate one inner arm, while the Knob 503 is used to independently manipulate the other inner arm. The third knob 518 is used to manipulate the two outer arms simultaneously.

Figure 2K:
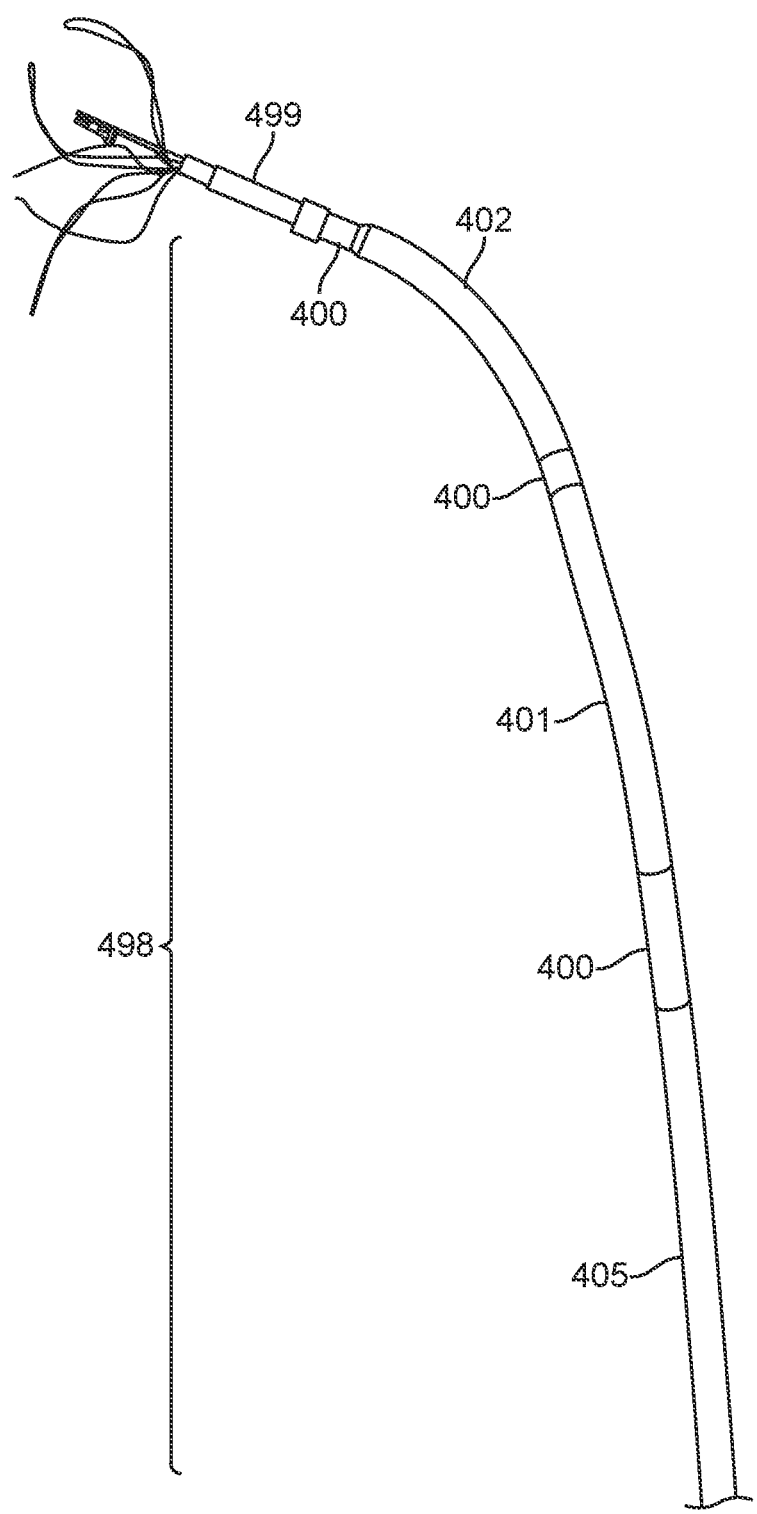

FIG. 2K shows the distal segments of the catheter system shown in FIG. 2J. As can be seen, the exemplary 9 Fr outer diameter delivery catheter shaft 499 passes through the lumen of the exemplary 12 Fr inner diameter steerable guide catheter shaft 498.

Figure 2L:
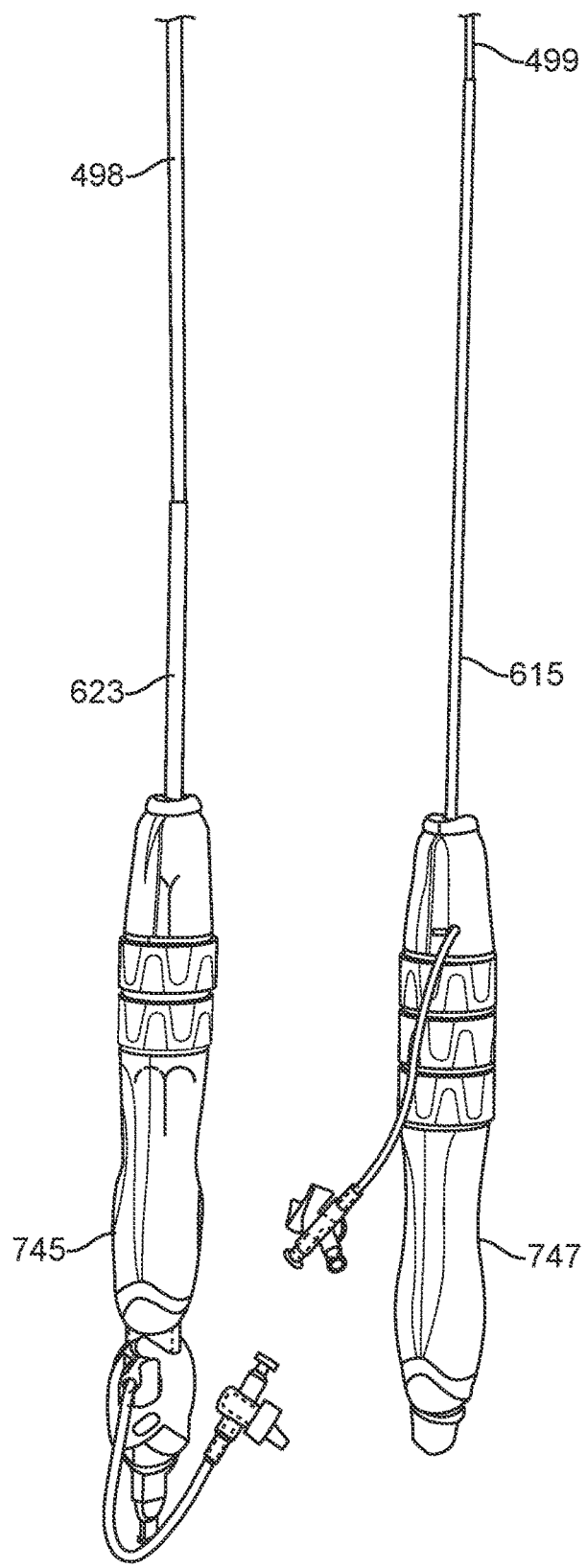

FIG. 2L shows the steerable guide and delivery catheter handles side-by-side. The exemplary stainless-steel tube 623 provides a means to support and attach the steerable guide catheter handle on to a suitable stand (not shown). While, the exemplary stainless-steel tube 615 provides a means to support and translate the delivery catheter, when inside the steerable guide handle.

Figure 2M:
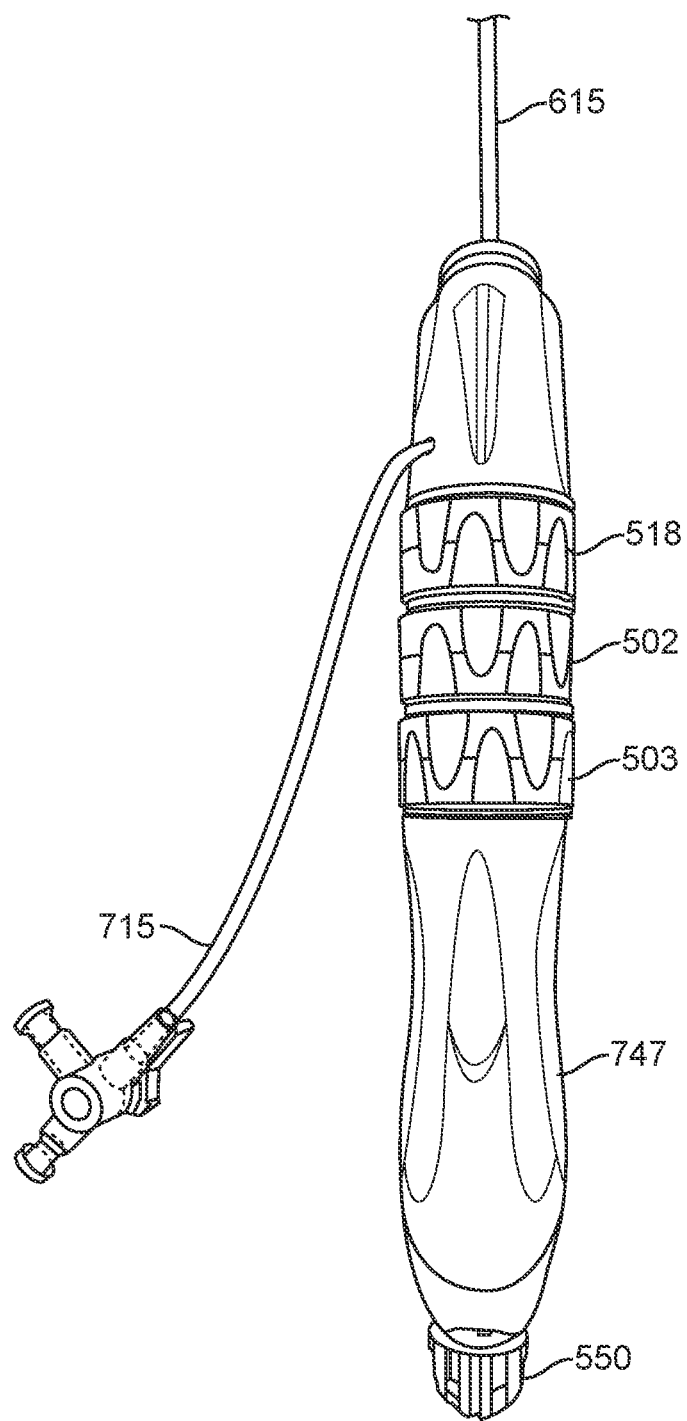

FIG. 2M shows detailed view of the delivery catheter handle with a flush port 715, which can optionally be used to measure hemodynamic pressure at the Release bar 16. In addition, figure shows exemplary quarter turn locking Release rod knob 550. The knob 550 can be used to manipulate the Release Rod 18 and thereby release/deploy the fixation element.

Figure 2N:
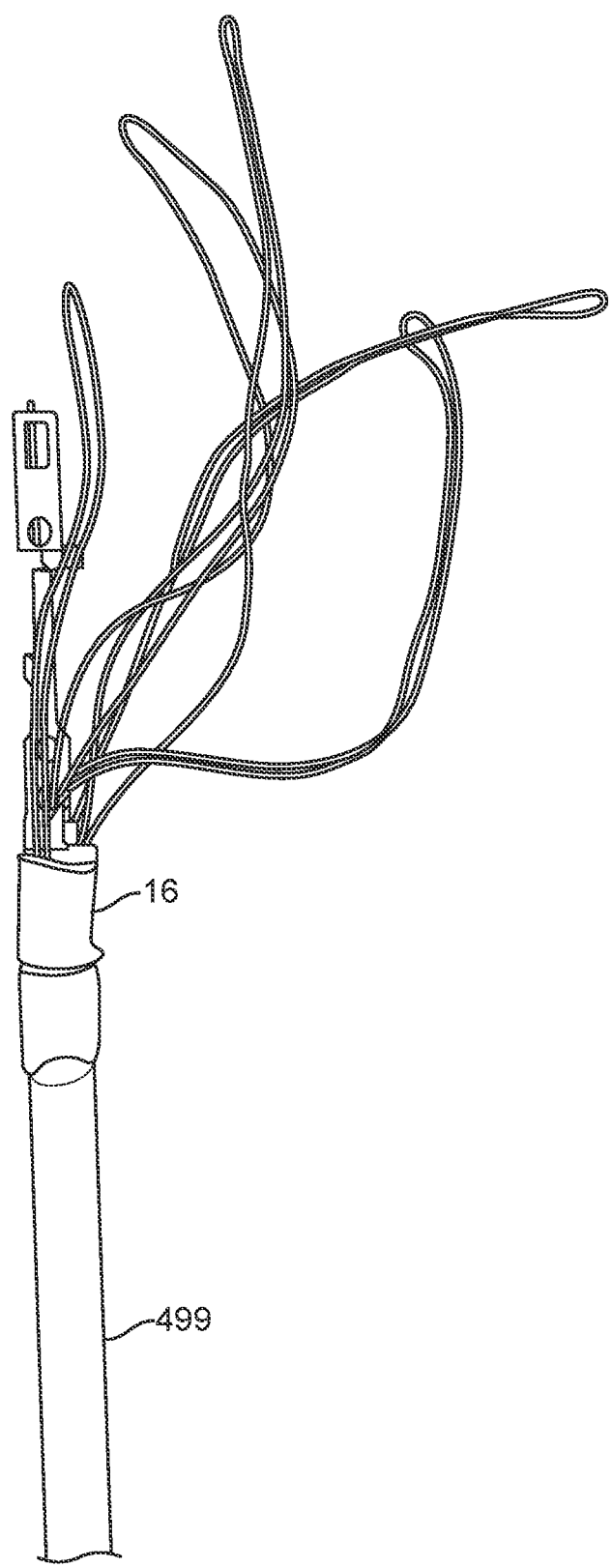

FIG. 2N shows exemplary distal segment of the custom delivery catheter.

Figure 2O:
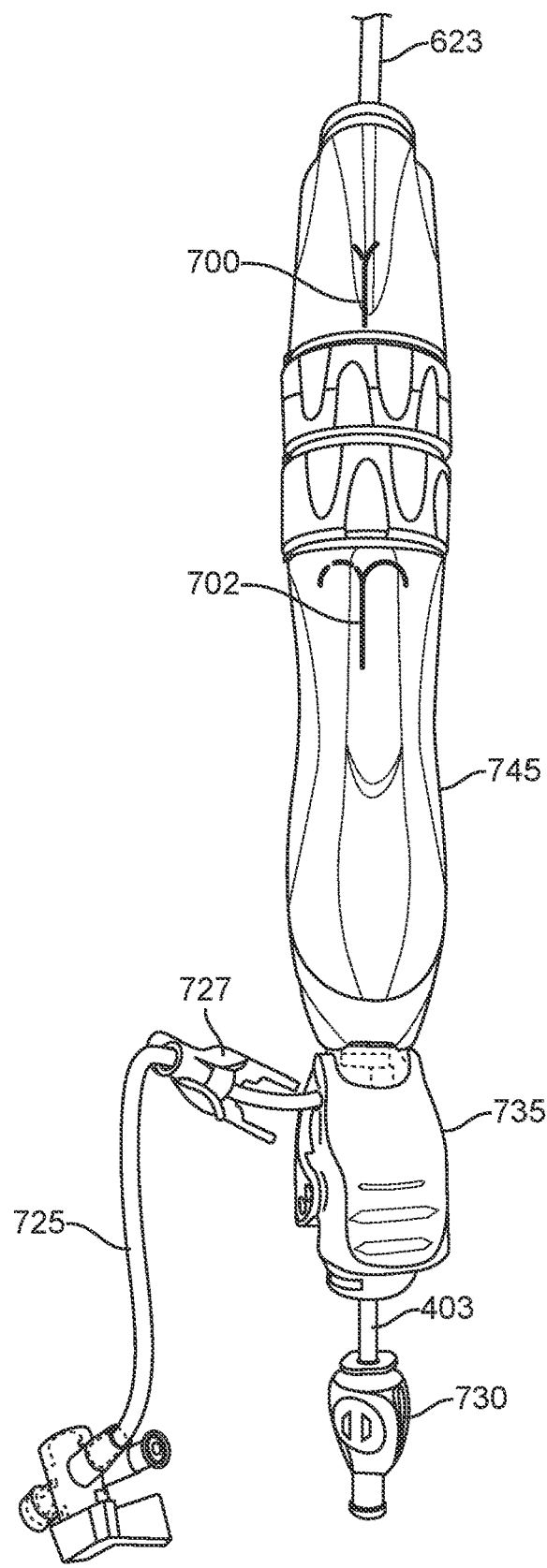

FIG. 2O shows details of the steerable guide handle 745 with dilator proximal shaft 403 and quarter turn locking dilator knob 730. In addition, the Steerable guide catheter handle consists of a lockable and pinchable hemostasis valve 735. When unlocked and not pinched by the user, the hemostasis valve collapses to tightly close on itself to provide hemostasis seal. If a dilator 403 (or delivery catheter) is present, it will then close on to the dilator 403 (or delivery catheter), wherein, in addition to providing hemostasis seal, it also constrains the motion of the dilator 403 (or delivery catheter), as shown in FIG. 2O.

Figure 2P:
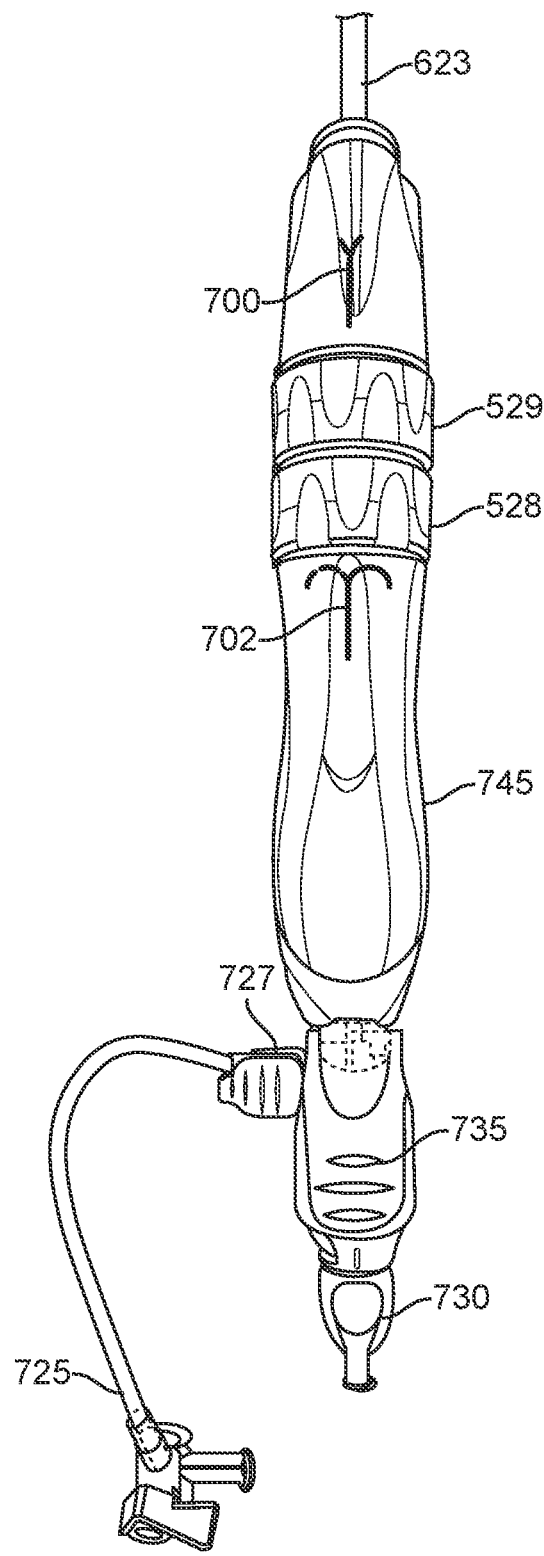

When locked using the lock 727 as shown in FIG. 2P or when pinched by user, the hemostasis valve opens to allow for free movement or passage of the dilator (or delivery catheter). The optional and exemplary labels 700 and 702 show steerability functions of the knobs 520 and 528.

FIG. 2Q-1 shows the detailed view of the distal segment of the steerable guide catheter shaft 498. The shaft 498 is wire reinforced to provide the required kink resistance, torquability and pushability. The proximal shaft 405 is relatively stiff, while the distal steerable shaft 402 is relatively flexible and the intermediate shaft 401 provides a mid-level blending stiffness. To enhance visualization under fluoroscopy, there are 3 radio-opaque markers 400.

FIG. 2Q-2 shows one of the exemplary label 702. Manipulation of the corresponding knob (528, as shown in FIGS. 2O, 2P), results in exemplary steering of distal segments 402, 401 of the steerable guide catheter shaft 498.

Figure 3A:
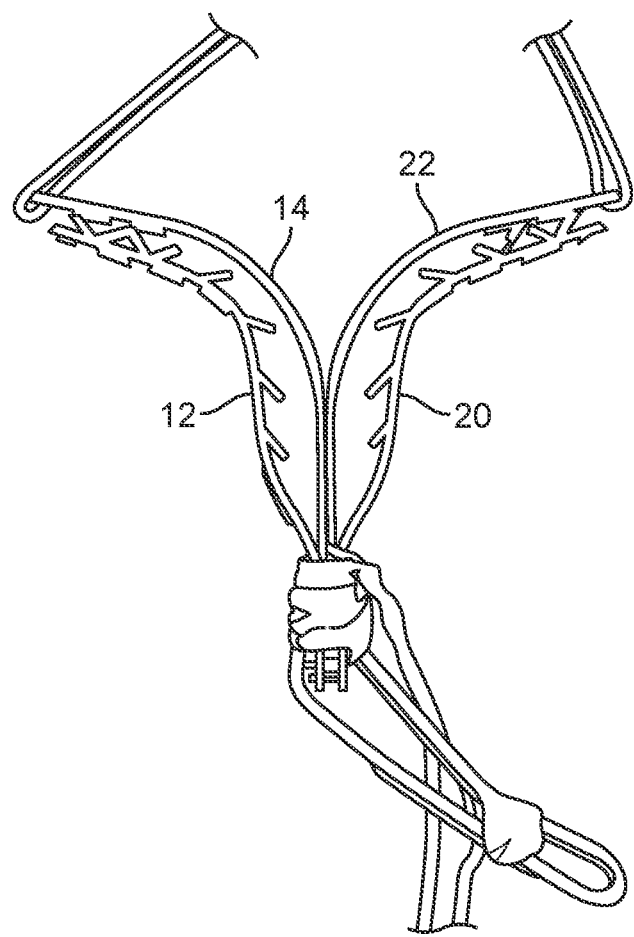
Figures 1, 3B:
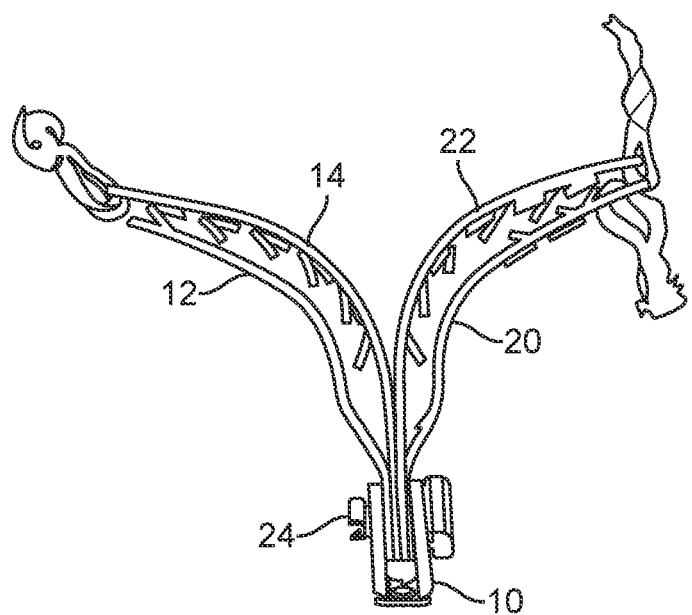
Figures 2, 3B:
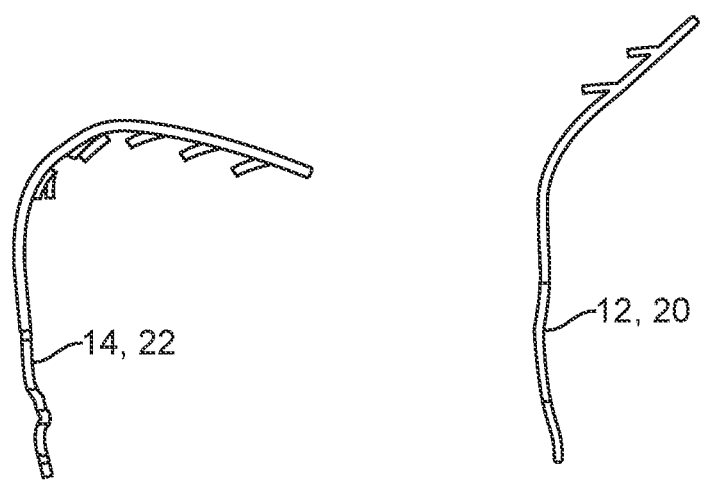
Figure 3C:
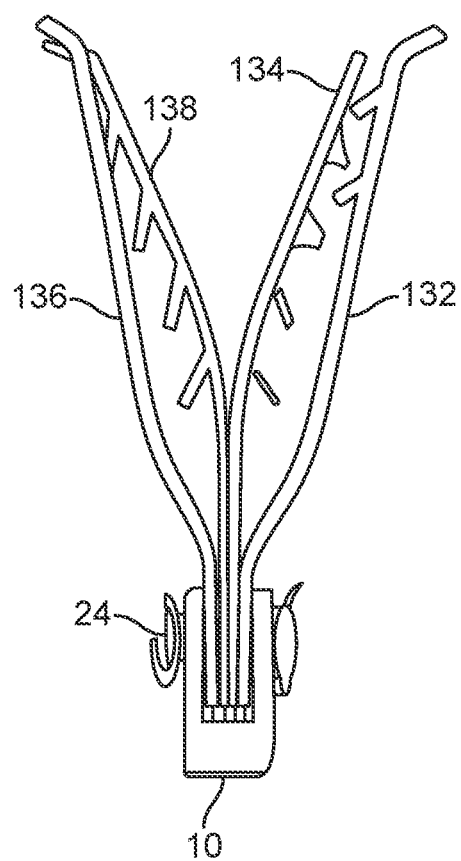

FIGS. 3A through 3C show exemplary prototypes of the fixation device types.

FIG. 3A shows the first barebone prototype, where the inner and outer arms are fastened using sutures and pin. Further, in this exemplary prototype, the inner and outer arms are contoured to allow additional grasp beyond the required coaptation of the native valve. The inner and outer arms of this exemplary prototype were made of nitinol.

FIG. 3B-1 shows yet another exemplary embodiment of the contoured fixation device. As can be seen, this is a complete prototype of the fixation device (with inner arms 14, 22, outer arms 12, 20, base bracket 10 and fastener 24. The inner and outer arms of this exemplary prototype are made of nitinol, while, the base bracket 10 and fastener 24 are made of titanium.

FIG. 3B-2 shows individual inner arms 14, 22 and outer arms 12, 20, of the fixation device shown in FIG. 3B-1. Note that the outer arms of FIGS. 3B-1 and 3B-2 have fewer barbs or frictional elements when compared to outer arms of the prototype shown in FIG. 3A or 3C.

FIG. 3C shows yet another exemplary embodiment of the contoured fixation device. As can be seen, this is a complete prototype of the fixation device (with inner arms 14, 22, outer arms 12, 20, base bracket 10 and fastener 24. The inner and outer arms of this exemplary prototype are made of nitinol, while, the base bracket 10 and fastener 24 are made of titanium. In comparison to contoured prototypes of fixation devices in FIGS. 3A and 3B-1, this prototype is designed primarily for the coapting region of the native valve.

FIGS. 4A-4F depict arm manipulation to be controlled by, for example knobs 502, 503 and/or 518. Specifically, these figures illustrate the preferred step-by-step deployment of the fixation device in antegrade orientation.

Before insertion of the device and delivery assembly through the mitral valve, the device remains in a collapsed state inside the steerable guide catheter shaft 498, wherein, all arms are folded upward. This is illustrated in FIG. 4A by the position of the arms 12, 20, 14, 22.

Figure 4A:
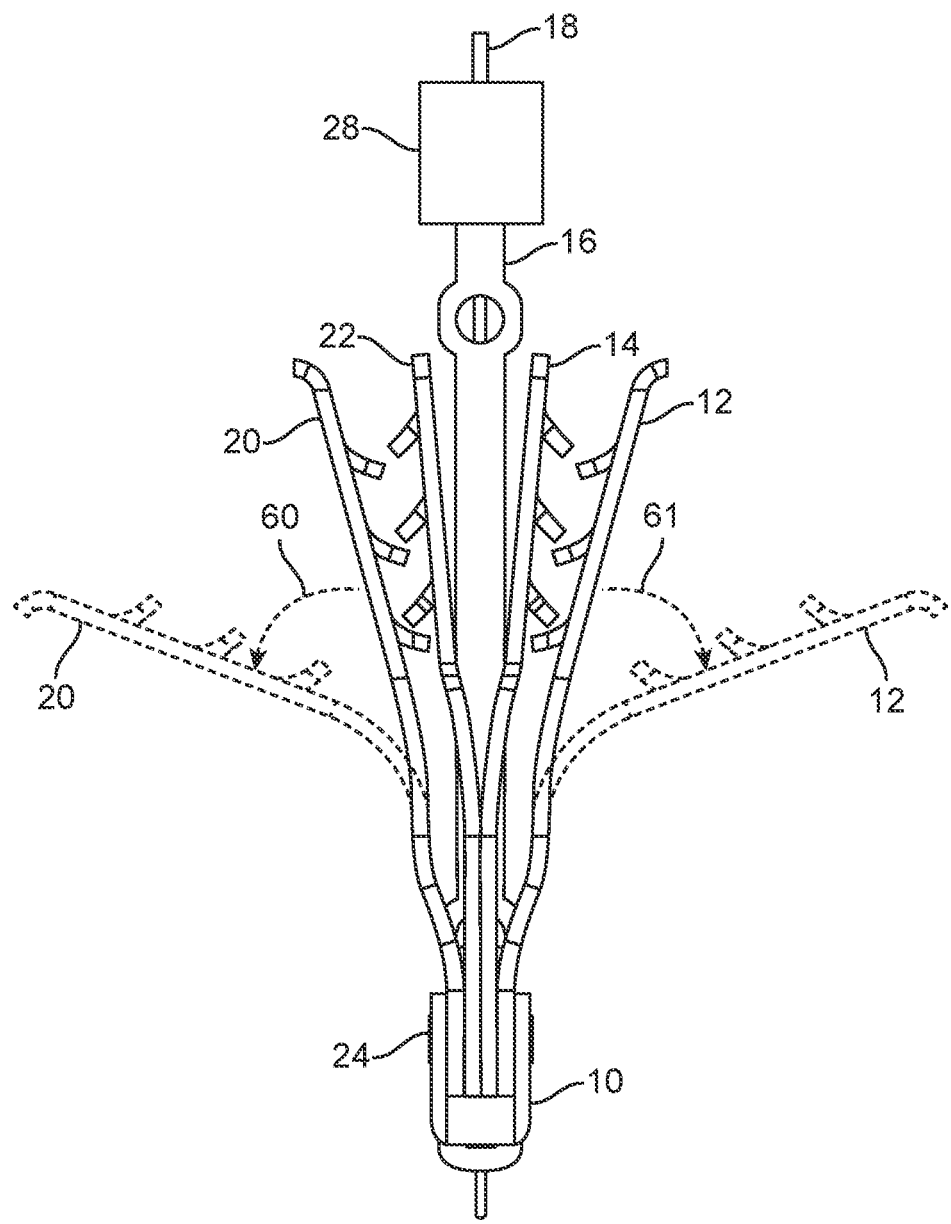
FIG. 4A through 4F depict a step-by-step deployment of the preferred embodiment using simultaneous leaflet capture.

FIG. 4A shows the manipulations 60 and 61 of outer arms 12 and 20 to positions 12' and 20' after insertion of the device past the mitral valve leaflets LF.

Figure 4B:
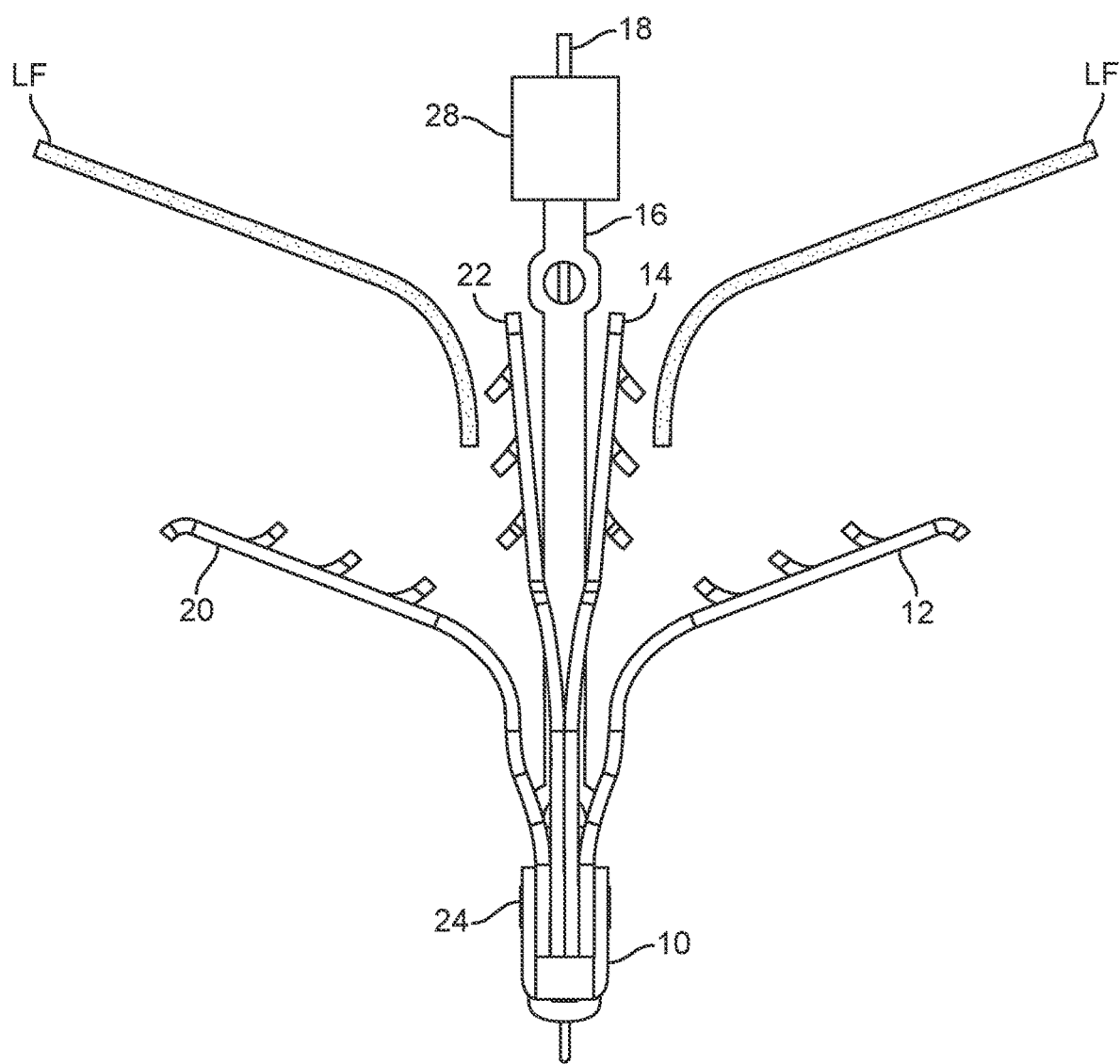

FIG. 4B further illustrates this by showing the final position of the outer arms 12 and 20 facing up underneath the valve leaflets LF.

Figure 4C:
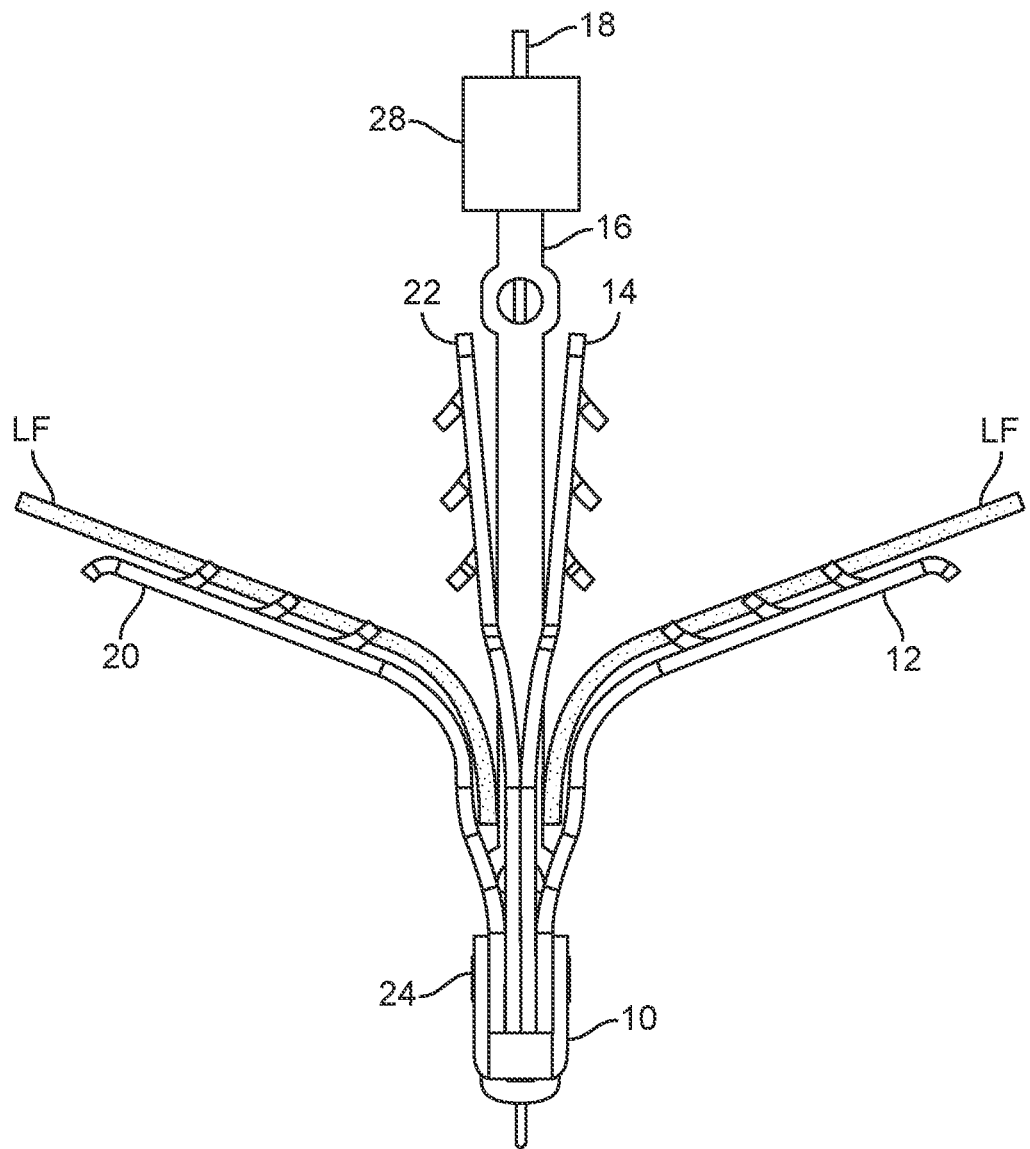

FIG. 4C shows the repositioning of the fixation device such that the mitral valve leaflets LF are secured by the outer arms 20 and 12. This is achieved by translating the device ~1 cm towards the atrial direction.

Figure 4D:
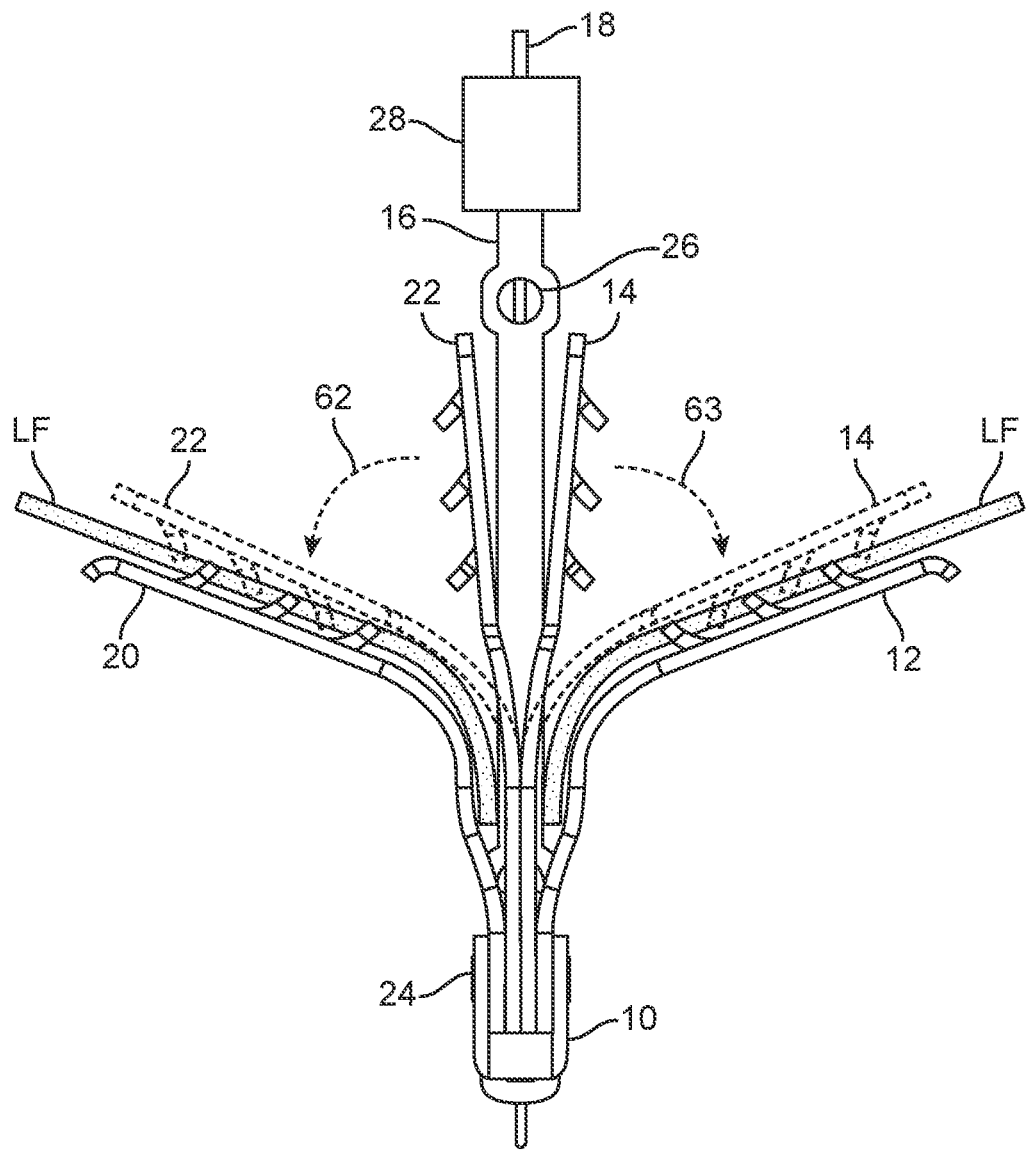

FIG. 4D shows the capture of the leaflets LF by the 62 and 63 movement of arms 14 and 22 to positions 14' and 22'. The barbed features of said elements secure the leaflets LF to the fixation device.

Figure 4E:
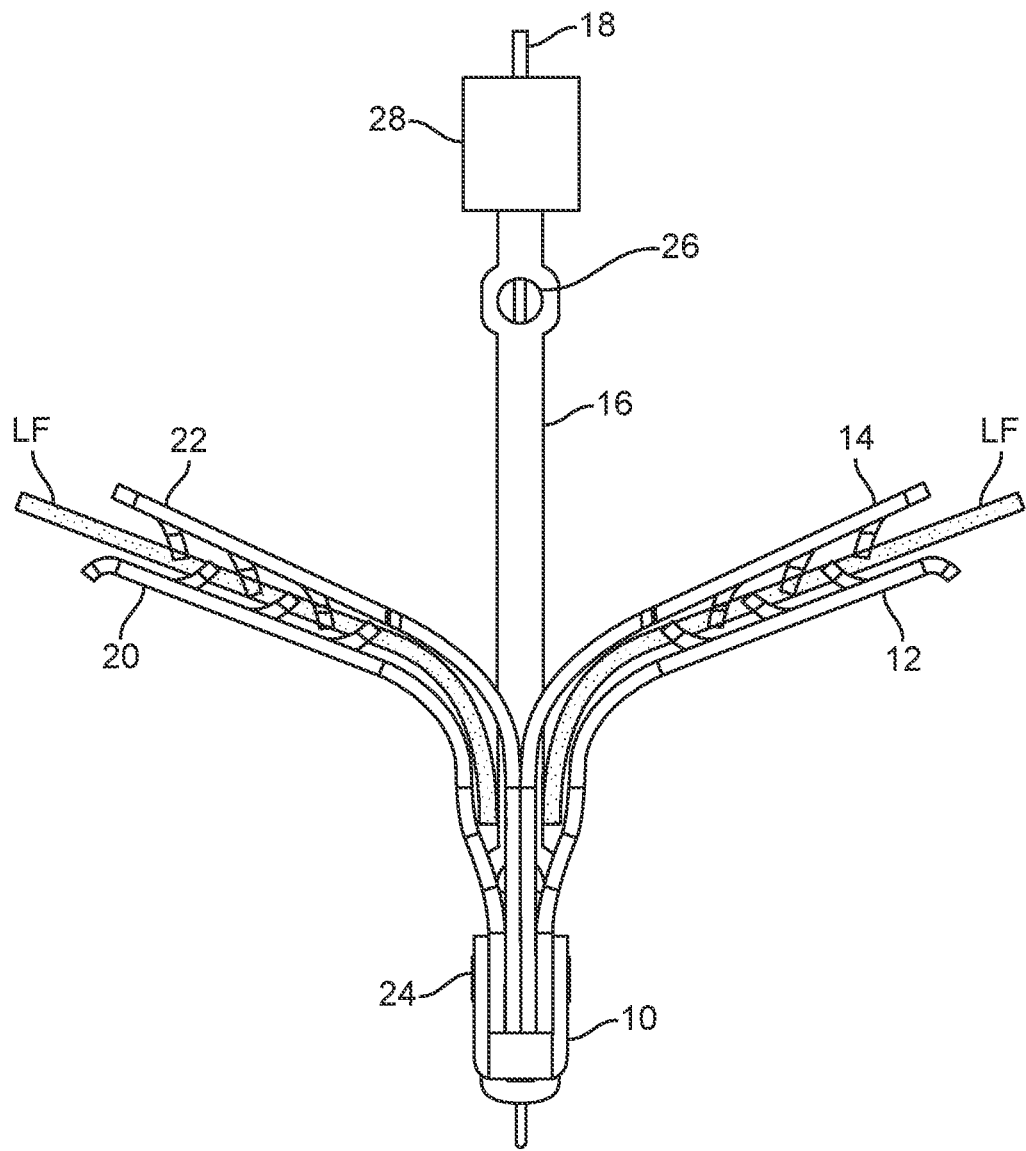

FIG. 4E further illustrates the end product of capture, in which the arms 14, 22, 12, and 20 have effectively captured the leaflets LF of the mitral valve.

Figure 4F:
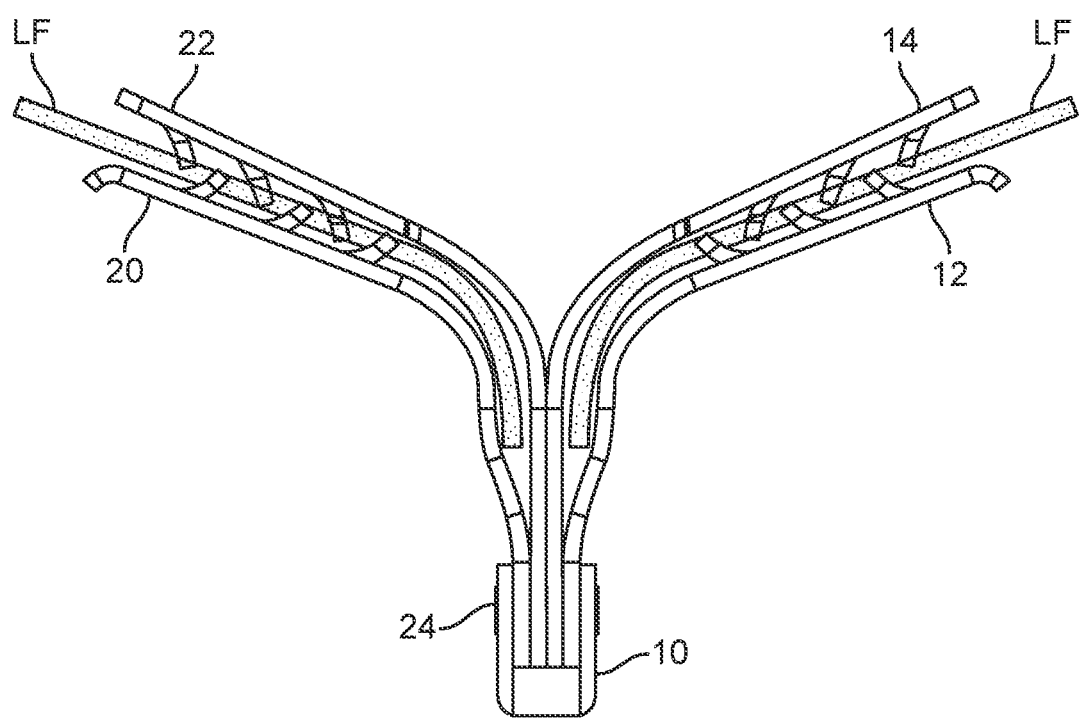

FIG. 4F shows the deployed state of the fixation device. Note that FIG. 4F is the end state of all the described procedures for deployment of the preferred embodiment.

FIGS. 5A-5D depict arm manipulation to be controlled by, for example knobs 502, 503 and/or 518. Specifically, these figures illustrate a step-by-step deployment of the fixation device in an antegrade orientation, in which the each of the inner arms 22 and 14 capture leaflets independently.

Figure 5A:
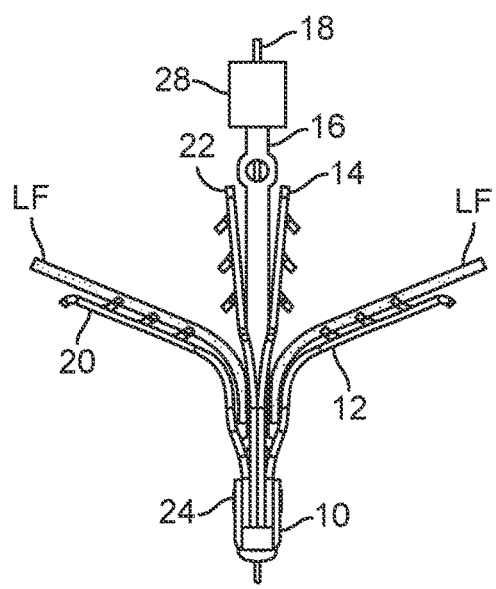
FIG. 5A through 5D depict the step-by-step capture of the mitral valve leaflet using side-by-side capture via independent manipulation of the inner arms.

FIG. 5A illustrates the preferred embodiment after its placement underneath the mitral valve leaflets LF, as explained previously in FIG. 4C.

Figure 5B:
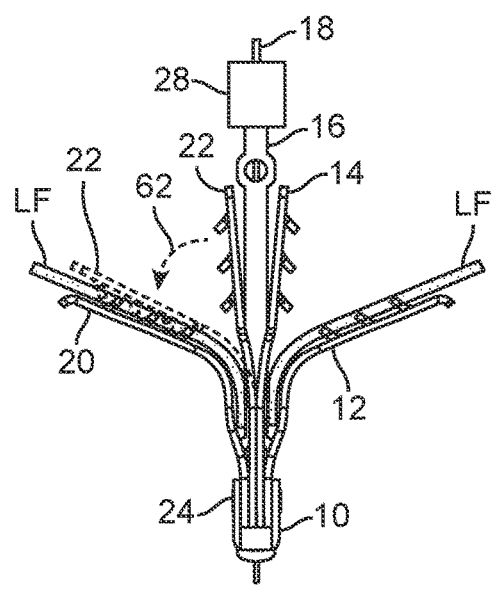

FIG. 5B depicts the independent manipulation 62 to drop inner arm 22 to the position 22', capturing the first leaflet LF.

Figure 5C:
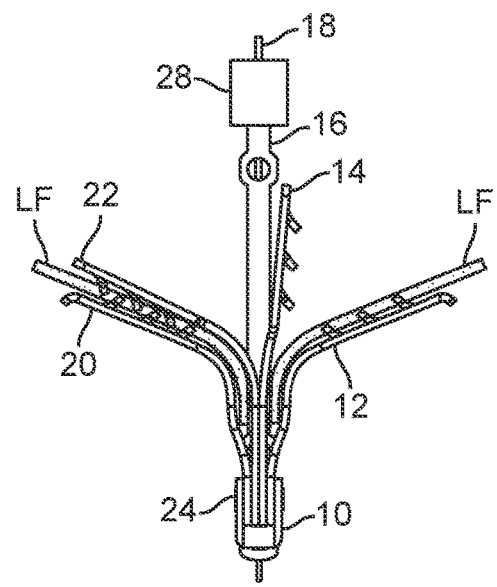

FIG. 5C illustrates the proceeding position of the manipulation 62.

Figure 5D:
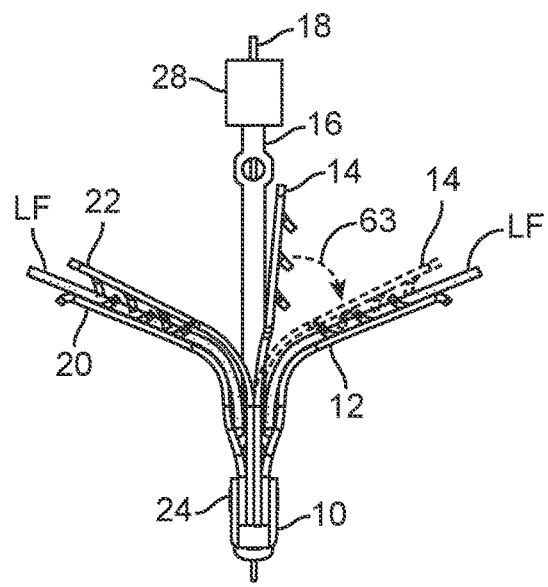

FIG. 5D depicts the independent manipulation 63 of the second inner arm 14 to the position 14', capturing the second leaflet LF. Note that the order of manipulations 62 and 63 are interchangeable to meet the preferred used need.

FIGS. 6A-6D depict alternate variant of independent arm manipulations to sequentially capture the leaflets LF. Specifically, these figures illustrate a step-by-step deployment of the fixation device in an antegrade orientation for the purposes of representation of the idea.

Figure 6A:
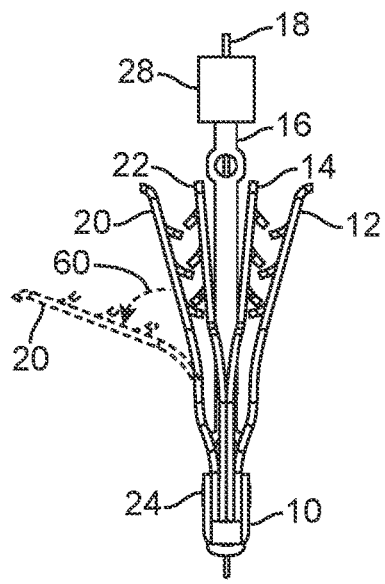
FIG. 6A through 6D depict the step-by-step capture of the mitral valve leaflet using side-by-side capture via independent manipulation of the inner and outer arms.

FIG. 6A illustrates the manipulation 60 of outer arm 20 to position 20'. The device must now be positioned such that the leaflet LF apposes the barbed features of arm 20.

Figure 6B:
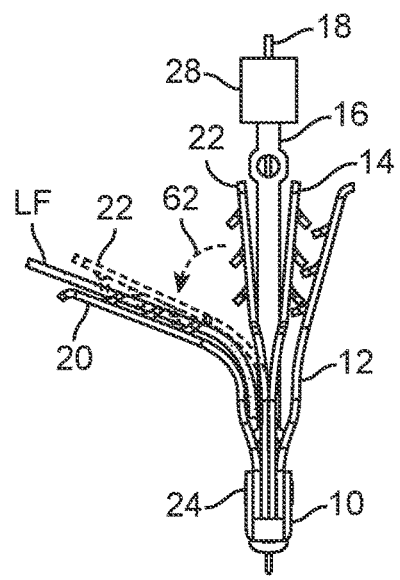

FIG. 6B shows the capture of the leaflet LF by the dropping 62 of inner arm 22 to position 22'. This captures the first leaflet LF.

Figure 6C:
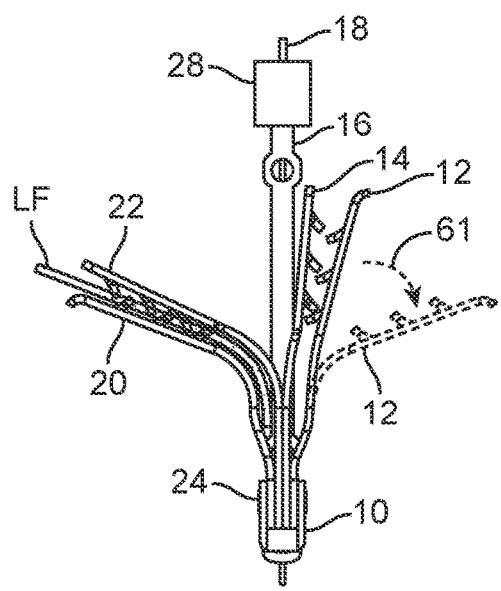

The product of manipulation 60 followed by manipulation 62 is shown in FIG. 6C, in which the device has successfully captured one leaflet LF. It also shows the manipulation 61 to reposition the outer arm 12 to position 12'.

Figure 6D:
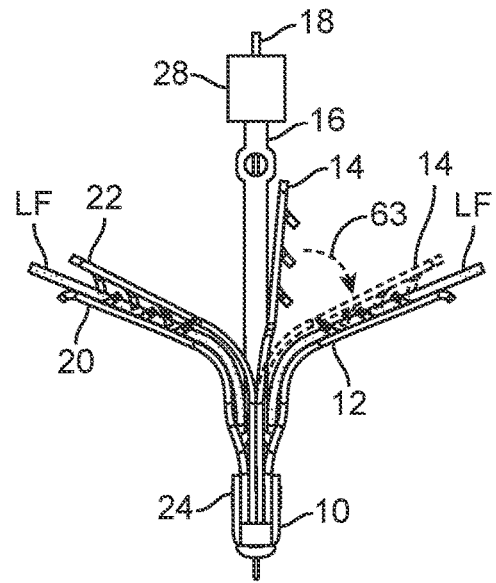

FIG. 6D illustrates the manipulation 63, which drops the inner arm 14 to position 14' in order to capture the second leaflet LF.

Note that the manipulation pairs (60, 62) and (61, 63) may be interchanged in order to meet the user need.

The product of the manipulations depicted in FIGS. 6A-6D is illustrated in FIG. 4E, in which the arms 14, 22, 12, and 20 have effectively captured the leaflets LF of the mitral valve.

The preferred embodiment is designed to allow for the user to abort the device deployment following any complication. Further, bailout procedure may be needed in order to correct or reposition suboptimal capture of leaflets. An example of the "bailout" procedure is illustrated in FIGS. 7A-7F.

Figure 7A:
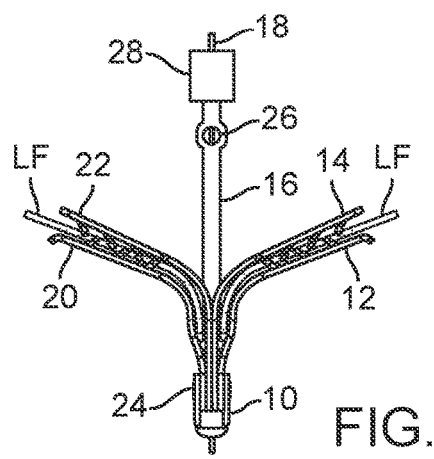
FIG. 7A through 7F depict the step-by-step bailout procedure after any extent of leaflet capture by the arms.

FIG. 7A shows the exemplary fixation device after complete capture of the mitral valve leaflets LF.

Figure 7B:
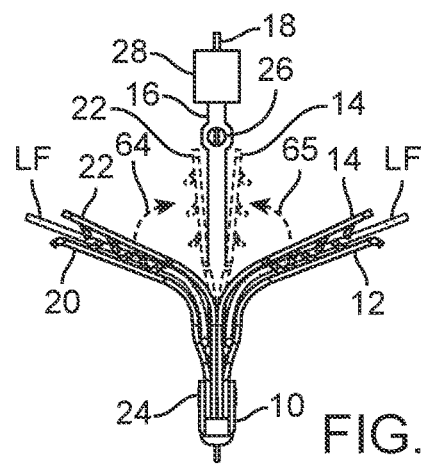
Figure 7C:
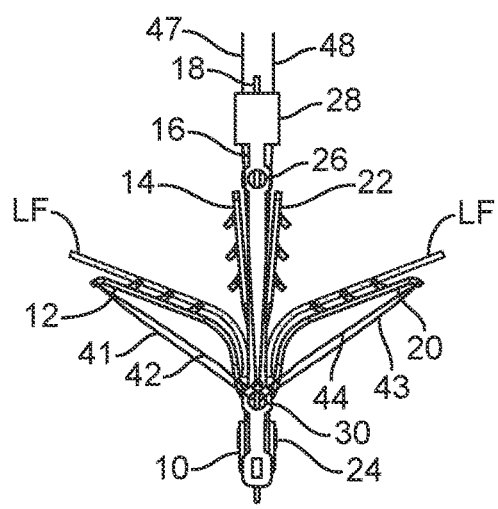
Figure 7D:
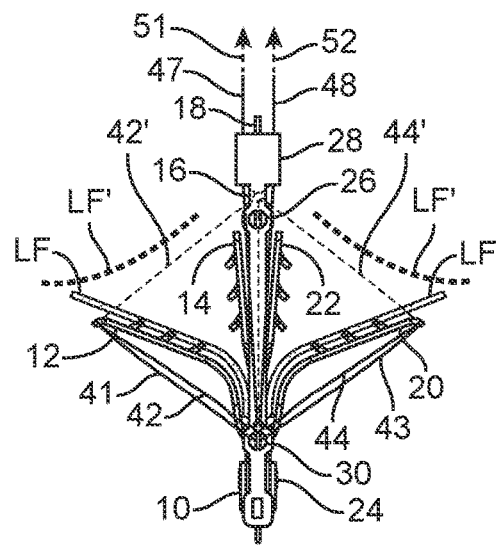
Figure 7E:
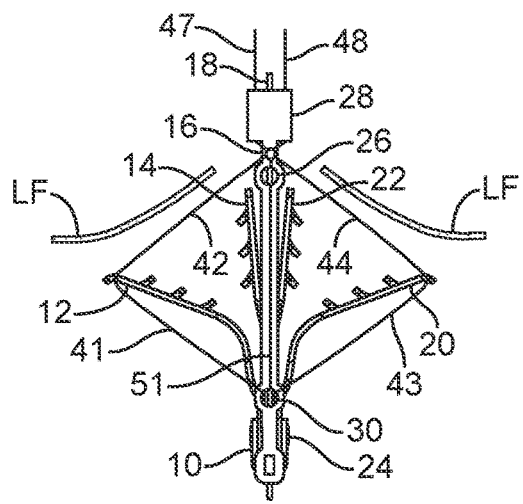
Figure 7F:
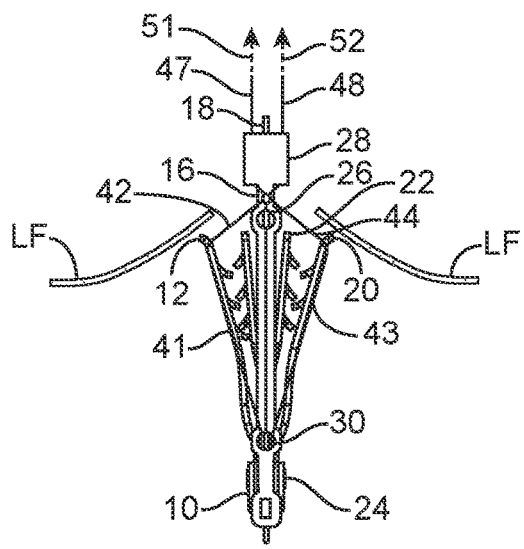

FIG. 7B shows the release of the leaflets LF by lifting the inner capture arms 22 and 14 to positions 22' and 14' via manipulations 64 and 65. FIG. 7C depicts the end result of manipulations 64 and 65. FIG. 7D illustrates the actuations 51 and 52 of sutures 47 and 48, such that suture segments 42 and 44 are translated to positions 42' and 44'. Note that this translation lifts the leaflets LF off of the outer arms 12 and 20 to the positions LF'. FIG. 7E shows the end result of these manipulations 51 and 52. FIG. 7F shows the further embodiment of manipulations 51 and 52, in which the arms 20 and 12 are fully collapsed upward. At this stage, the bailout is complete and the fixation device can be retracted away from the mitral valve into the atrium. The user may choose to re-attempt the procedure or fully retract and remove the fixation device and delivery catheter 499 through the steerable guide catheter shaft 498.

FIGS. 8A-8D give a more detailed depiction of the fixation device's movements and manipulations focusing on the sutures, which connect the fixation device to the delivery system.

Figure 8A:
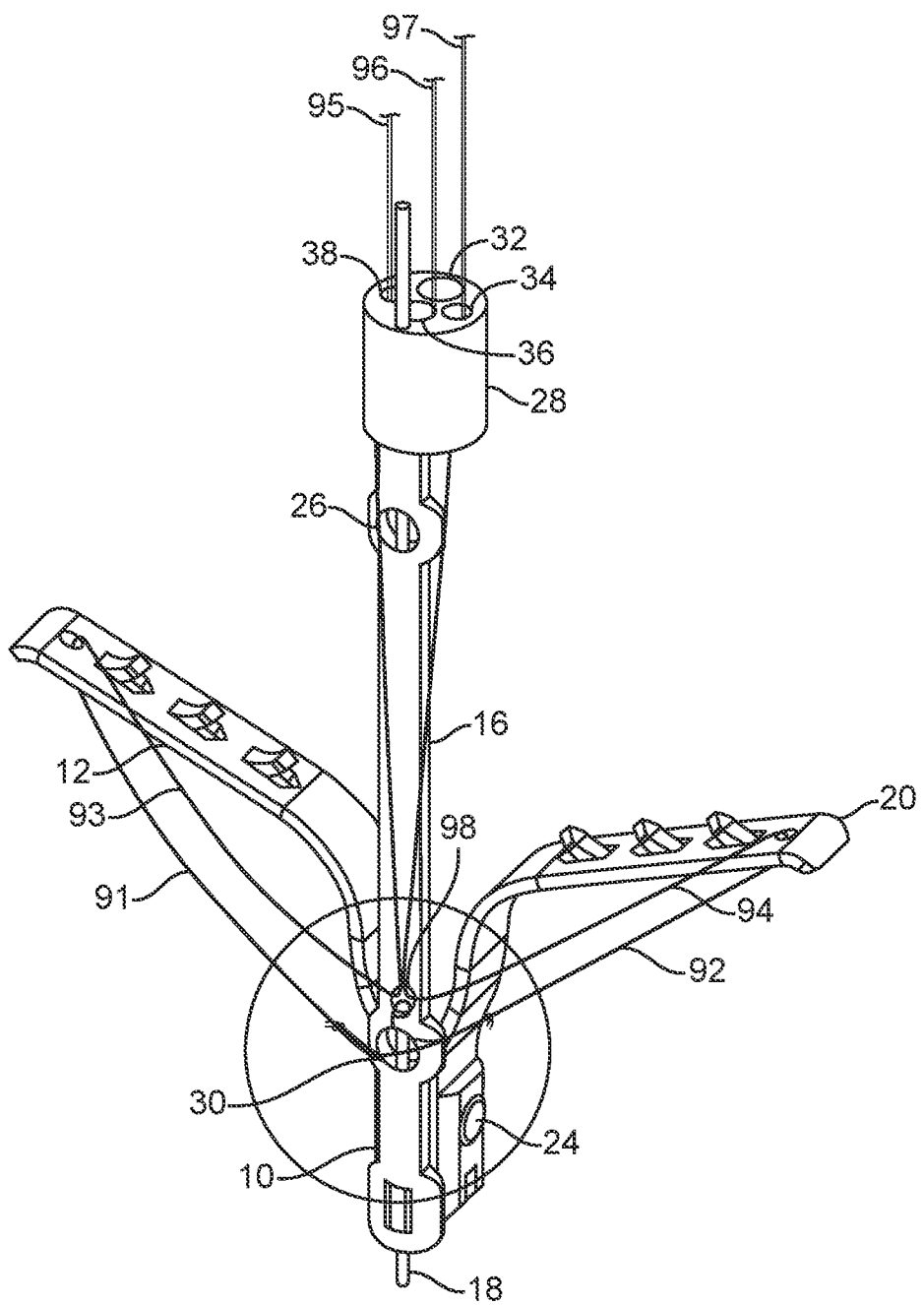
FIG. 8A illustrates the mechanism by which the outer arms are manipulated.
Figure 8B:
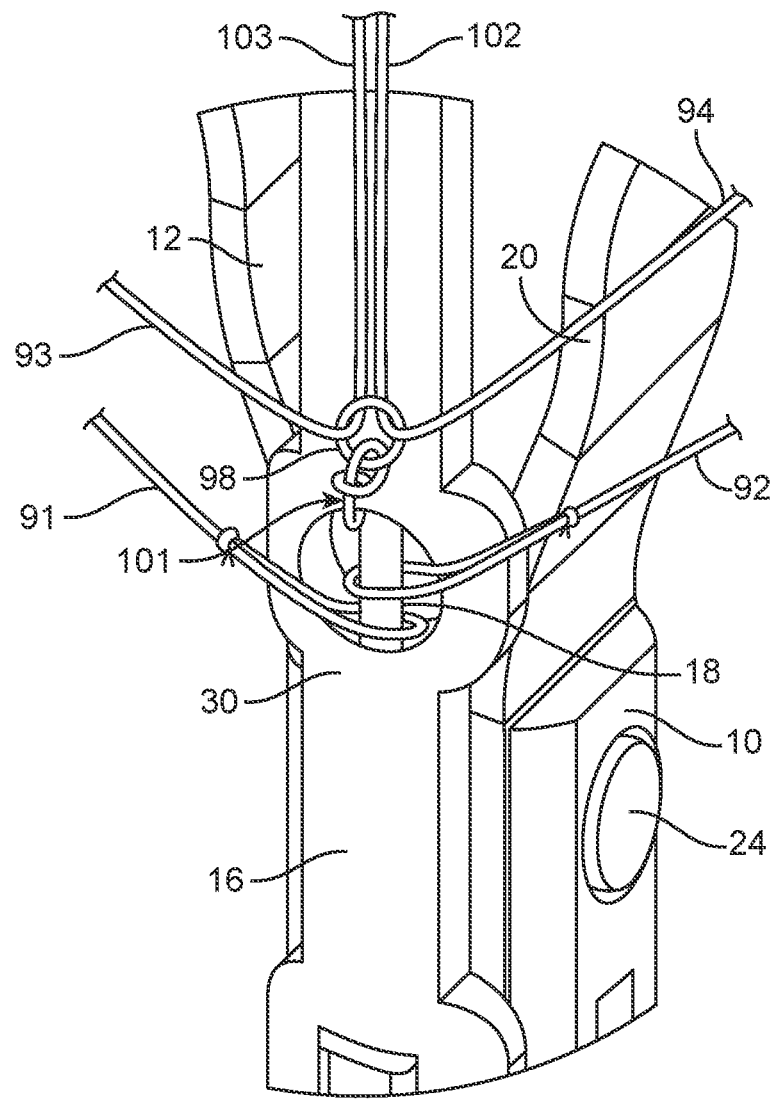
FIG. 8B is a detailed illustration of the mechanism of FIG. 8B.

FIG. 8A illustrates the backside of the device (facing component 16) without showing inner arms 14 and 22 to avoid cluttering of the illustration. This depiction represents the position of all other device elements whilst the outer arms 12 and 20 are ready for capture. Suture 95 travels down the catheter tube and elements 28 and 16, then through loop 98 and forms segments 91 and 93. Suture 97 travels down the catheter tube and elements 28 and 16 and forms segments 92 and 94. The distal ends of sutures 91 and 92 are looped to the release rod 18 through the hole 30. Suture 96 also travels down the catheter tube and the front side of elements 28 and 16, which in turn travels through feature 30 to be looped through loop 98. FIG. 8B is a zoomed-in image of FIG. 8A, designated by the circle drawn around feature 30. Note that the use of a loop 98 can be rendered moot by utilizing the loop at the distal end of suture 96.

Figure 8C:
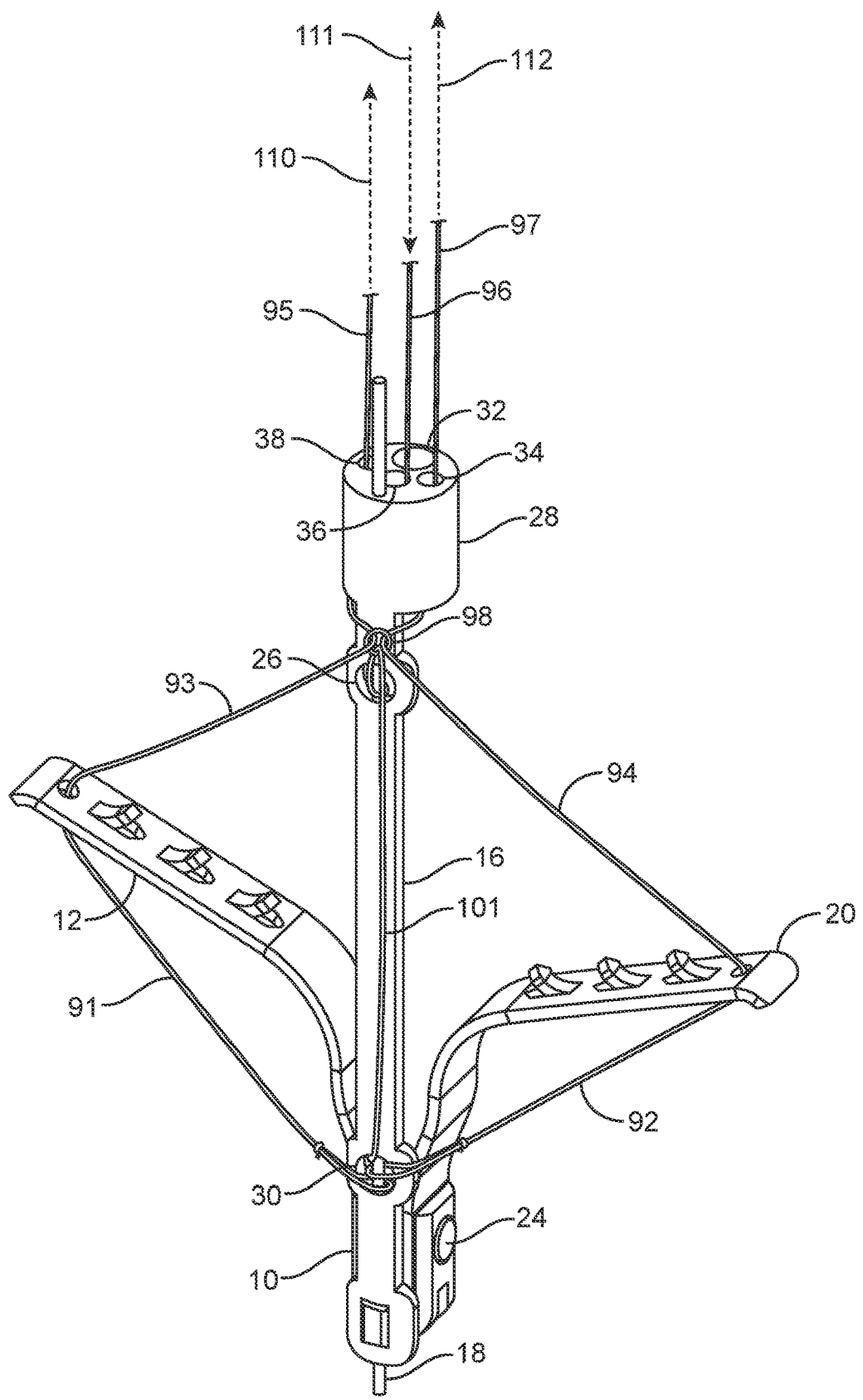
FIG. 8C illustrates an intermediate position of the mechanism of FIGS. 8A and 8B for controlling the outer arms during bailout. This position of the sutures is beneficial ejecting the mitral valve leaflets from the device.
Figure 8D:
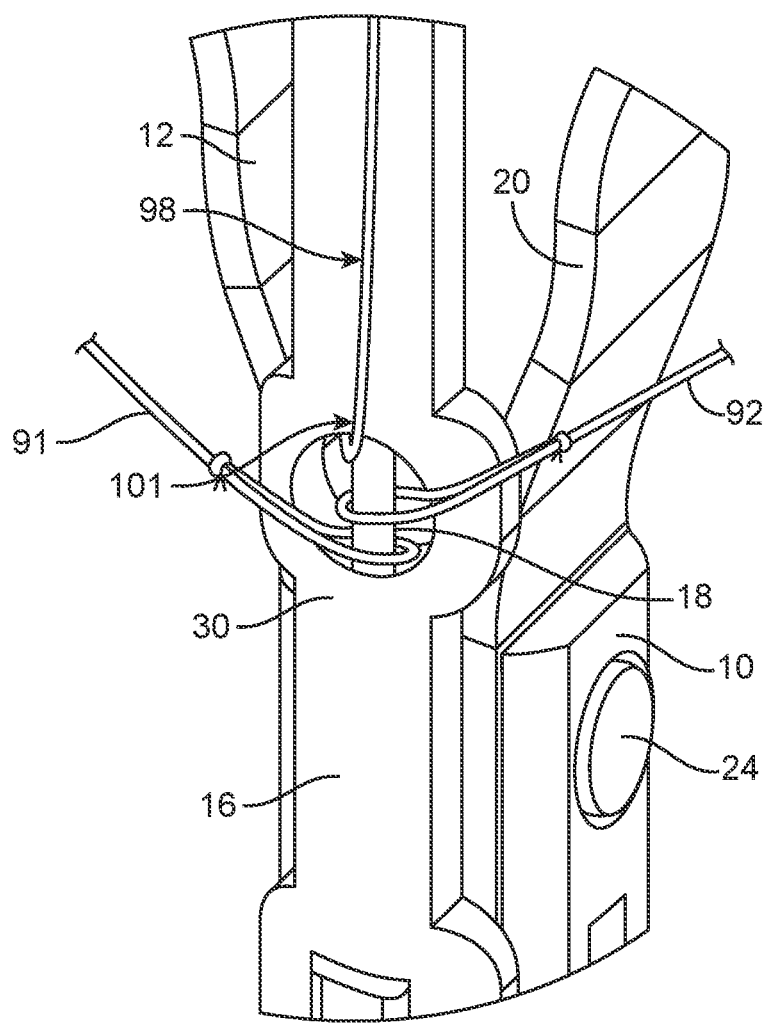
FIG. 8D is a detailed view of the mechanism of FIG. 8C.

FIG. 8C represents a further embodiment of the illustration within FIG. 8A. Here, the manipulations 110, 111, and 112 translate the suture segments 93, 94, and 98 from their original positions held in FIG. 8A. Note that manipulations 110 and 112 can be via knobs on the handle (for example Knob 518), while, this ejects the leaflets LF from their positions on the outer arms 12 and 20, allowing for bailout. FIG. 8C is essentially a more detailed illustration of the preferred embodiment in FIG. 7E. FIG. 8D offers a zoomed image of the embodiment in FIG. 8C, designated by the black circle drawn around element 30. Note that in a preferred exemplary embodiment, manipulations 110 and 112 can be active manipulations of knobs on the delivery handle (for example simultaneous pull on both 110 and 112 using a single Knob 518) while, the manipulation 111 can be passive (for example exerting a constant tension using a spring).

FIGS. 9A through 9D offer a more detailed view of the mechanisms that manipulate the inner arms 14 and 22. Note that the sutures and mechanisms involving the outer arms 12 and 20 are not displayed in FIG. 9A through 9D for simplicity.

Figure 9A:
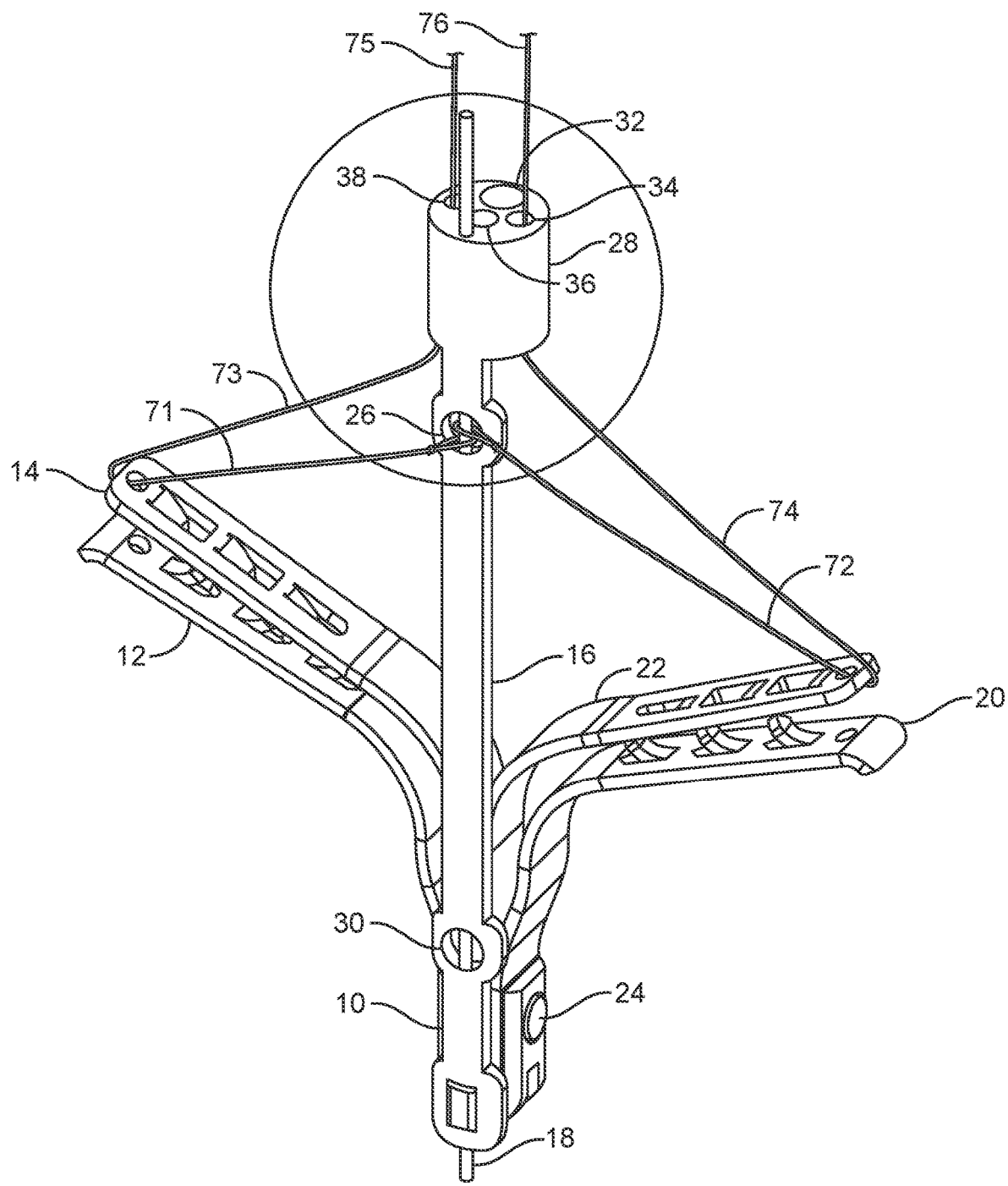
FIG. 9A illustrates a mechanism for manipulating the inner arms.
Figure 9B:
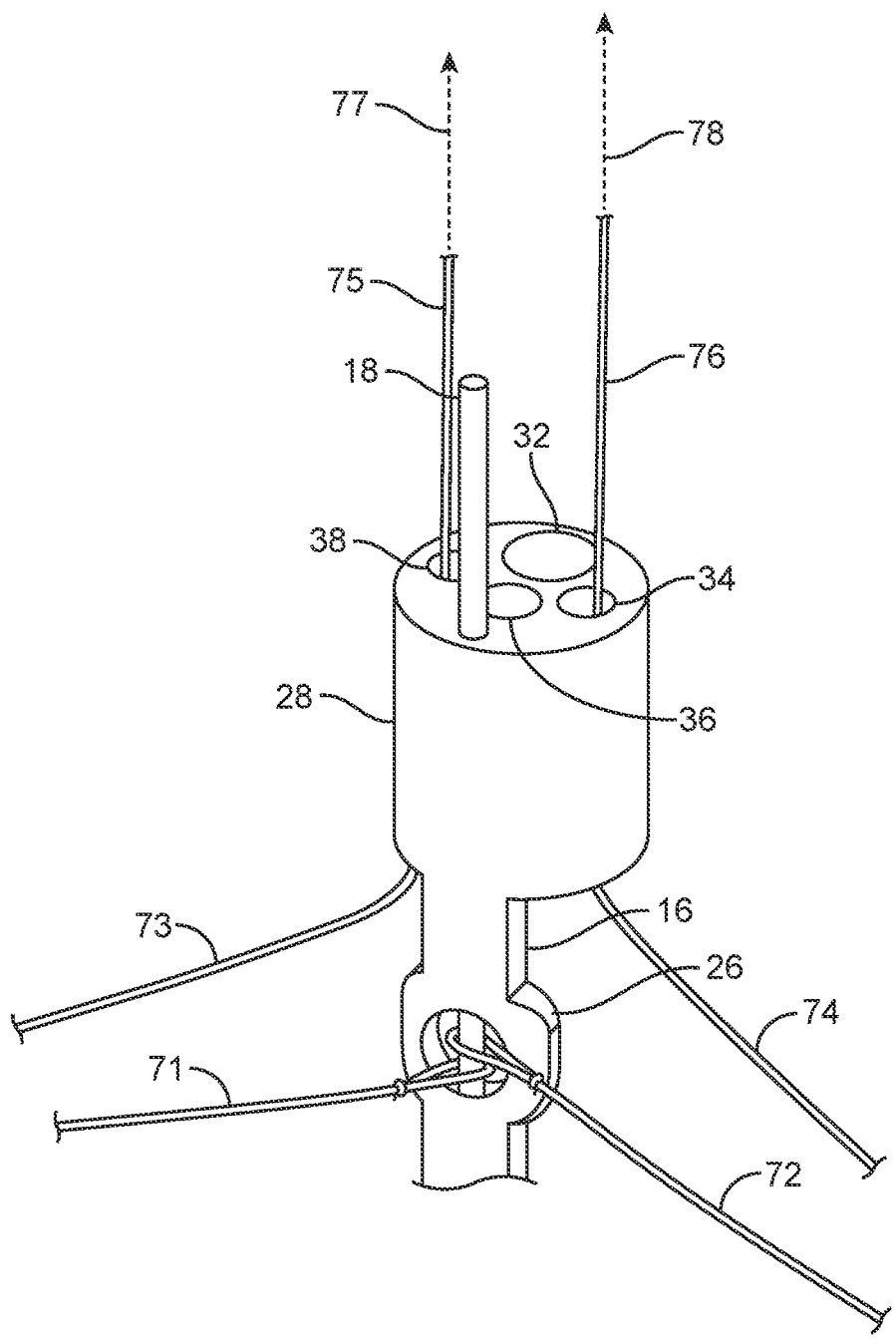
FIG. 9B is a detailed view of the mechanism of FIG. 9A.
Figure 9C:
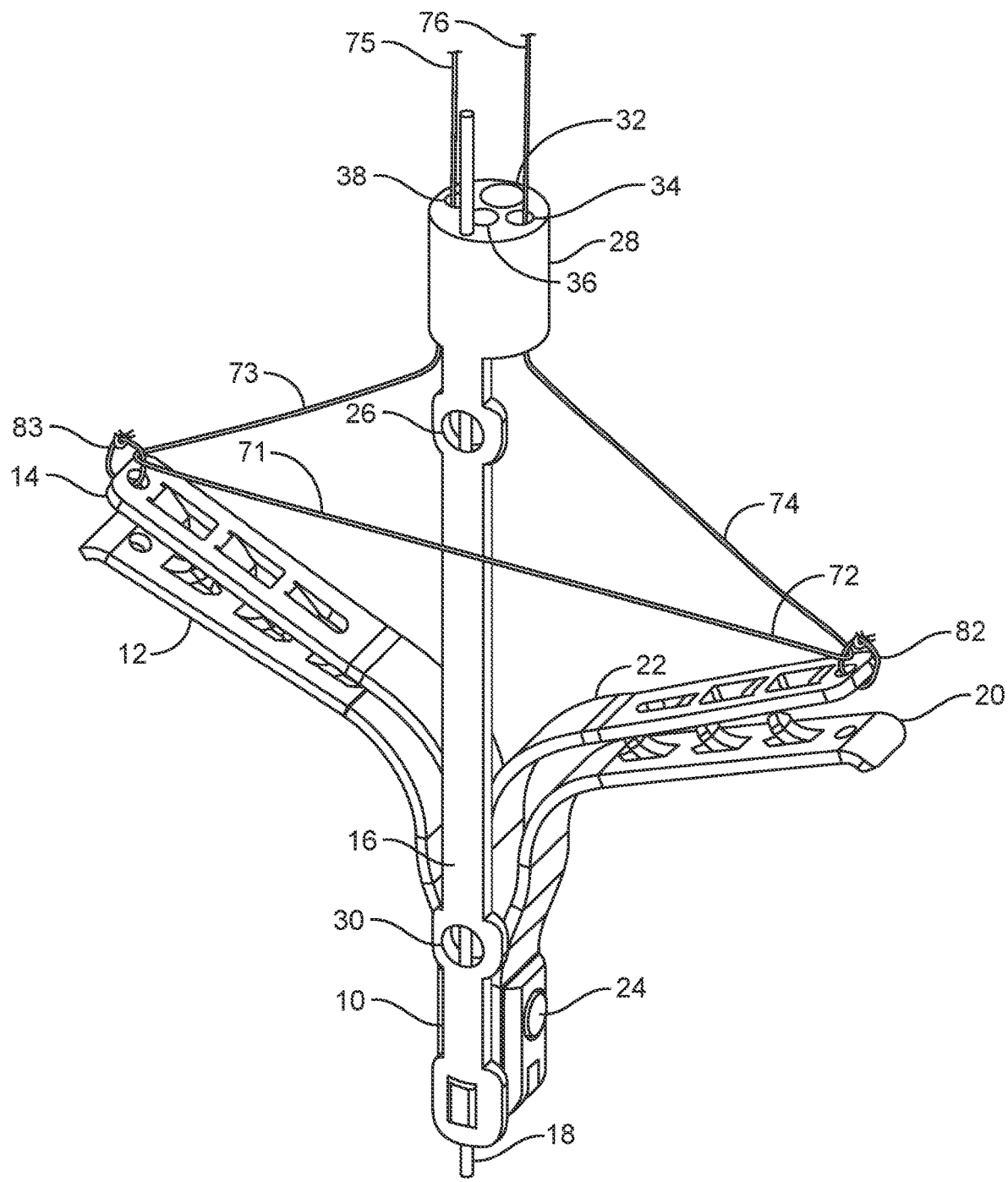
FIG. 9C shows an alternative embodiment of a mechanism for manipulating the inner arms.
Figure 9D:
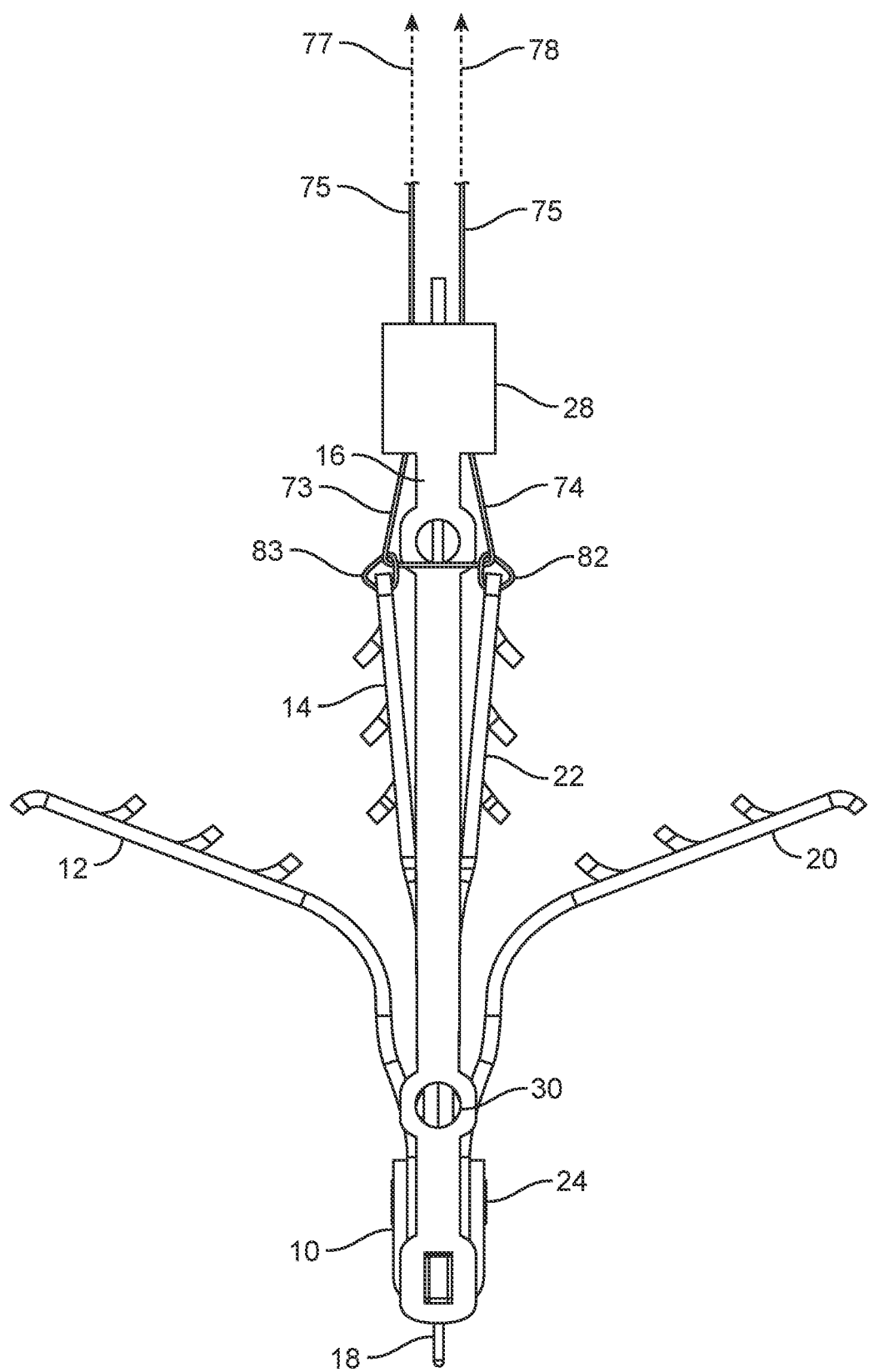
FIG. 9D shows the mechanism of FIG. 9C with the inner arms in a collapsed state.

FIG. 9A illustrates the fixation device prior to the manipulations 77 and 78 act on sutures 75 and 76 in order to collapse the inner arms 14 and 22. Note that suture 76 is also comprised of segments 74 and 72. Similarly, suture 75 is comprised of segments 73 and 71. The distal ends of segments 71 and 72 are looped around the release rod 18 through feature 26 on the deployment bar 16. FIG. 9B offers a closer view of the mechanisms and sutures described above, designated by the circle drawn around feature 26. FIG. 9C depicts a further embodiment of the fixation device, wherein the suture segments 71 and 73 loop via a separate suture loop 83 that is attached to the inner arm 14. Similarly, suture segments 72 and 74 loop via a separate suture loop 82. the sutures loops through loops 83 and 82. FIG. 9D shows the fixation device, wherein, continuation of manipulations 77 and 78 have successfully collapsed the inner arms 14 and 22. This is essential in the bailout procedure, as it allows the device to be compacted for retraction. In addition, this manipulation for raising and lowering of the inner arms, while keeping the outer arms are lowered, allows the user to make several attempts to capture the leaflets.

FIGS. 10A through 10E illustrate the deployment and separation of the fixation device from the delivery system.

Figure 10A:
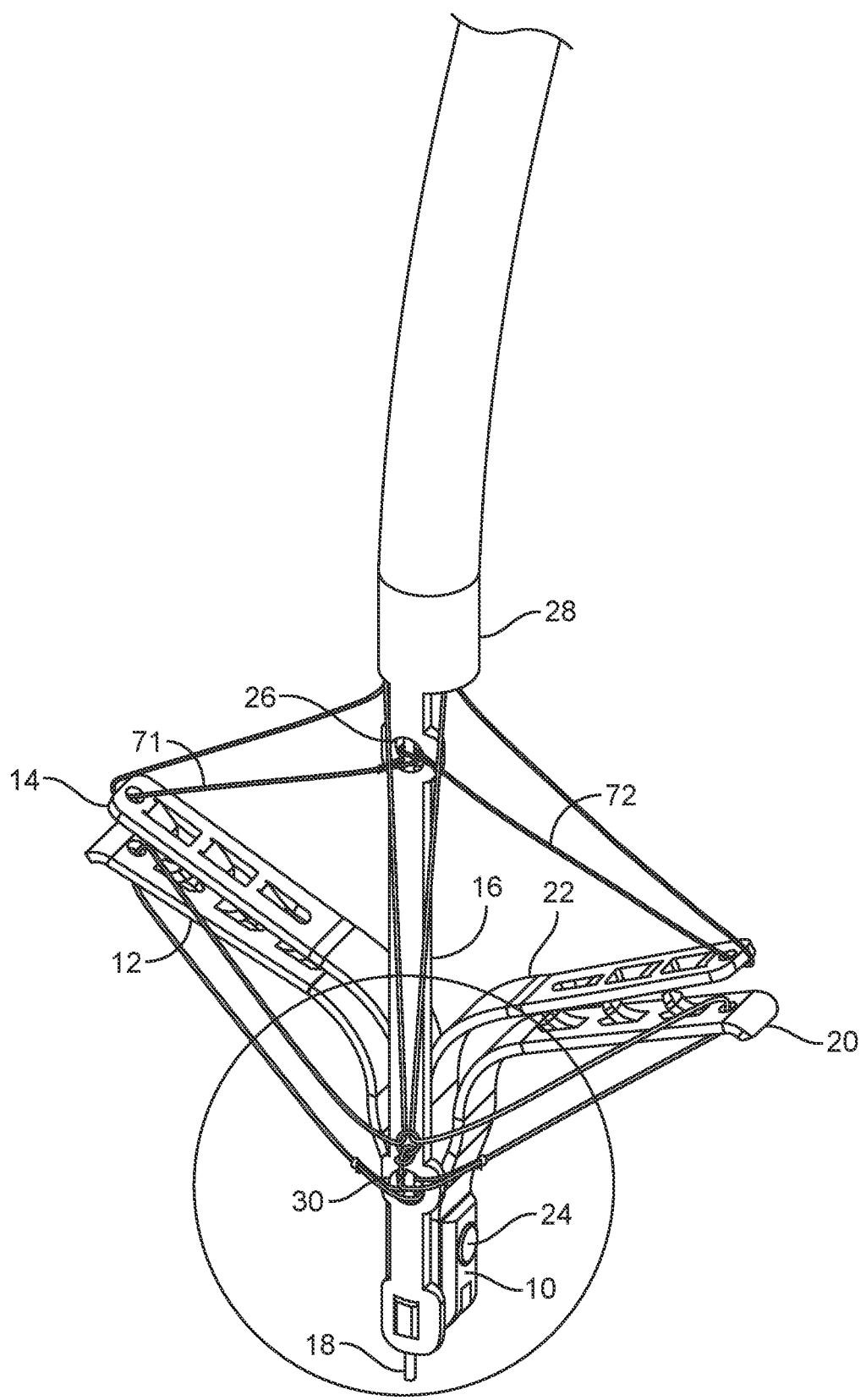
FIG. 10A illustrates another embodiment of the clip and deployment mechanism for controlling both the inner and outer arms.
Figure 10B:
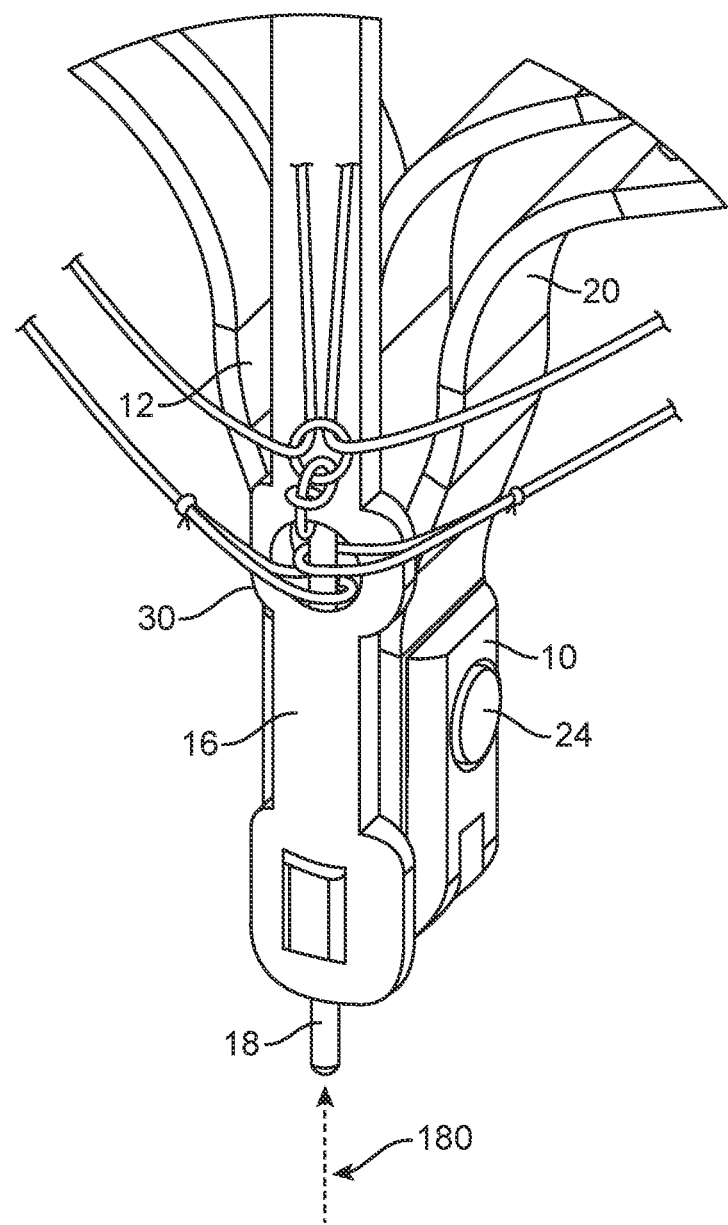
FIG. 10B is a detailed illustration of the deployment mechanism of FIG. 10A, with retraction of a release rod.
Figure 10C:
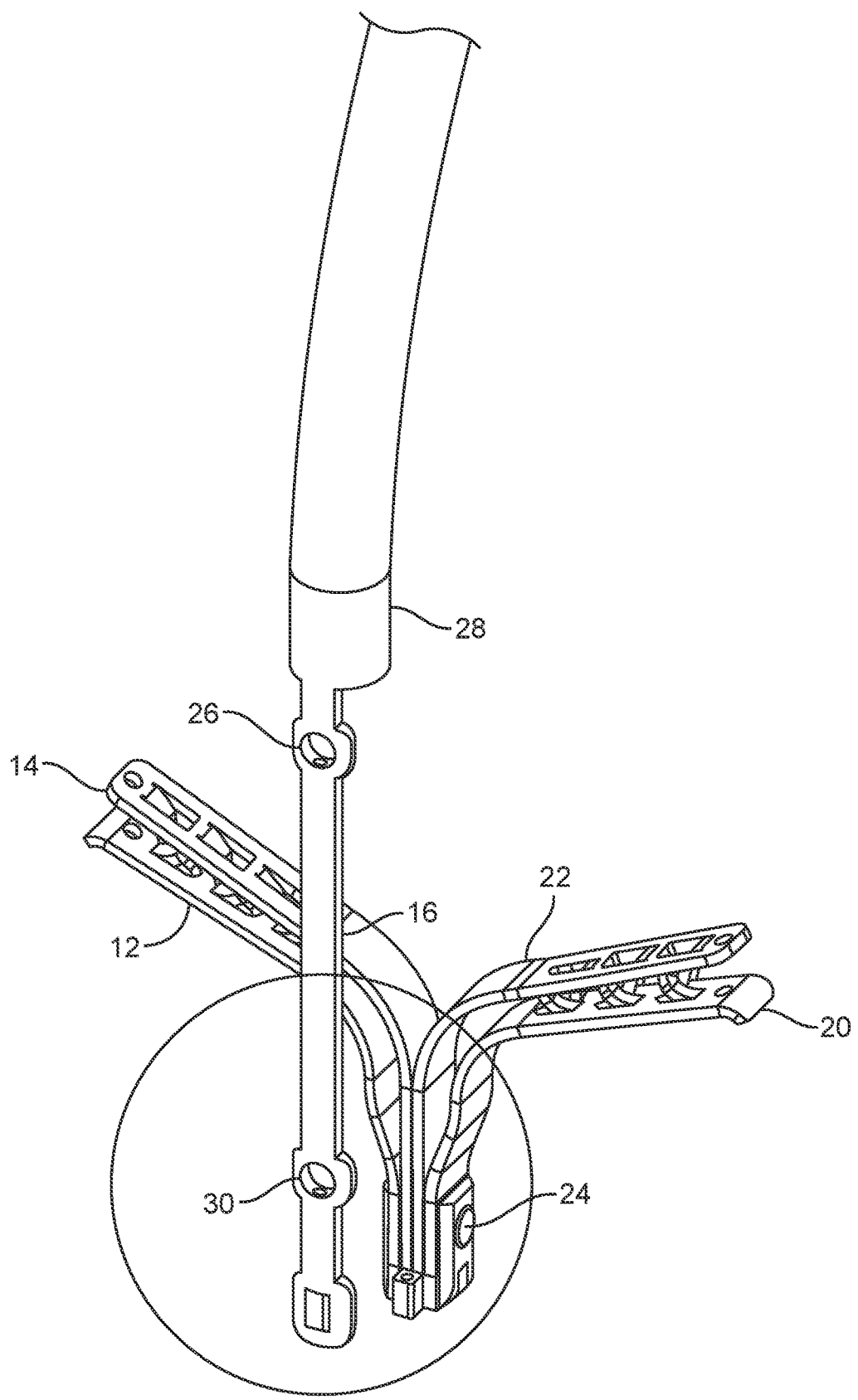
FIG. 10C depicts the release of a valve clip using the release rod of FIG. 10B.
Figure 10D:
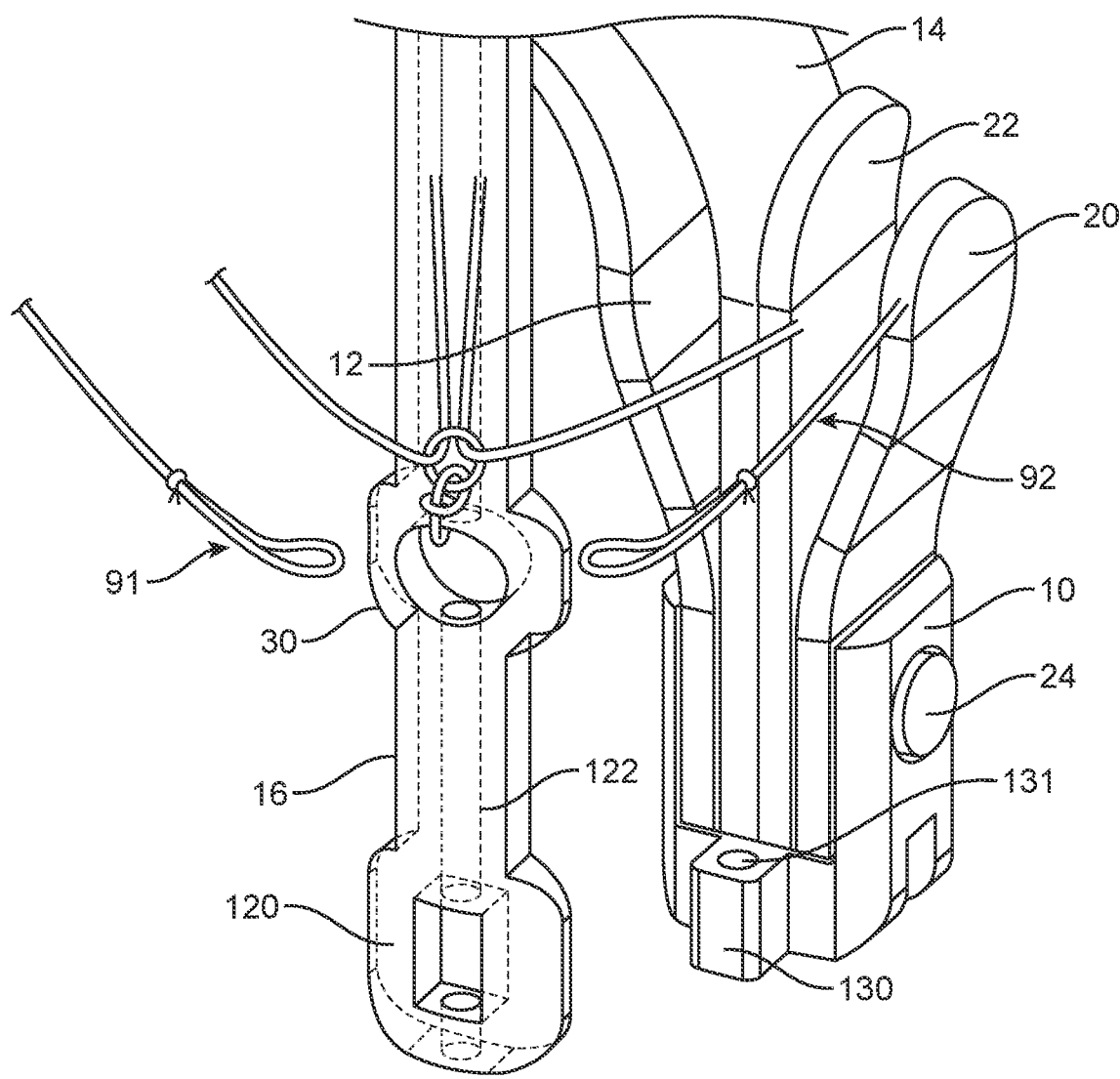
FIG. 10D is a detailed view of the release mechanism pictured in FIG. 10C.
Figure 10E:
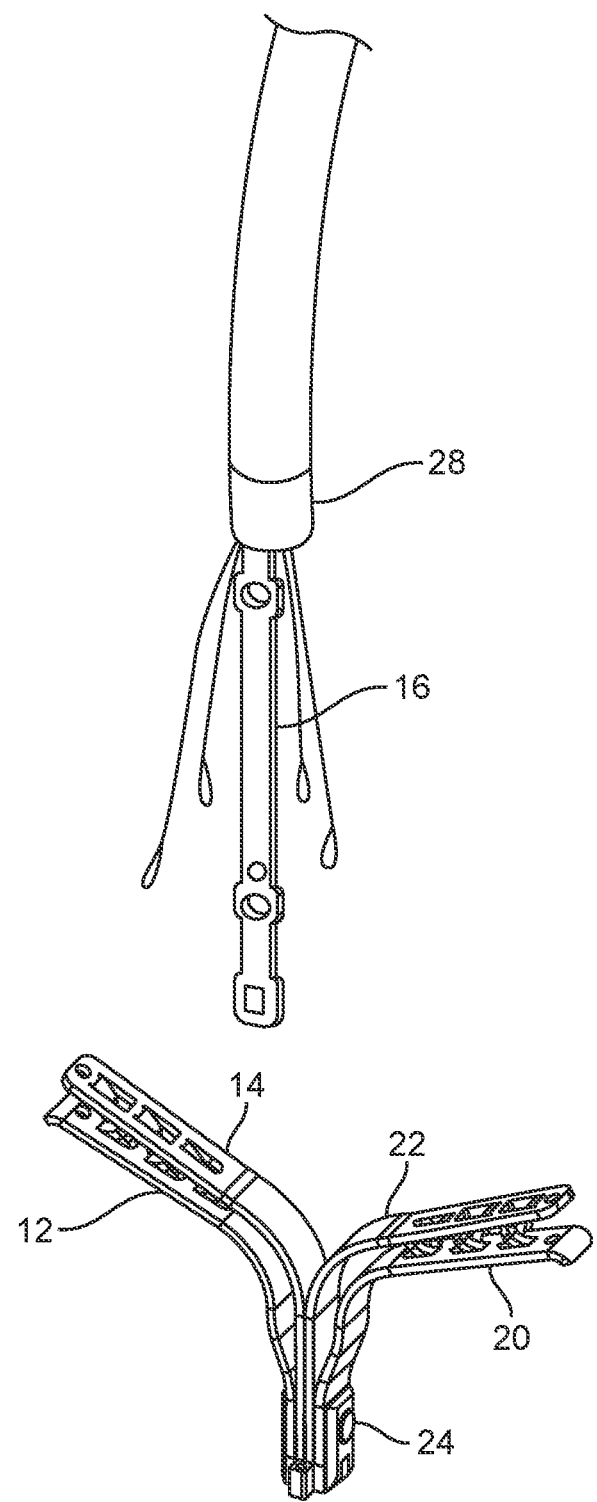
FIG. 10E depicts retraction of the delivery system after release of the valve clip.

FIG. 10A depicts the fixation device in its end position after capturing the mitral valve leaflets LF (NOT SHOWN). FIG. 10B is a zoomed image of a circular portion of FIG. 10A, designated by the circle drawn around element 30. Here, manipulation 180 acts on the release rod 18 as it is pulled from the delivery system, for example, using the release rod knob 550. The result of this manipulation is shown in FIG. 10C, where the fixation device has been effectively separated from the deployment bar 16. FIG. 10D depicts the effect of manipulation 180 on the suture segments 91 and 92: they are unlinked from the device due to the removal of the release rod 18 and retracted along their lengths up through the delivery system. Note that the release of suture segments 71 and 72 occurs through the same mechanism through feature 26. The end product of the release can be viewed in FIG. 10E, in which the device has successfully been implanted within the heart and the distal delivery system is ready for retraction.

Figure 11:
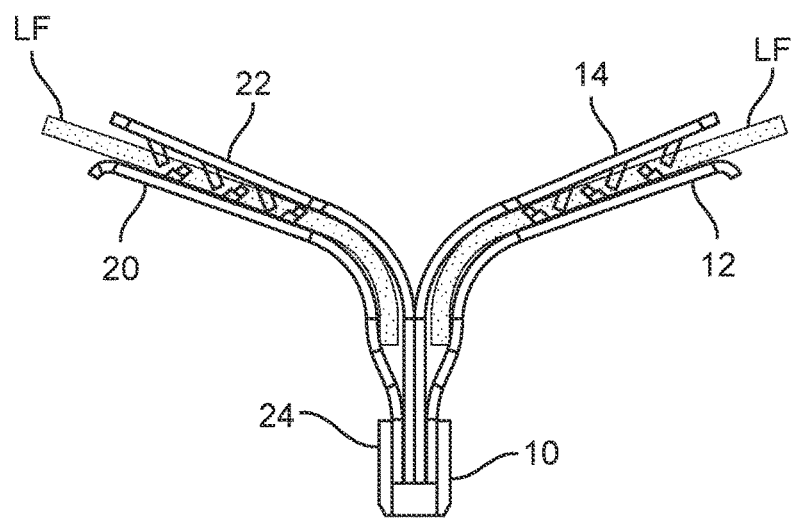
FIGS. 11 and 11A-11D illustrate a specific fixation device (valve clip) embodiment, with isolated views of the inner and outer arms.
Figure 11A:
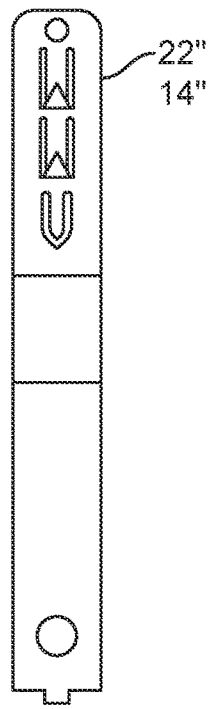

FIG. 11 shows an example of embodiment with inner (22, 14) and outer (12, 20) arms post shape-set, outside of the fixation device. Additionally, it shows the flat pattern of the inner (22", 14") and outer (12", 20") arms to illustrate one method of manufacturing the arms using laser or wire EDM cut nitinol flats.

Figure 12:
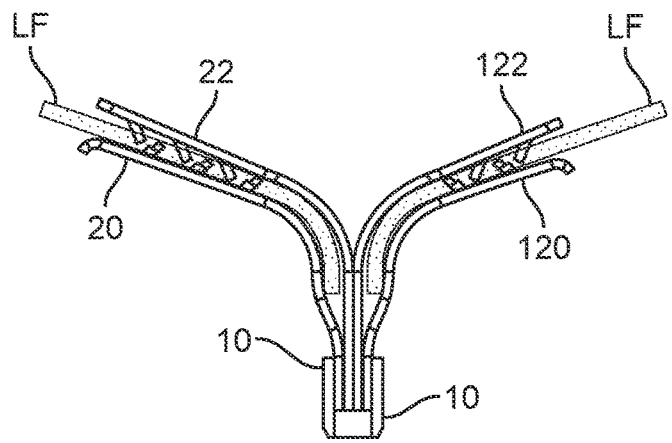
FIGS. 12 and 12A-12D illustrate a further embodiment of a valve clip fixation device in which opposed arms have dissimilar lengths with isolated views of the inner and outer arms.
Figure 12A:
Figure 12B:
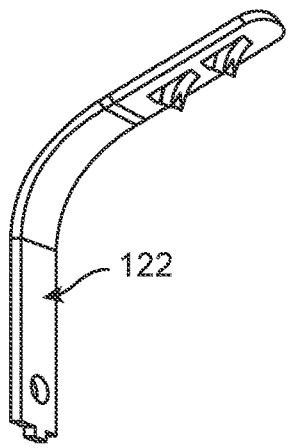
Figure 12C:
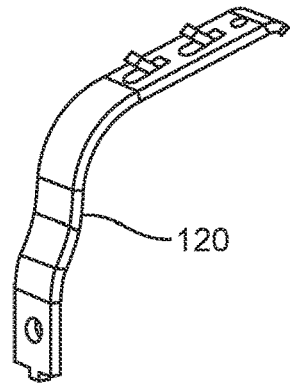
Figure 12D:
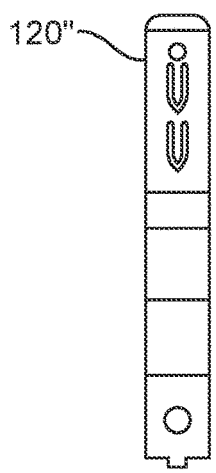
Figure 12E:
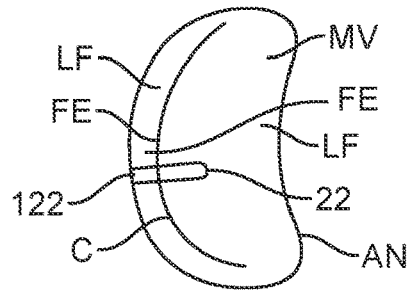
FIG. 12E illustrates the valve clip of FIG. 12 implanted in a mitral valve.

FIG. 12 shows an example of preferred embodiment with inner (22, 122) and outer (120, 20) arms post shape-set, outside of the fixation device. Note that the inner 122 and outer 120 arms are shorter than 22 and 20, to accommodate shorter posterior mitral valve leaflets. Additionally, it shows the flat pattern of the inner (122") and outer (120") arms to illustrate one method of manufacturing the arms using laser or wire EDM cut nitinol flats.

FIG. 13A through 13E illustrate various alternate embodiments of the fixation device. Note that any combination of these embodiments and previously discussed embodiments may be used to address the desired user need.

Figure 13A:
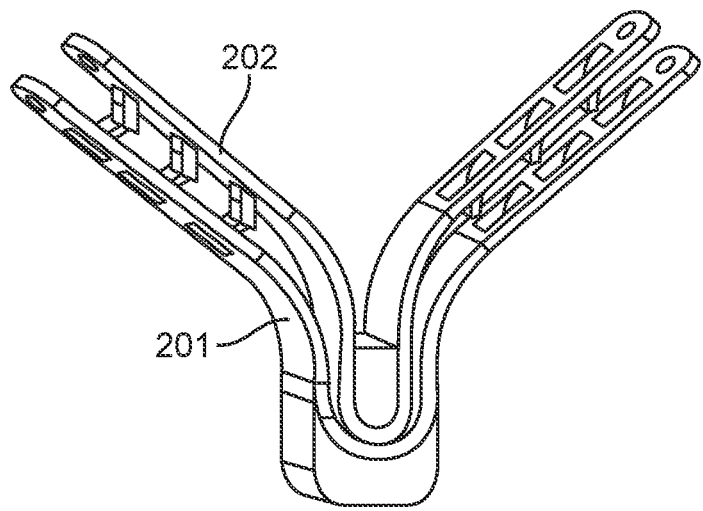
FIG. 13A illustrates a further embodiment of a valve clip fixation device in which the inner and outer arms are formed by single parts.

FIG. 13A illustrates an embodiment wherein, both outer arms are formed as a single, continuous bifurcated outer arm component 201 that grasps the leaflet on either side. Similarly, both inner arms are formed as a single, continuous bifurcated inner arm component 202 that grasps the leaflet on either side.

Figure 13B:
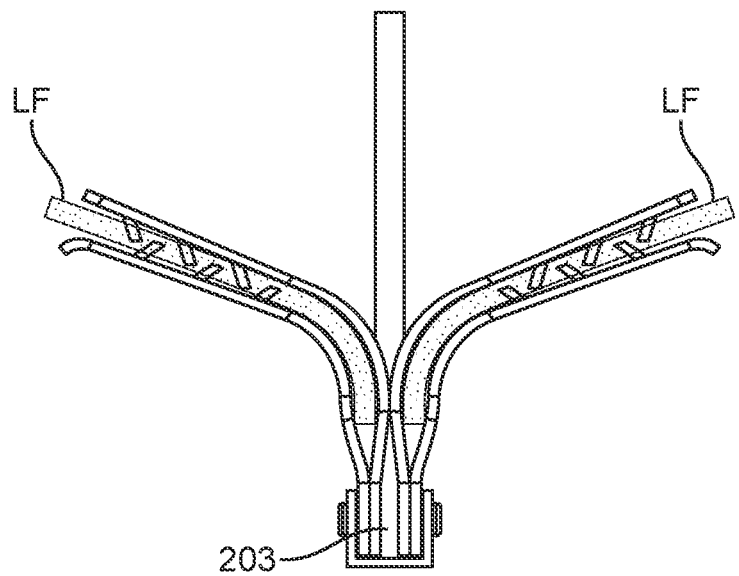
FIG. 13B illustrates a further embodiment of a valve clip fixation device having a spacer in the base.

FIG. 13B shows an example of embodiment of the fixation device wherein there a spacer 203 in between the inner arms. This spacer provides a) provide space for thicker leaflets LF, b) provide additional flexibility to the inner arms, and c) provide an alternate site to detachably couple the fixation device with the delivery catheter.

Figure 13C:
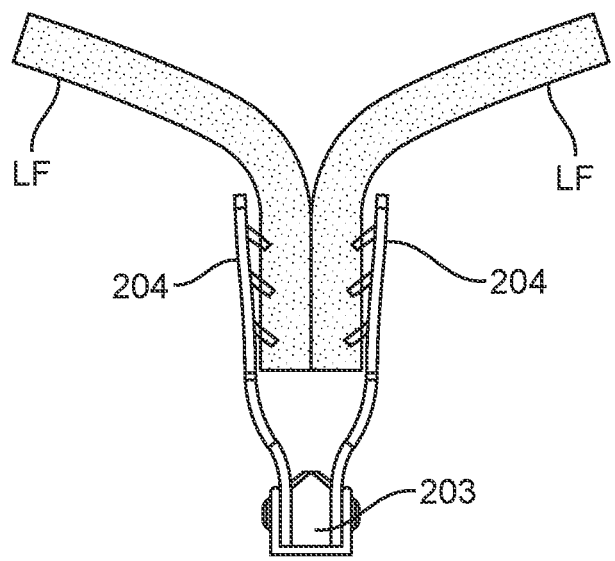
FIG. 13C illustrates a further embodiment of the fixation device which utilizes two arms.

FIG. 13C illustrates an example of a valve clip fixation device embodiment having only two outer arms 204 and no inner arms, designed to capture the leaflets LF. Additionally, FIG. 13C shows an example of embodiment of the fixation device wherein there is a spacer 203 in between the arms. This spacer may be used to provide gap for tissue capture or for attachment of the fixation device to the delivery catheter.

Figure 13D:
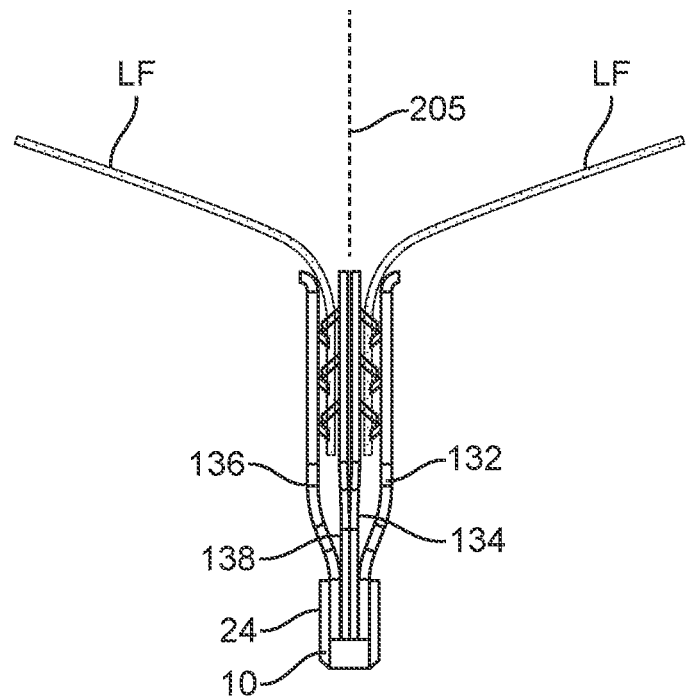
FIG. 13D illustrates a further embodiment of the fixation device in which utilizes four arms along the coapting length of the native leaflet.

FIG. 13D illustrates a valve clip fixation device embodiment using a pair of outer arms 136, 132 and inner arms 134, 138, to capture the leaflets LF, primarily along a line of caption 205 of the native valve. In contrast to previous embodiments where the capture arms diverge from the line of coaptation when grasping the leaflets, the capture arms of FIGS. 13C and 13D are aligned in parallel with the line of coaptation when grasping the leaflets.

Figure 13E:
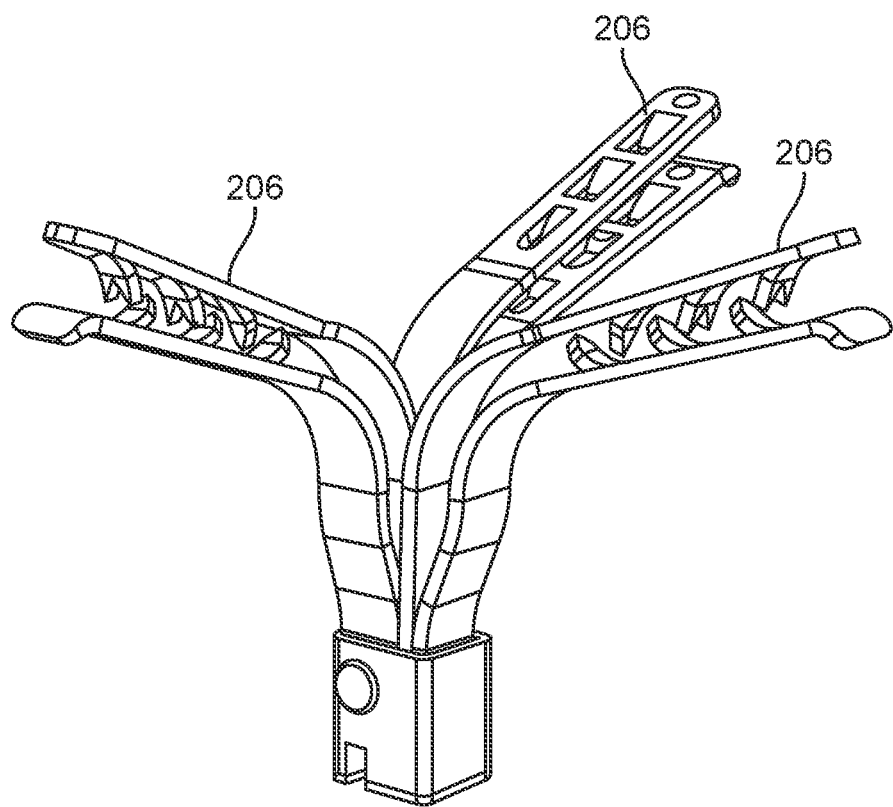
FIG. 13E illustrates an exemplary embodiment with three pairs of inner and outer arms. This to capture separate 3 leaflets, for example, in a tricuspid valve.

FIG. 13E shows an embodiment of a valve clip fixation device wherein there are three pairs of inner and outer arms 206. This, to grasp three sets of leaflets such as a tricuspid valve.

Figures 2, 13F:
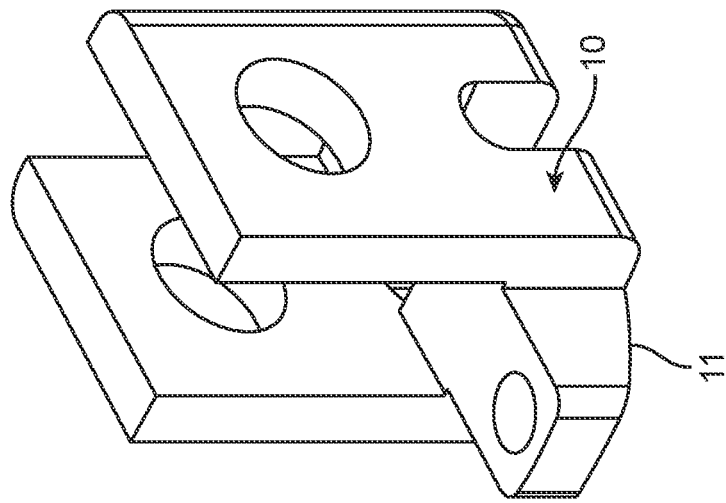
Figures 1, 13F:
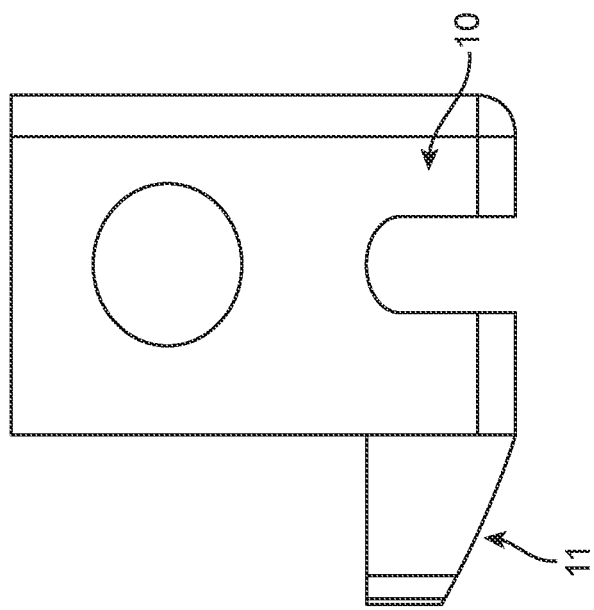

FIGS. 13F-1 and 13F-2 show an exemplary embodiment of base bracket 10 with a slanting feature 11 which enhances the ease of detachment of the fixation device up on removal of release rod 18 during deployment.

Figures 4, 13G:
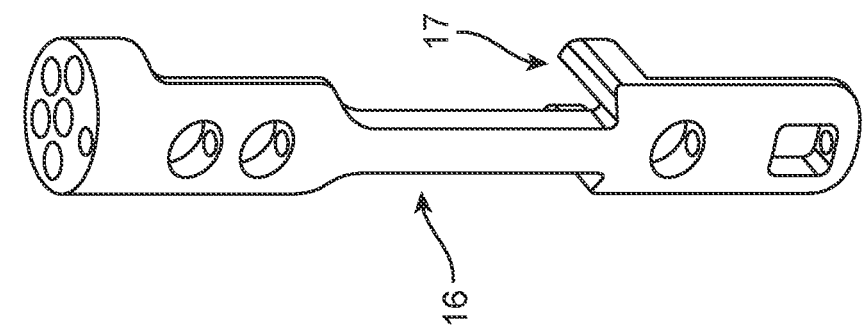
Figures 3, 13G:
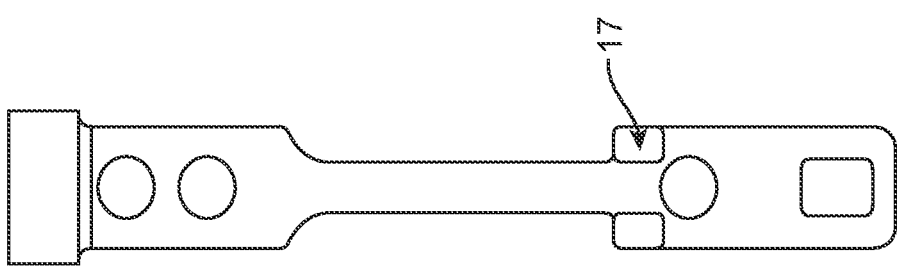
Figures 2, 13G:
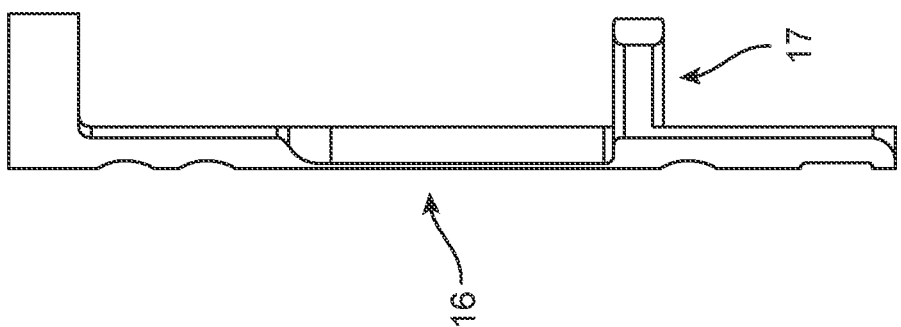
Figures 1, 13G:
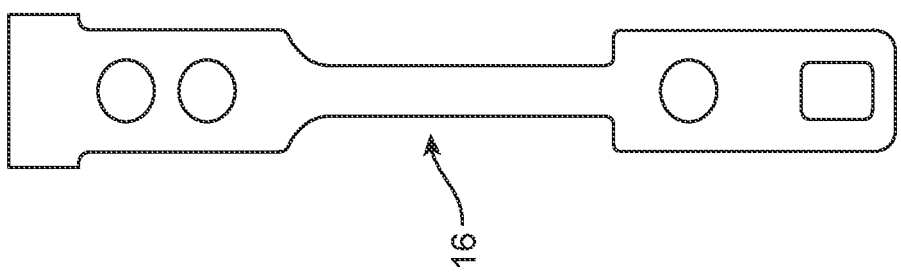

FIGS. 13G-1 through 13G-4 show an exemplary embodiment of a release bar 16, with two posts 17. The posts aid in spreading (or lowering) of the outer arms during capture of the leaflets while allowing for seamless detachment from the fixation device during deployment.

FIGS. 13H-1 and 13H-2 illustrate the function of the posts 17. FIGS. 13H-1 and 13H-2 show the back and side view of the release bar 16, respectively, and base bracket 10 and release rod 18 subassembly. Note, the arms are not shown for clarity. In the start position, the base bracket 10 is at a lower position and there is a gap 54 between the posts 17 and base bracket 10.

In FIGS. 13I-1 and 13I-2, the base bracket is manipulated towards the post 17, using, for example wire or sutures connected to one of the delivery catheter handle knobs. This manipulation results in reduction of the gap 54.

Figures 1, 13J:
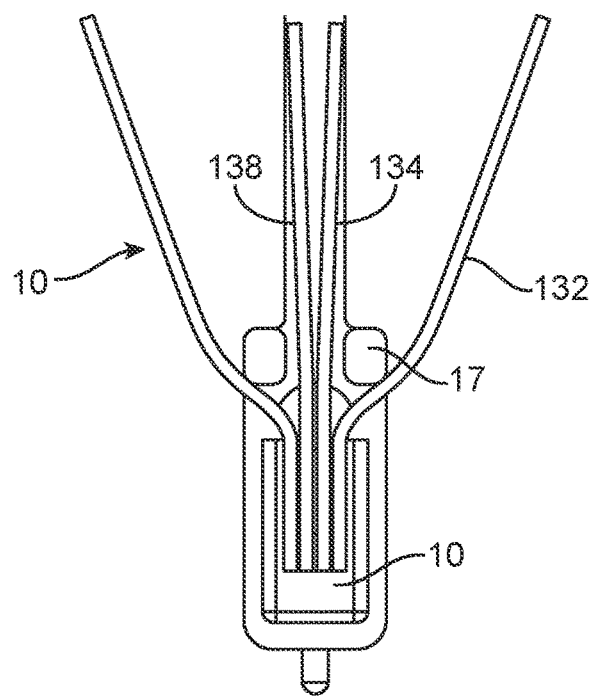
Figures 2, 13J:
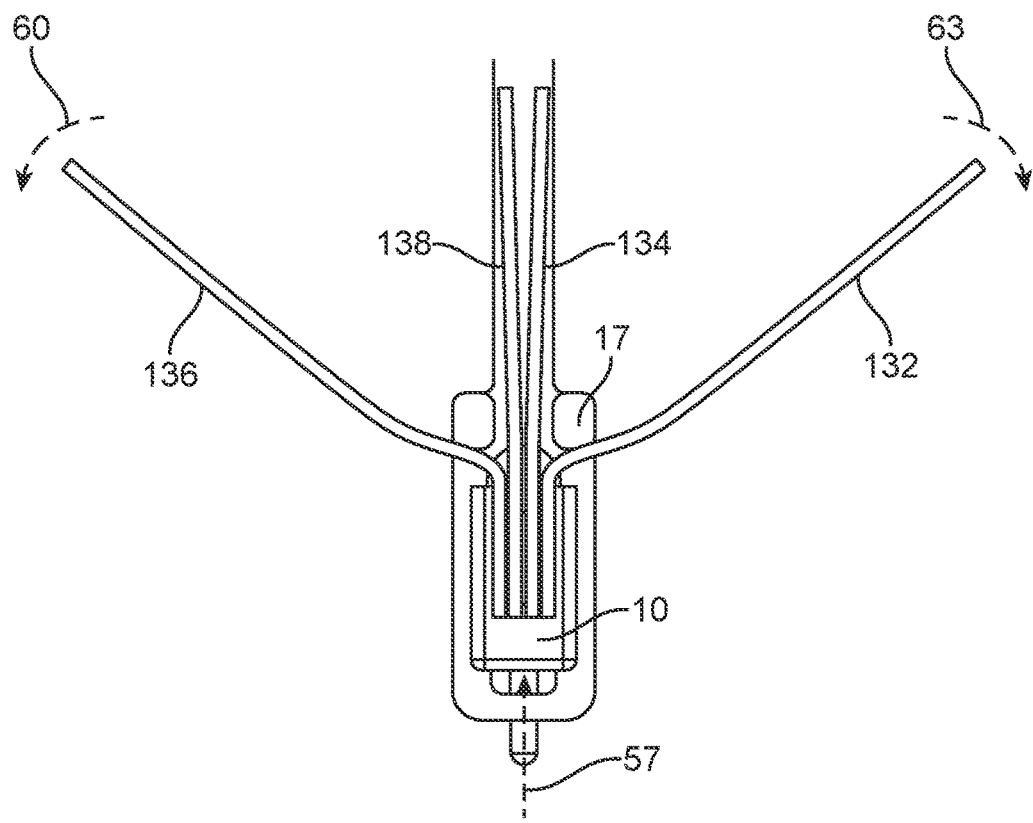

FIGS. 13J-1 and 13K-2 show the a portion of the front view of the release bar 16, release rod 18, and schematics of outer arms 132, 136 and inner arms 134, 136. FIG. 13J-1 shows the base bracket 10 in start position. In this exemplary embodiment, the inner and outer arms are typically made of a superelastic material such as nitinol. The outer arms are shape-set towards a vertical position while the inner arms are shape-set towards the horizontal position. Thus, there is a constant bias for the outer arms to move towards the vertical position as in FIG. 13D, while the inner arms are constantly biased towards the outer arms. Further, the outer arms are made stronger in comparison to inner arms, for example by using thicker outer arms. Further, the inner arms are positioned in a raised position using previously described techniques, for example in FIG. 9D. Therefore, the outer arms are constrained only by the posts 17. In FIG. 13J-2, the base bracket 10 is manipulated upwards towards the posts 17. This results in the desired lowering of the outer arms, as they are pushed down against the posts 17.

Figures 1, 13K:
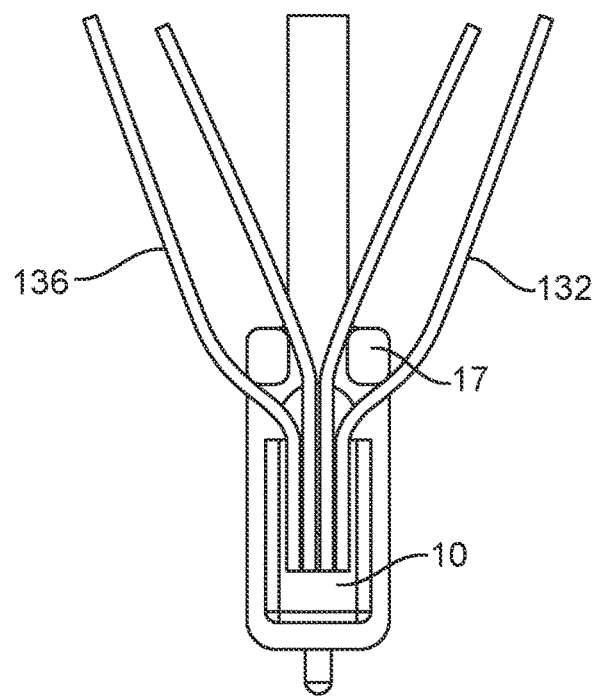
Figures 2, 13K:
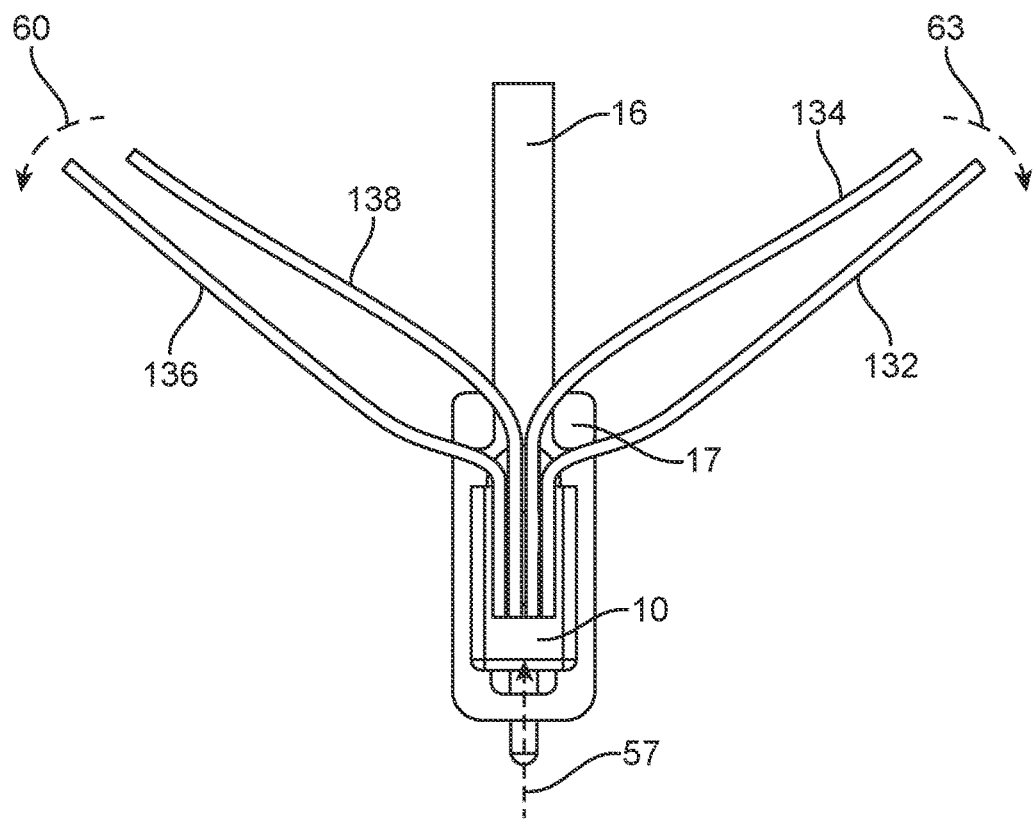

FIGS. 13K-1 and 13K-2 are similar to FIGS. 13J-1 and 13J-2, with the inner arms 134, 138 pre-set to be in a lowered position.

Although in FIGS. 13G-1 through 13K-2 show posts that are fixed to the Release bar 16, it will be obvious to those skilled in art to make the posts movable. For example, the posts may be mounted on a lever arm and hinged to the release bar 16 and be used to manipulate the arms with a mechanical advantage using tethers.

Figure 14:
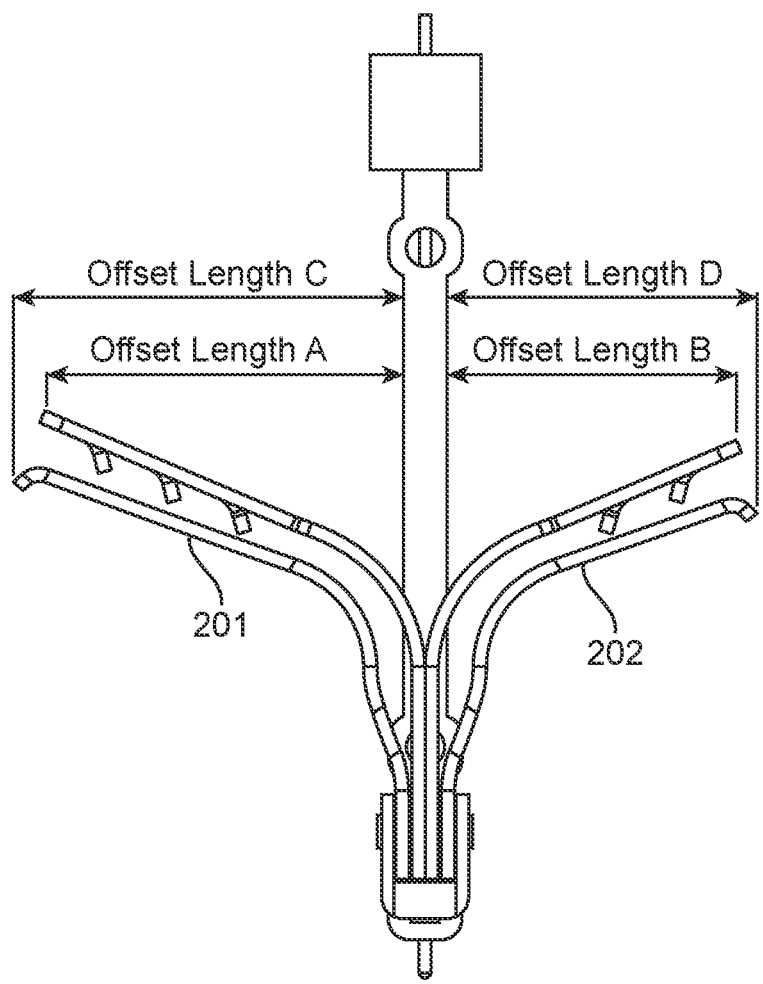
FIG. 14 illustrates further embodiment configurations of the fixation device in which arms of either side are of different lengths.

FIG. 14 shows an example of an embodiment wherein the outers arms do not have barbs or frictional elements. Alternatively, the inner arms may or may not have barbs or fictional elements. Further, the length of each individual inner or outer arm may vary such that:

Offset lengths A=0 to 100 mm, B=0 to 100 mm; C=0 to 100 mm, D=0 to 100 mm; and A≥B; or B≥A; or B≠A; C≥D; or D≥C; or C≠D; B≥D; or D≥B; or B≠D; A≥C; or C≥A; or C≠A. Note, that although only the offset lengths were depicted, the same may be applied to individual physical length of the entire arm or to just the section of the arm that engages with the leaflets. That is, each individual arm maybe of different size in thickness, length and width.

Figure 15:
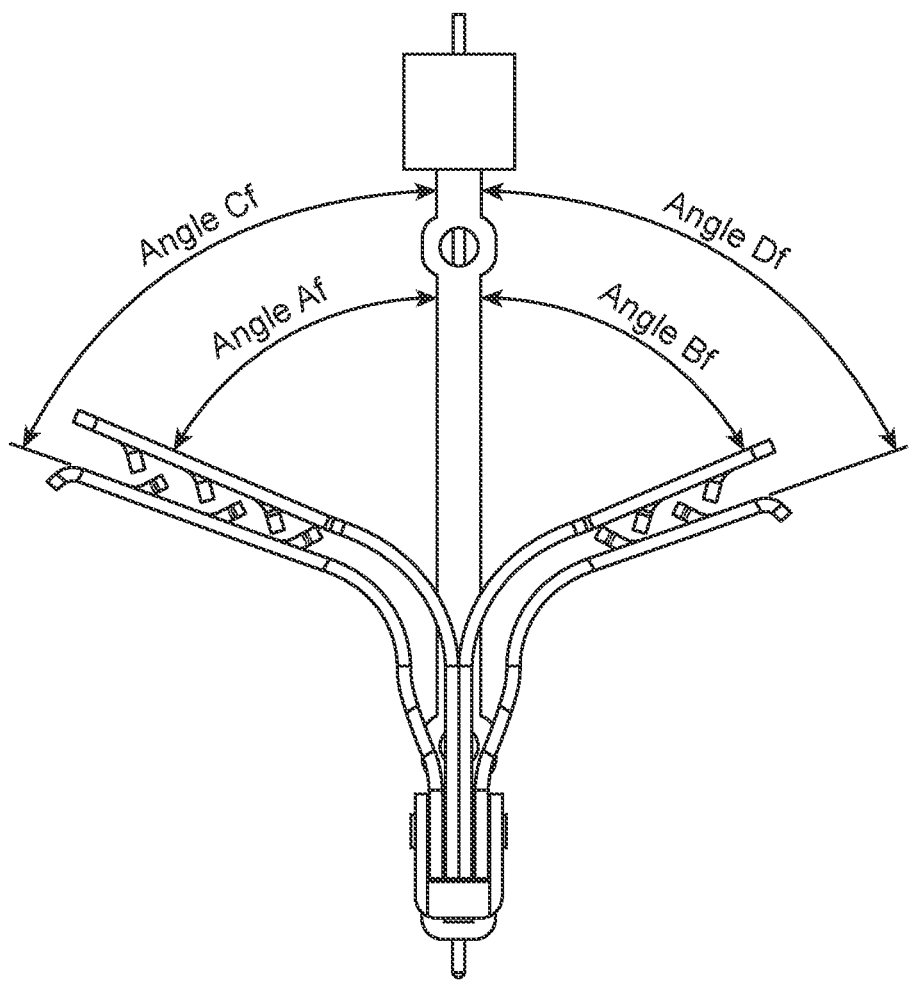
FIG. 15 illustrates further embodiment configurations of the fixation device in which arms of either side are of different angles.

FIG. 15 illustrates various configuration of the fixation device embodiments, such that the final angle (Af, Bf, Cf, Df)=0 to 180 degrees; and Angle Af≥Angle Bf; or Angle Af≤Angle Bf; or Angle Af≠Angle Bf; Angle Cf≥Angle Df; or Angle Cf≤Angle Df; or Angle Cf≠Angle Df; Angle Af≥Angle Cf; or Angle Af≤Angle Cf; or Angle Af≠Angle Cf; Angle Bf≥Angle Df; or Angle Bf≤Angle Df; or Angle Bf≠Angle Df. Note, in a preferred configuration, the inner and outer arms are elastically or super-elastically biased towards each other with sufficient force, so as to securely capture the leaflets when place between them.

Figure 16:
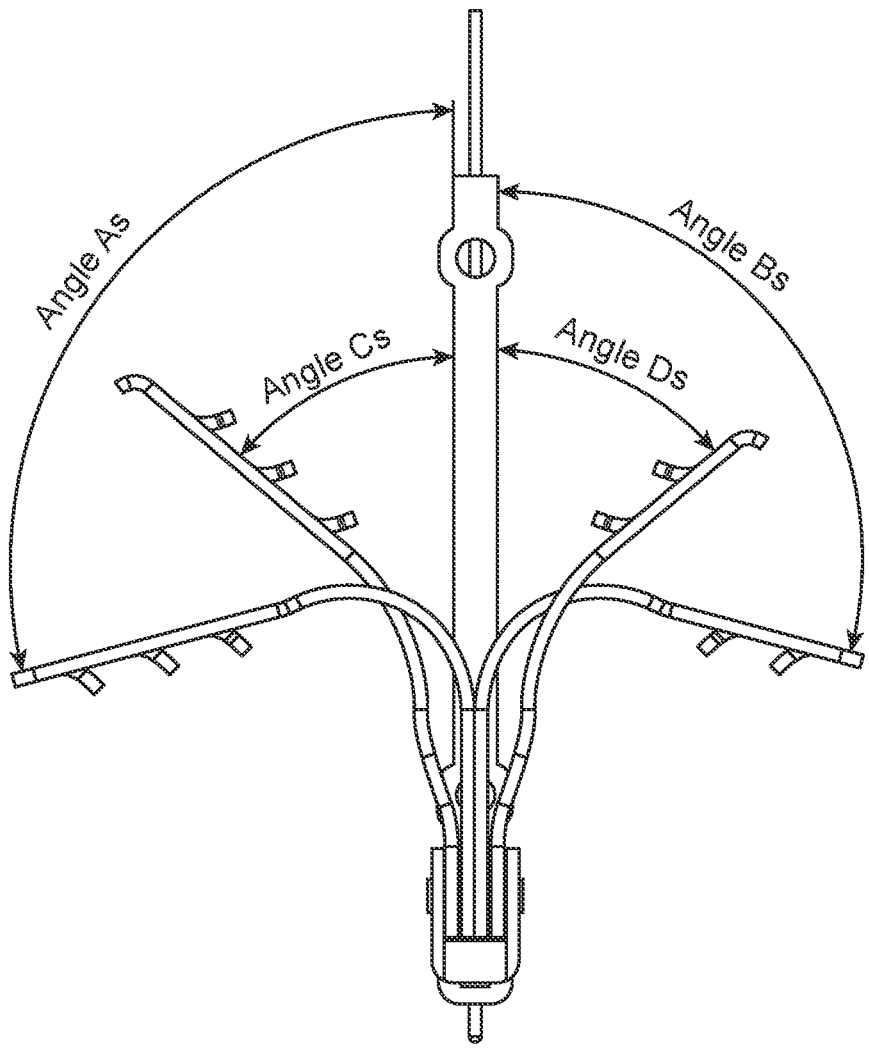
FIG. 16. illustrates further embodiment configurations of the fixation device in which arms of either side are of different angles at shape-set or unconstrained angles.

FIG. 16 illustrates various configuration of the fixation device embodiments, such that the final angle (As, Bs, Cs, Ds)=0 to 180 degrees; and Angle As ≥Angle Bs; or Angle As≤Angle Bs; or Angle As≠Angle Bs; Angle Cs≥Angle Ds; or Angle Cs≤Angle Ds; or Angle Cs≠Angle Ds; Angle As≥Angle Cs; or Angle As≤Angle Cs; or Angle As≠Angle Cs; Angle Bs≥Angle Ds; or Angle Bs≤Angle Ds; or Angle Bs≠Angle Ds. Note that in a preferred embodiment, final and shape-set angles may have the following relationship: Angle Af≤Angle As; Angle Bf≤Angle Bs; Angle Cs≤Angle Cf; Angle Df≤Angle Ds; Angle As≠Angle Bf; Angle Cs≠Angle Ds.

Figures 11B, 11C:
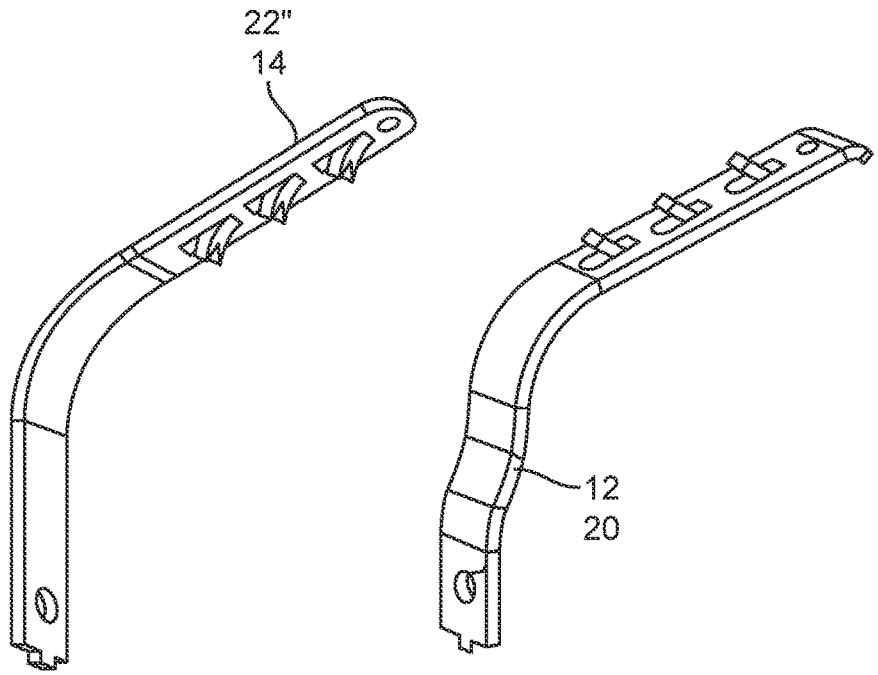
Figure 11D:
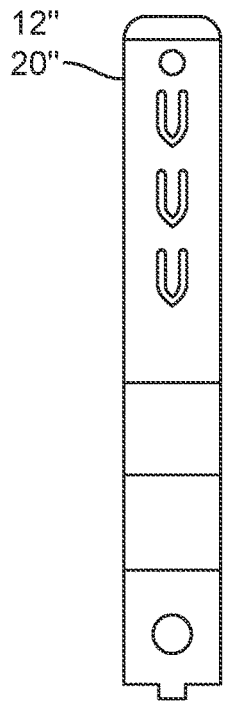
Figure 17A:
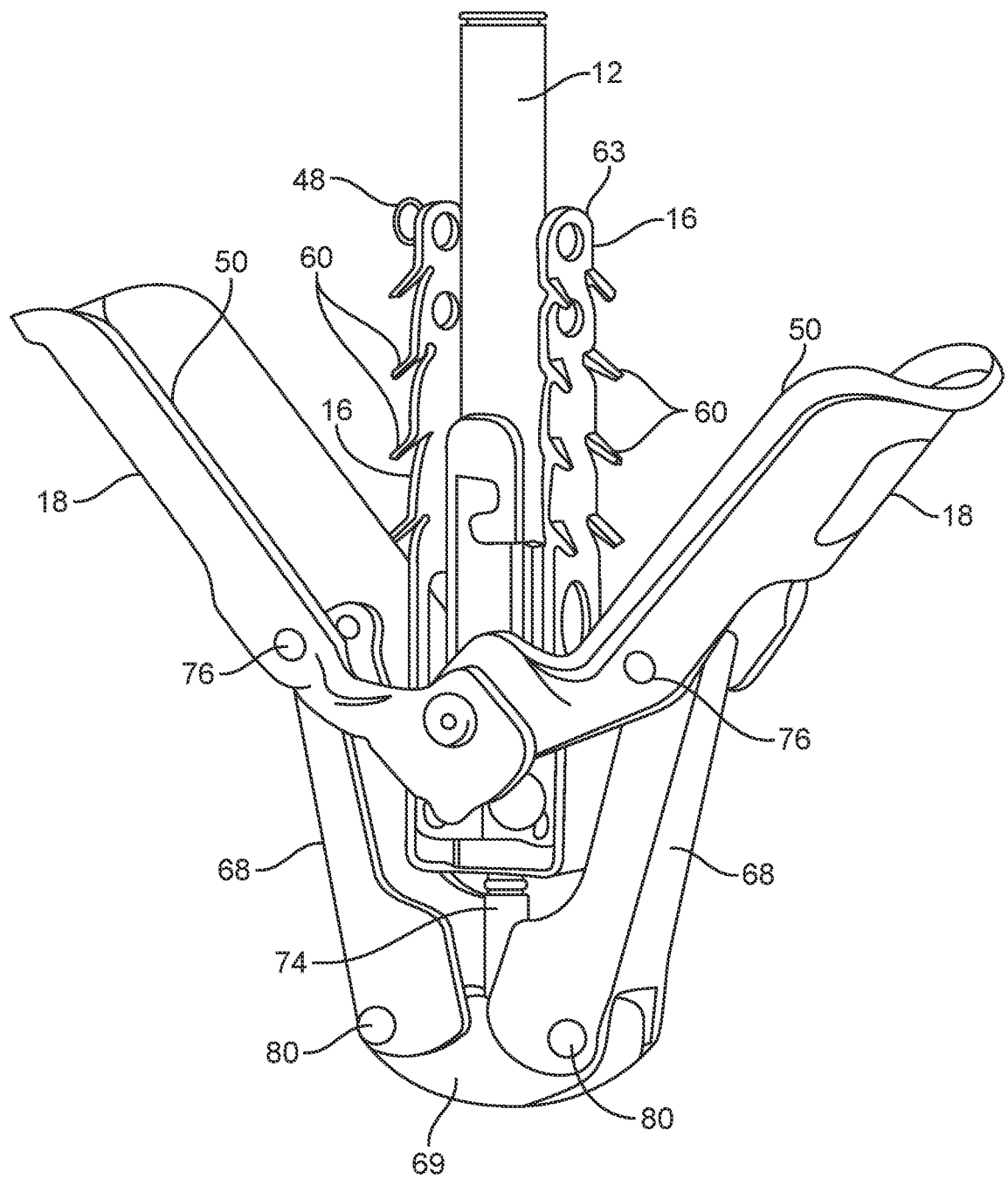
FIG. 17A reproduces a MitraClip® embodiment (FIG. 11B, U.S. Pat. No. 8,057,493 B2; page 8 of 68), showing inner gripping arms with exposed barbs 60 on the sides.

FIG. 17A reproduces a MitraClip® embodiment (FIG. 11B, U.S. Pat. No. 8,057,493 B2; page 8 of 68), showing inner gripping arms with exposed barbs 60 on the sides.

Figure 17B:
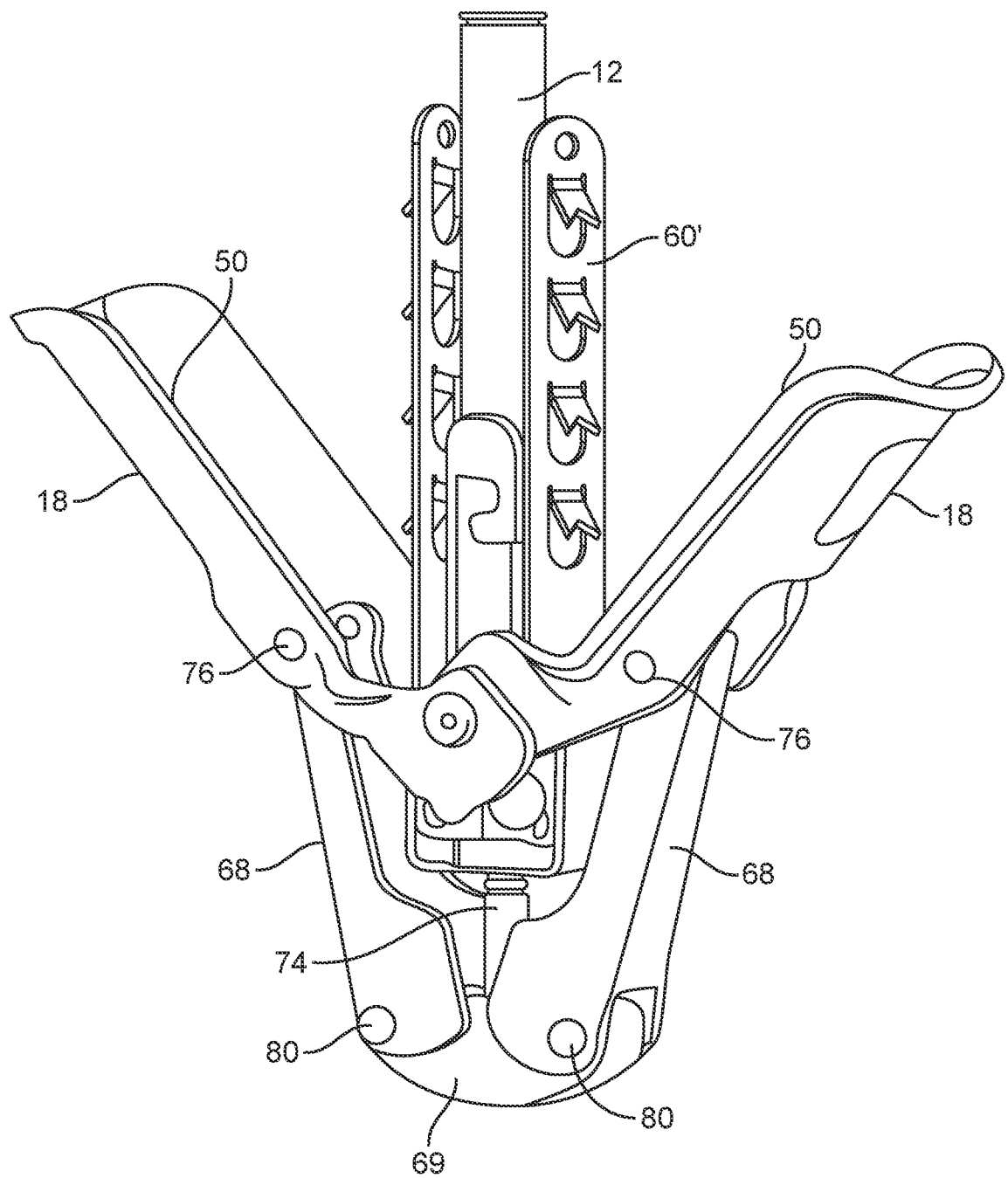
FIG. 17B illustrates an improvement upon the Mitraclip® device in which the barbs 60 have been repositioned within the width of the arms 60', in lines with the tangle-resistant aspects of this invention.

FIG. 17B depicts a further embodiment of this invention, wherein the MitraClip® external barbs 60 in FIG. 17A have been replaced and redesigned with internal barbs 60' (FIG. 17B), in-line with current invention. In this invention, designing the arms such that the barbs are within the arms rather than on the exterior of the arms further ensures that chordae, tissue or delivery device components (for example sutures or wires) are not un-intentionally or accidentally caught, tangled or be structurally compromised during manipulations of the fixation device in the heart.

Figure 18A:
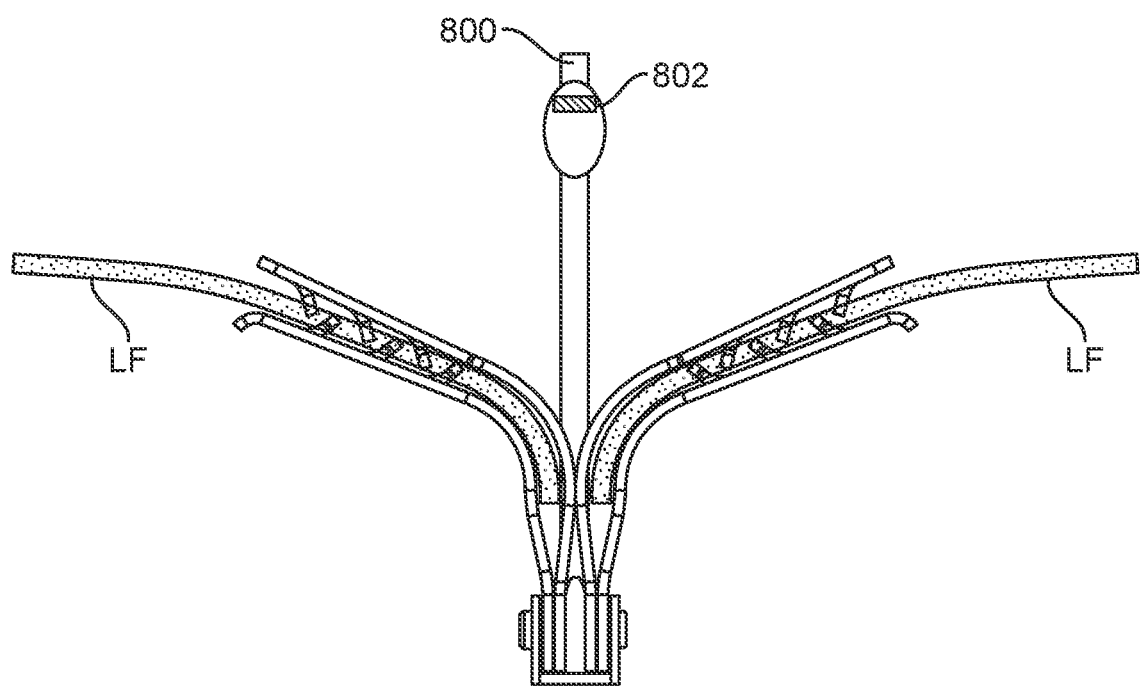
FIG. 18A through 18E illustrate further embodiments of the fixation device which utilizes a camera/optic system with various styles of viewing balloons to provide a visual during deployment.
Figure 18B:
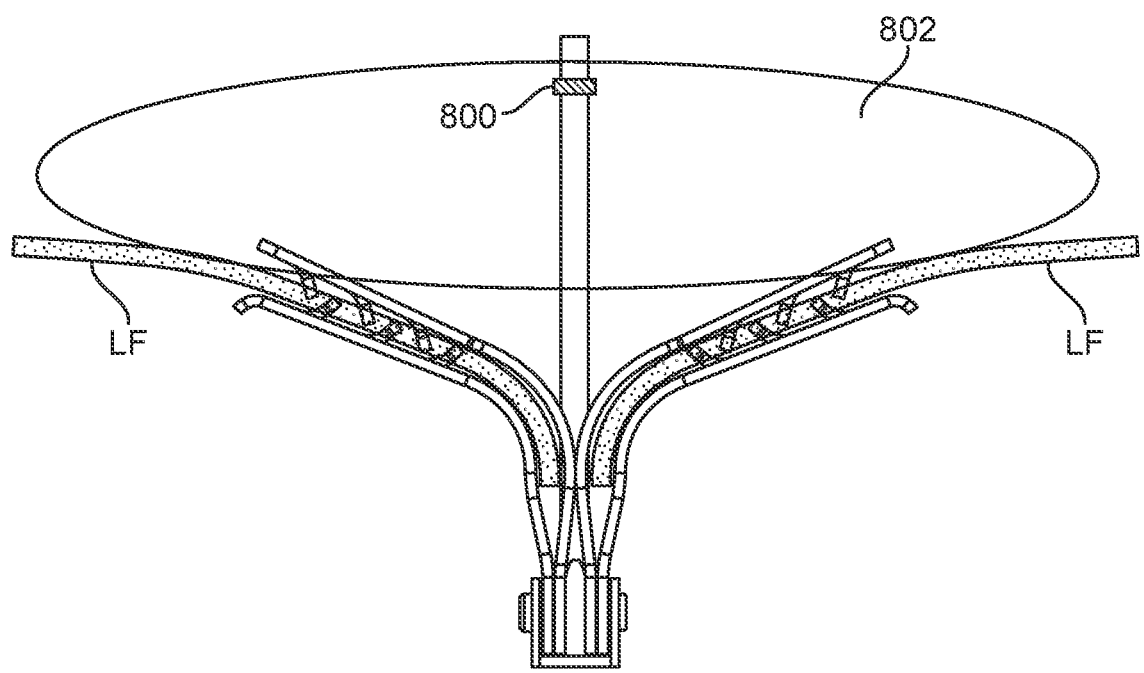
Figure 18C:
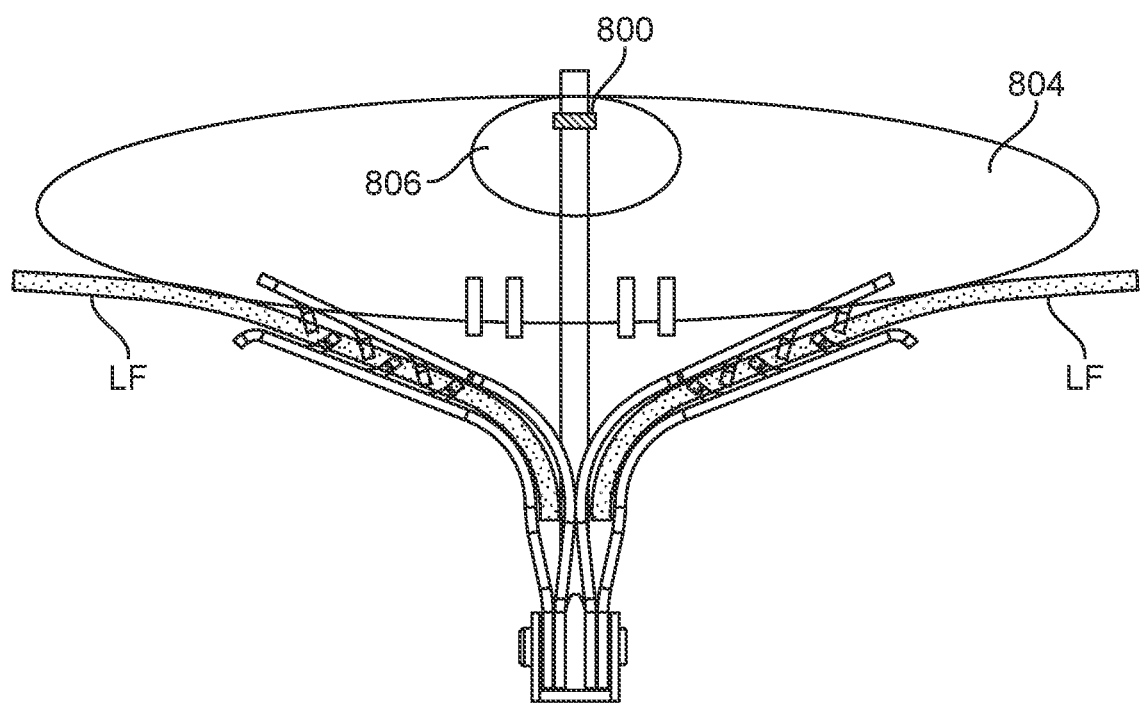

FIG. 18A through 18C illustrates an embodiment to assist visualization of fixation during the procedure. It is achieved via an optic camera with light source 800 embedded inside a balloon 802 filled with clear liquid such as saline or DI water. Alternatively, the in-situ camera and or the light source may be replaced with optic-fiber based scope.

FIG. 18B shows an example of embodiment wherein the balloon is inflated via the delivery catheter lumen, optical visualization is achieved along the surface of the transparent balloon. In this embodiment, a semi-compliant or variable stiffness balloon configuration may be used. During deployment, the balloon 802 is inflated with clear saline or DI water to contact the clip and/or tissue to provide visual feedback via the camera 800. Visual feedback can be used for planning and performing the procedure.

FIG. 18C show an example of a porous outer balloon 804 surrounding an non-porous interior balloon 806 surrounding the optic camera with light source 800 the porous outer balloon displaces ambient blood for improved visualization.

Figure 18D:
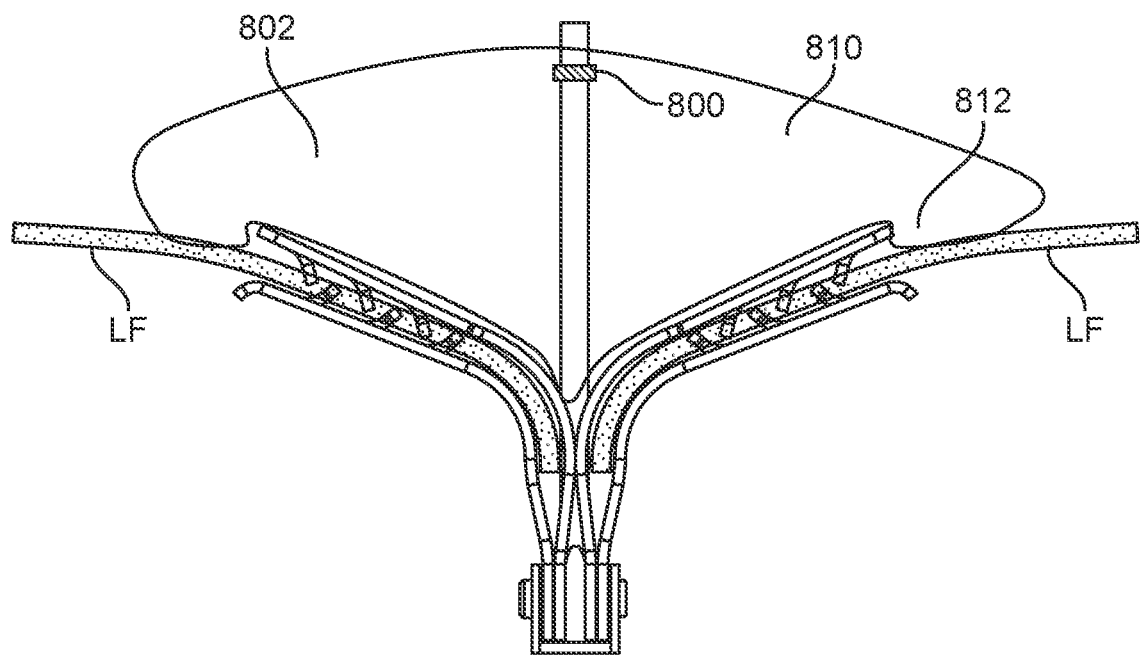

FIG. 18D shows the optic camera with light source 800 on a retractable/steerable structure inside of a balloon 808 with variable compliance. A high compliance inner surface 812 of the balloon conforms to the upper surfaces of the clips and leaflets to provide improved contact for increased visualization. The upper surface 812 of the balloon can be stiffer to assure full expansion of the balloon 810 over the clip and leaflets. The balloon 810 may be on the delivery catheter or implant or may be as a standalone device.

Figure 18E:
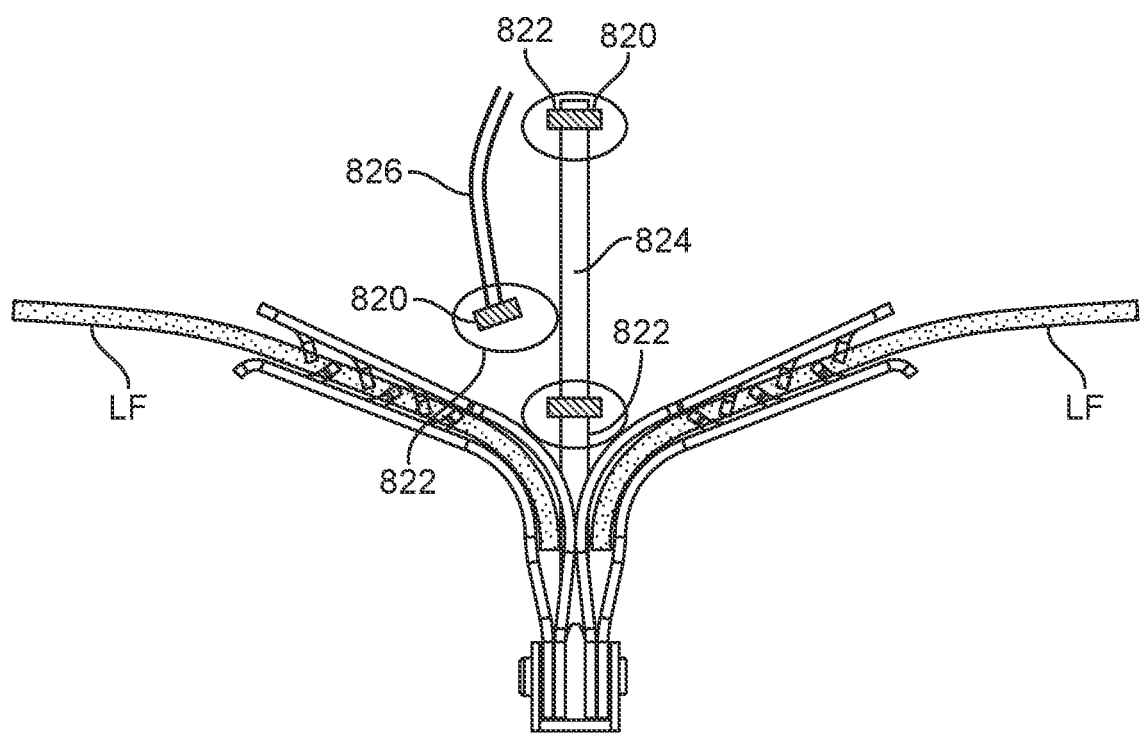

FIG. 18E shows a pair of optical cameras or fiber-optic sensors 820 housed within or on balloons 822 that are mounted on a retractable/steerable structure 824. Alternatively, these sensors/cameras may be mounted on a steerable/retractable shaft 826.

Figure 19:
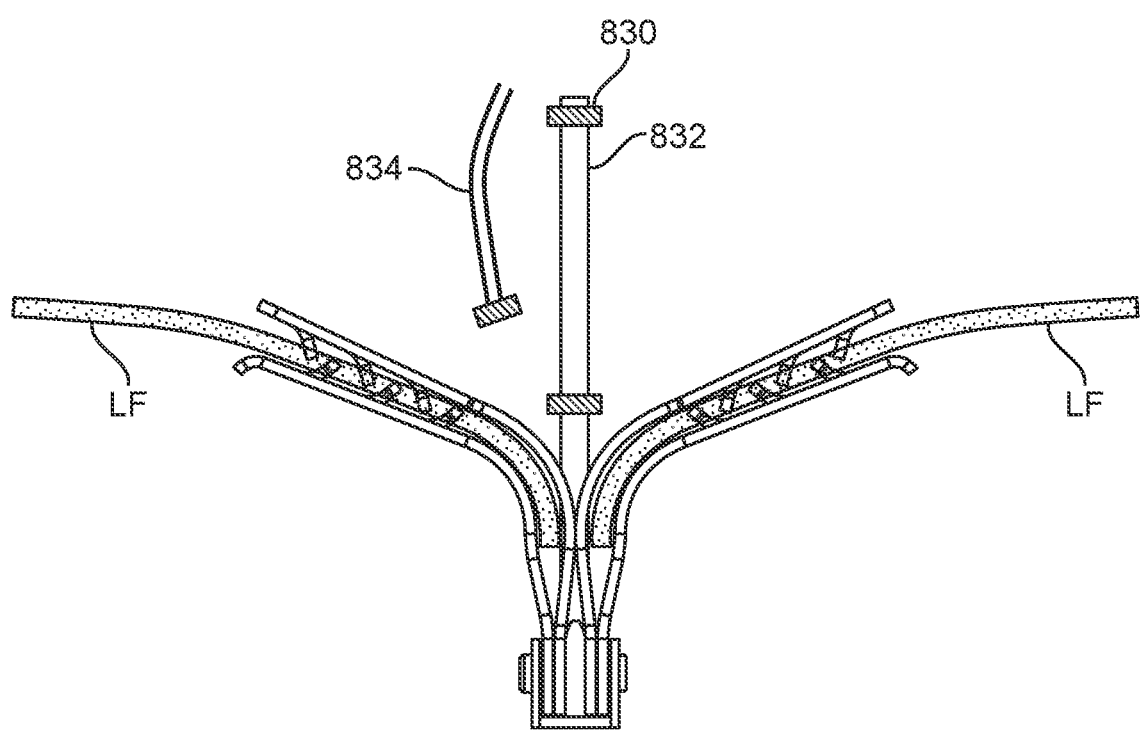
FIG. 19 illustrates a further embodiment of the fixation device which utilizes OCT sensors to provide a visual during deployment.

FIG. 19 shows one or more optical coherence tomography (OCT) sensors 830 attached to a distal shaft 832 of the delivery system. These sensors 830 may be mounted in multiples, or on a retractable and/or steerable shaft 834. This would allow for high-resolution tissue and delivery device imaging during implantation.

Figure 20:
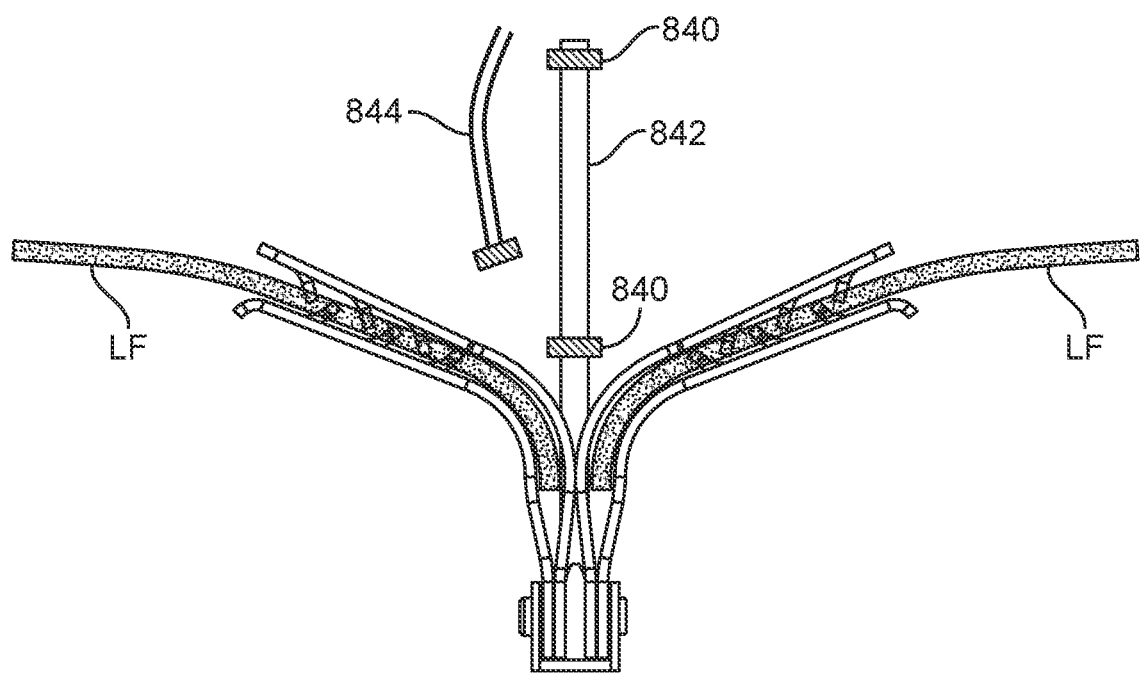
FIG. 20 illustrates a further embodiment of the fixation device which utilizes ultrasound echography sensors to provide a visual during deployment.

FIG. 20 shows one or more ultrasound sensors 840 attached to a distal shaft 842 of the delivery system. These sensors 840 may be mounted in multiples, or on a retractable and/or steerable shaft 844. This would allow for 2D, 3D, and Doppler modalities integrated to help navigate and perform the procedure.

Note that any combination of the embodiments illustrated in FIGS. 18A-E through 20 may be used as a part of this invention, to accomplish visualization. In a preferred embodiment, these visualization ideas disclosed should be sufficient to replace transesophageal echocardiogram (TEE) and or fluoroscopy. TEE is one of the primary reason for patient to undergo general anesthesia during the procedure. Hence, eliminating the requirement for TEE during the procedure reduces the risks associated with general anesthesia. While reducing fluoroscopy lowers the risks from x-rays.

Sensors and actuators that may be used in relation to this invention, to improve the safety, ease of use, and efficacy of the delivery system and fixation device. Sensors and actuators may be used to assist and evaluate device delivery (acute) and efficacy (acute or chronic). Sensors and actuators maybe active or passive, removable or implantable and may provide acute or chronic physiological or non-physiological data to assess or evaluate patient health. Sensors and actuators may be active or passive, removable or implantable and provide acute or chronic physiological or non-physiological data to access or evaluate implant integrity and or function Sensors maybe used for visualization: thermal, optical, ultrasonic (including ICE), OCT, fluoroscopic Sensors and actuators maybe electrical, mechanical, magnetic, RF, chemical or combination. Sensors and actuators maybe wired or wireless and may communicate with mobile or fixed external interface. The catheters of the present invention may be used as a conduit for external sensors, for example pressure sensor replacing Swan-Ganz catheter The term sensor and actuator maybe used interchangeably. Sensors and actuators listed are for examples only. Any suitable metal or polymer or ceramic, organic or inorganic, flexible or rigid, matrix or material and their combinations may be used to produce the desired sensors and actuators.

All implant embodiments described in this invention maybe optionally covered, wrapped, coated, or the like to improve biocompatibility and tissue interface. Suitable coverings can be fabric, web, fibrous, braid, woven or non-woven. The coatings can be metallic, ceramic, polymeric, or combinations thereof. Suitable metallic coatings include titanium, TiN, tantalum, gold, platinum, and alloys thereof. Suitable ceramic and inorganic coatings include titanium dioxide, hydroxyapatite, CaP, and the like. Suitable polymeric coatings include fluoropolymers, e.g. PTFE, PFA, FEP, ECTFE, ETFE; parylene, polyester, PET, polypropylene, PEEK, PVDF, HDPE, LDPE, UHMWPE, phosphorylcholine, THV, and the like. Suitable biodegradable include poly(lactic acid), poly(glycolic acid), polydioxanone, poly (ε-caprolactone), polyanhydride, poly(ortho ester), copoly (ether-ester), polyamide, polylactone, poly(propylene fumarate), and their combinations. Such metallic, ceramic and/or polymeric coatings are listed as examples only. Any suitable metal, ceramic, polymer, and combination thereof may be used to produce a desirable coating.

The following is a listing of the reference numbers used in this application:
- 10 Base bracket, of the fixation device in the preferred embodiment.
- 11 Slanted section of base bracket 10 for enhanced ease of deployment
- 12 Outer arm, of the preferred embodiment used to capture leaflet.
- 14 Inner arm, of the preferred embodiment used to capture leaflet.
- 16 Release bar, the distal most component of the delivery catheter that interfaces with the fixation device.
- 17 Posts on Release bar 16 to enable spreading/lowering of the Outer Arms
- 18 Release rod; long rod running through delivery system that attaches Base bracket 10 of the fixation device to the Release bar 16; pulling the rod 18 releases and deploys the fixation device.
- 20 Outer arm, exemplary embodiment of a fixation device used to capture leaflet.
- 22 Inner arm, exemplary embodiment of a fixation device used to capture leaflet.
- 24 Fastener holding arms of fixation device to the Base bracket (10) in the preferred embodiment.
- 26 Feature of Release bar (16) allowing sutures to loop through and manipulate the arms of the fixation device.
- 28 A feature of Release bar 16 that attaches delivery catheter shaft 499.
- 30 Feature of Release bar (16) allowing sutures to loop through and manipulate the arms of the fixation device.
- 32 Feature of Release bar 16 allowing for passage of sutures
- 34 Feature of Release bar 16 allowing for passage of sutures
- 36 Feature of Release bar 16 allowing for passage of sutures
- 38 Feature of Release bar 16 allowing for passage of sutures
- 41 Segment of suture 47
- 42 Segment of suture 47
- 43 Segment of suture 48
- 44 Segment of suture 48
- 47 Suture allowing control of outer arm 12
- 48 Suture allowing control of arm 20
- 51 Manipulation of suture 47
- 52 Manipulation of suture 48
- 54 Gap between the Post 17 and Outer base 10
- 57 Manipulation of Outer base 10 relative to Release bar 16
- 60 Manipulation of outer arms
- 60 Barbs used in grabbing leaflet tissues in a particular embodiment
- 61 Manipulation of outer arms
- 62 Manipulation of inner arms
- 63 Manipulation of inner arms
- 64 Manipulation of inner arms
- 65 Manipulation of inner arms
- 71 Segment of suture 75
- 72 Segment of suture 76
- 73 Segment of suture 75
- 74 Segment of suture 76
- 75 Suture allowing control of inner arm 14
- 76 Suture allowing control of inner arm 22
- 77 Manipulation of suture 75; collapses inner arm 14
- 78 Manipulation of suture 76; collapses inner arm 22
- 82 Suture loop at end of inner arm 22 allowing for manipulation sutures to engage arm; unneeded if suture is run through the arm itself
- 83 Suture loop at end of inner arm 14 allowing for manipulation sutures to engage arm; unneeded if suture is run through the arm itself
- 91 Segment of suture 95
- 92 Segment of suture 97
- 93 Segment of suture 95
- 94 Segment of suture 97
- 95 Suture allowing control of arm 12
- 96 Suture allowing control of sutures 95 and 97
- 97 Suture allowing control of arm 20
- 98 Suture loop used to constrain sutures 95 and 97
- 101 Segment of suture 96
- 102 Segment of suture 97
- 103 Segment of suture 95
- 110 Manipulation of suture segment 93
- 111 Manipulation of suture segment 94
- 112 Manipulation of suture segment 98
- 120 Feature of release bar allowing for fastening of the fixation device through feature 130
- 121 Embodiment of outer arm with shorter length
- 122 Embodiment of inner arm with shorter length
- 130 Protruding feature of bracket (24) allowing for the fastening of the fixation device to the release bar 16 using feature 120
- 132 Outer arm in a particular embodiment
- 134 Inner arm in a particular embodiment
- 136 Outer arm in a particular embodiment
- 138 Inner arm in a particular embodiment 161 A feature of Release bar 16 that attaches delivery catheter shaft 499 in a retrograde embodiment
162 Feature of release bar (16) allowing for the fixation device to be secured to the delivery system through feature 130 in a retrograde embodiment
164 Feature of release bar (166) allowing sutures to loop through and manipulate the arms of the fixation device in a retrograde embodiment
166 Release bar, in retrograde configuration
168 Feature of release bar (166) allowing sutures to loop through and manipulate the arms of the fixation device in a retrograde embodiment
180 Manipulation of release rod (18) releasing the fixation device from the delivery system
201 Outer arm piece in a particular embodiment
202 Inner arm piece in a particular embodiment
203 Spacer providing gap for tissue capture between arms in a particular embodiment
204 Outer arm of a particular embodiment
400 Radiopaque marker(s) of Steerable Guide Catheter
401 Intermediate Steerable Guide shaft section allowing stiffness transition for 2-way and or 4-way steering
402 Distal Steerable Guide shaft section allowing for 2-way and or 4-way steering
403 Dilator
405 Proximal shaft of Steerable Guide Catheter
498 Shaft of Guide catheter
499 Shaft of Delivery catheter
500 Knob used alongside knob 501 to provide four-way steering to distal Delivery shaft (499) in a particular embodiment
501 Knob used alongside knob 500 to provide four-way steering to distal Delivery shaft (499) in a particular embodiment
502 Knob used to raise and lower inner/outer arms of fixation device
503 Knob used to raise and lower inner/outer arms of fixation device
504 Knob providing two-way steering to Delivery catheter distal shaft (499) in a particular embodiment
505 Knob providing two-way steering to distal steerable guide sheath (498) in a particular embodiment
508 Particular embodiment of a Delivery catheter handle holding knobs 502 and 503
510 Particular embodiment of a steerable guide catheter handle holding knob 505
511 Particular embodiment of a catheter handle holding knobs 502 and 503
515 Particular embodiment of a Delivery catheter handle holding knobs 502, 503, and 518
517 Particular embodiment of a Delivery catheter handle holding knobs 502, 503, 520, and 521
518 Knob providing two-way steering to distal delivery shaft (499) in a particular embodiment
520 Knob used alongside 521 to provide four-way steering to distal delivery shaft (499) in a particular embodiment
521 Knob used alongside 520 to provide four-way steering to distal delivery shaft (499) in a particular embodiment
523 Particular embodiment of a steerable guide catheter handle holding knobs 528 and 529
528 Knob used alongside 529 to provide four-way steering to steerable distal guide sheath (498) in a particular embodiment
529 Knob used alongside 528 to provide four-way steering to steerable distal guide sheath (498) in a particular embodiment
550 Quarter-turn locking Release rod 18 knob
615 Stainless steel sheath to support Delivery Handle
623 Stainless steel sheath to support Steerable Guide Handle
700 Etched markings used to indicate the function of various catheter knobs (e.g. 529)
702 Etched markings used to indicate the function of various catheter knobs (e.g. 528)
715 Delivery Catheter flush port
725 Steerable Guide Catheter flush port
727 Steerable Guide hemostasis valve lock
730 Quarter-turn locking Dilator 403 knob
735 Pinch lockable hemostasis valve on Steerable Guide
745 Exemplary embodiment of a custom steerable guide catheter handle, based on concept described in FIG. 2G
747 Exemplary embodiment of a custom delivery catheter handle, based on concept described in FIG. 2G
800 optic camera with light source
802 balloon filled with clear liquid
804 porous outer balloon
806 non-porous interior balloon
808 balloon with variable compliance
810 balloon over the clip and leaflets
812 upper surface of the balloon
820 optical camera or fiber-optic sensor
822 balloon
824 retractable/steerable structure
826 steerable/retractable shaft
830 optical coherence tomography sensors 8 attached to a
832 distal shaft
834 retractable and/or steerable shaft.
840 ultrasound sensors
842 distal shaft
844 retractable and/or steerable shaft
LF Leaflet of mitral valve Although many embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:
1. A method for clipping an anatomical valve, said method comprising:

advancing a valve clip having a pair of outer arms and a pair of inner arms to a location adjacent to the anatomical valve;

biasing at least one of (1) the pair of outer arms and (2) the pair of inner arms to open a valve leaflet capture space between adjacent outer and inner arms, wherein biasing comprises tensioning tethers attached to the at least one pair of outer or inner arms;

positioning the valve clip so that one valve leaflet is positioned in the valve leaflet capture space between left outer and inner arms and another valve leaflet is positioned in the valve leaflet capture space between right outer and inner arms;

releasing bias on the at least one pair of outer or inner arms so that the left outer and inner arms and the right outer and inner arms self-close over and secure the valve leaflets; and lifting the inner arms from over the valve leaflets to release the valve clip from the leaflets to allow repositioning or removal of the valve clip after an initial placement.

2. A method as in claim 1, wherein the anatomical valve is a heart valve.

3. A method as in claim 2, wherein the heart valve is a mitral valve.

4. A method as in claim 1, wherein the anatomical valve is a venous valve.

5. A method as in claim 1, wherein releasing bias comprises releasing tension on the tethers.

6. A method as in claim 1, wherein at least some of the inner and outer arms are formed as a leaf spring with a base attached to a valve-grasping element extending from the base.

7. A method as in claim 6, further comprising repositioning the valve clip with a delivery catheter engaging a delivery releasably attached to the valve-grasping element.

8. A method as in claim 7, wherein the valve-grasping elements diverge from the base to form a V-shape when the outer and inner arms are unbiased.

9. A method as in claim 8, wherein the base is curved and the valve-grasping element is straight the outer and inner arms pairs.

10. A method as in claim 9, wherein the valve-grasping elements are parallel to a common axis when the outer and inner arms are unbiased.

11. A method as in claim 6, wherein the outer arms are shape-set towards a position aligned with an axis of the valve clip when unbiased and the inner arms are shape-set towards a position transverse to the axis when unbiased so that the inner arms are biased towards the outer arms and wherein the outer arms have a stronger shape-set than the inner arms so that both pairs of inner and outer arms return to an orientation aligned with the axis of the clip when released from bias.

* * * * *